United States Patent
Volkman et al.

(10) Patent No.: US 11,369,662 B2
(45) Date of Patent: *Jun. 28, 2022

(54) METHODS OF TREATING INFLAMMATION WITH MONOMERIC CXCL12 PEPTIDE

(71) Applicant: The Medical College of Wisconsin, Inc., Milwaukee, WI (US)

(72) Inventors: Brian Volkman, Muskego, WI (US); Joshua Ziarek, Boston, MA (US); Christopher Veldkamp, Milwaukee, WI (US); Francis Peterson, Racine, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,809

(22) Filed: Jan. 17, 2020

(65) Prior Publication Data
US 2020/0353045 A1 Nov. 12, 2020

Related U.S. Application Data

(63) Continuation of application No. 15/874,476, filed on Jan. 18, 2018, now Pat. No. 10,537,613, which is a continuation of application No. 14/736,535, filed on Jun. 11, 2015, now Pat. No. 9,908,923.

(60) Provisional application No. 62/010,655, filed on Jun. 11, 2014.

(51) Int. Cl.
*A61K 38/16* (2006.01)
*A61K 38/19* (2006.01)
*C07K 14/52* (2006.01)

(52) U.S. Cl.
CPC .......... *A61K 38/195* (2013.01); *C07K 14/521* (2013.01)

(58) Field of Classification Search
None
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,563,048 A | 10/1996 | Honjo et al. | |
| 5,756,084 A | 5/1998 | Honjo et al. | |
| 7,923,016 B2 | 4/2011 | Volkman et al. | |
| 2006/0088510 A1 | 4/2006 | Lee et al. | |

OTHER PUBLICATIONS

Marks et al. (Clin. Rev. Allergy Immunol. 38(1): 20-31, 2010).*
McCandless et al. J. Immunol. 177: 8053-8064, 2006.*
Ma, Qing, et al. "Impaired B-lymphopoiesis, myelopoiesis, and derailed cerebellar neuron migration in CXCR4- and SDF-1-deficient mice." Proceedings of the National Academy of Sciences 95.16 (1998): 9448-9453.
Zou, Yong-Rui, et al. "Function of the chemokine receptor CXCR4 in haematopoiesis and in cerebellar development." Nature 393.6685 (1998): 595-599.
Sierro, Frederic, et al. "Disrupted cardiac development but normal hematopoiesis in mice deficient in the second CXCL12/SDF-1 receptor, CXCR7." Proceedings of the National Academy of Sciences 104.37 (2007): 14759-14764.
Burns, Jennifer M., et al. "A novel chemokine receptor for SDF-1 and I-TAC involved in cell survival, cell adhesion, and tumor development." Journal of Experimental Medicine 203.9 (2006): 2201-2213.
Hu, Xiaofeng, et al. "Stromal cell-derived factor-1α confers protection against myocardial ischemia/reperfusion injury." Circulation 116.6 (2007): 654-663.
Saxena, Ankur, et al. "Stromal cell-derived factor-1α is cardioprotective after myocardial infarction." Circulation 117.17 (2008): 2224-2231.
Proulx, Cindy, et al. "Antagonism of stromal cell-derived factor-1α reduces infarct size and improves ventricular function after myocardial infarction." Pflugers Archiv-European Journal of Physiology 455.2 (2007): 241-250.
Endres, Michael J., et al. "CD4-independent infection by HIV-2 is mediated by fusin/CXCR4." Cell 87.4 (1996): 745-756.
Balkwill, Fran. "Cancer and the chemokine network." Nature Reviews Cancer 4.7 (2004): 540-550.
Crump, Matthew P., et al. "Solution structure and basis for functional activity of stromal cell-derived factor-1; dissociation of CXCR4 activation from binding and inhibition of HIV-1." The EMBO journal 16.23 (1997): 6996-7007.
Kofuku, Yutaka, et al. "Structural basis of the interaction between chemokine stromal cell-derived factor-1/CXCL12 and its G-protein-coupled receptor CXCR4." Journal of Biological Chemistry 284.50 (2009): 35240-35250.
Farzan, Michael, et al. "The role of post-translational modifications of the CXCR4 amino terminus in stromal-derived factor 1α association and HIV-1 entry." Journal of Biological Chemistry 277.33 (2002): 29484-29489.
Seibert, Christoph, et al. "Sequential tyrosine sulfation of CXCR4 by tyrosylprotein sulfotransferases." Biochemistry 47.43 (2008): 11251.
Farzan, Michael, et al. "Tyrosine sulfation of the amino terminus of CCR5 facilitates HIV-1 entry." Cell 96.5 (1999): 667-676.
Preobrazhensky, Alexander A., et al. "Monocyte chemotactic protein-1 receptor CCR2B is a glycoprotein that has tyrosine sulfation in a conserved extracellular N-terminal region." The Journal of Immunology 165.9 (2000): 5295-5303.
Bannert, Norbert, et al. "Sialylated O-glycans and sulfated tyrosines in the NH2-terminal domain of CC chemokine receptor 5 contribute to high affinity binding of chemokines." Journal of Experimental Medicine 194.11 (2001): 1661-1674.

(Continued)

*Primary Examiner* — Christine J Saoud
(74) *Attorney, Agent, or Firm* — Quarles & Brady LLP

(57) ABSTRACT

The present invention provides a $CXCL12_1$ peptide engineered to resist peptide-induced dimerization by maintaining steric repulsion of the chemokine helix, pharmaceutical compositions thereof, and methods of using said dimer in the treatment of cancer, inflammatory disorders, autoimmune disease, and HIV/AIDS.

7 Claims, 38 Drawing Sheets

Specification includes a Sequence Listing.

(56) References Cited

OTHER PUBLICATIONS

Colvin, Richard A., et al. "CXCR3 requires tyrosine sulfation for ligand binding and a second extracellular loop arginine residue for ligand-induced chemotaxis." Molecular and cellular biology 26.15 (2006): 5838-5849.
Gutiérrez, Julio, et al. "Analysis of post-translational CCR8 modifications and their influence on receptor activity." Journal of Biological Chemistry 279.15 (2004): 14726-14733.
Fong, Alan M., et al. "CX3CR1 tyrosine sulfation enhances fractalkine-induced cell adhesion." Journal of Biological Chemistry 277.22 (2002): 19418-19423.
Rajarathnam, Krishnakumar, et al. "Neutrophil activation by monomeric interleukin-8." Cytokine 6.5 (1994): 549.
Paavola, Chad D., et al. "Monomeric monocyte chemoattractant protein-1 (MCP-1) binds and activates the MCP-1 receptor CCR2B." Journal of Biological Chemistry 273.50 (1998): 33157-33165.
Laurence, Jennifer S., et al. "CC chemokine MIP-1β can function as a monomer and depends on Phe13 for receptor binding." Biochemistry 39.12 (2000): 3401-3409.
Proudfoot, Amanda EI, et al. "Glycosaminoglycan binding and oligomerization are essential for the in vivo activity of certain chemokines." Proceedings of the National Academy of Sciences 100.4 (2003): 1885-1890.
Tan, Joshua HY, et al. "Design and receptor interactions of obligate dimeric mutant of chemokine monocyte chemoattractant protein-1 (MCP-1)." Journal of Biological Chemistry 287.18 (2012): 14692-14702.
Veldkamp, Christopher T., et al. "Structural basis of CXCR4 sulfotyrosine recognition by the chemokine SDF-1/CXCL12." Science signaling 1.37 (2008): ra4.
Drury, Luke J., et al. "Monomeric and dimeric CXCL12 inhibit metastasis through distinct CXCR4 interactions and signaling pathways." Proceedings of the National Academy of Sciences 108.43 (2011): 17655-17660.
Takekoshi, Tomonori, et al. "A locked, dimeric CXCL12 variant effectively inhibits pulmonary metastasis of CXCR4-expressing melanoma cells due to enhanced serum stability." Molecular cancer therapeutics 11.11 (2012): 2516-2525.
Veldkamp, Christopher T., et al. "Recognition of a CXCR4 sulfotyrosine by the chemokine stromal cell-derived factor-1α (SDF-1α/CXCL12)." Journal of molecular biology 359.5 (2006): 1400-1409.
Veldkamp, Christopher T., et al. "Targeting SDF-1/CXCL12 with a ligand that prevents activation of CXCR4 through structure based drug design." Journal of the American Chemical Society 132.21 (2010): 7242.
Veldkamp, Christopher T., et al. "The monomer-dimer equilibrium of stromal cell-derived factor-1 (CXCL 12) is altered by pH, phosphate, sulfate, and heparin." Protein Science 14.4 (2005): 1071-1081.
Veldkamp, Christopher T., et al. "Monomeric structure of the cardioprotective chemokine SDF-1/CXCL12." Protein Science 18.7 (2009): 1359-1369.
Ziarek, Joshua, et al. "Fragment-based optimization of small molecule CXCL12 inhibitors for antagonizing the CXCL12/CXCR4 interaction." Current topics in medicinal chemistry 12.24 (2012): 2727-2740.
Ziarek, Joshua, et al. "Sulfotyrosine recognition as marker for druggable sites in the extracellular space." International journal of molecular sciences 12.6 (2011): 3740-3756.
Dombkowski, Alan A. "Disulfide by Design™: a computational method for the rational design of disulfide bonds in proteins." Bioinformatics 19.14 (2003): 1852-1853.
Gozansky, Elliott K., et al. "Mapping the binding of the N-terminal extracellular tail of the CXCR4 receptor to stromal cell-derived factor-1α." Journal of molecular biology 345.4 (2005): 651-658.
Simpson, Levi S., et al. "Regulation of chemokine recognition by site-specific tyrosine sulfation of receptor peptides." Chemistry & biology 16.2 (2009): 153-161.
Zhu, John Z., et al. "Tyrosine sulfation influences the chemokine binding selectivity of peptides derived from chemokine receptor CCR3." Biochemistry 50.9 (2011): 1524-1534.
Tan, Joshua HY, et al. "Tyrosine sulfation of chemokine receptor CCR2 enhances interactions with both monomeric and dimeric forms of the chemokine monocyte chemoattractant protein-1 (MCP-1)." Journal of Biological Chemistry 288.14 (2013): 10024-10034.
Wells, James A., and Christopher L. McClendon. "Reaching for high-hanging fruit in drug discovery at protein-protein interfaces." Nature 450.7172 (2007): 1001-1009.
Nielsen, P. F., Steffen Bak, and B. Vandahl. "Characterization of tyrosine sulphation in rFVIII (turoctocog alfa) expressed in CHO and HEK-293 cells." Haemophilia 18.5 (2012).
Duma, Luminita, et al. "Recognition of RANTES by extracellular parts of the CCR5 receptor." Journal of molecular biology 365.4 (2007): 1063-1075.
Pawson, Tony, and Piers Nash. "Assembly of cell regulatory systems through protein interaction domains." science 300.5618 (2003): 445-452.
Edwards, Richard J., Norman E. Davey, and Denis C. Shields. "SLiMFinder: a probabilistic method for identifying over-represented, convergently evolved, short linear motifs in proteins." PloS one 2.10 (2007): e967.
Machida, Kazuya, and Bruce J. Mayer. "The SH2 domain: versatile signaling module and pharmaceutical target." Biochimica et Biophysica Acta (BBA)-Proteins and Proteomics 1747.1 (2005): 1-25.
Vidler, Lewis R., et al. "Druggability analysis and structural classification of bromodomain acetyl-lysine binding sites." Journal of medicinal chemistry 55.17 (2012): 7346.
Herold, J. Martin, et al. "Drug discovery toward antagonists of methyl-lysine binding proteins." Curr Chem Genomics 5 (2011): 51-61.
Stone, Martin J., et al. "Tyrosine sulfation: an increasingly recognised post-translational modification of secreted proteins." New biotechnology 25.5 (2009): 299-317.
Peterson, Francis C., and Brian F. Volkman. "Diversity of polyproline recognition by EVH1 domains." Frontiers in bioscience (Landmark edition) 14 (2009): 833.
Monigatti, Flavio, et al. "The Sulfinator: predicting tyrosine sulfation sites in protein sequences." Bioinformatics 18.5 (2002): 769-770.
Liu, Justin, et al. "Tyrosine sulfation is prevalent in human chemokine receptors important in lung disease." American journal of respiratory cell and molecular biology 38.6 (2008): 738-743.
Keller, Rochus. "The computer aided resonance assignment tutorial." Cantina, Goldau 15 (2004).
Ziarek, Joshua J., et al. "Binding site identification and structure determination of protein-ligand complexes by NMR." Methods in enzymology 493 (2011): 241.
Ziarek et al., "Sulfopeptide probes of the CXCR4/CSCL12 interface reveal oligomer-specific contacts and chemokine allostery," ACS Chem Biol. 8:1955-1963, 2013.
NCBI GenBank Accession No. P48061, Feb. 1, 1996.
Leukemia, http://medical-dictionary.thefreedictionary.com/leukemia; accessed Apr. 25, 2012.
Tanaka et al. (2012, Expert Opin. Pharmacol. 13: 815-828).

\* cited by examiner

FIG. 2A
MEGISIYTSDNYTEEMGSGDYDSMKEPAFREENANFNK (SEQ ID NO:3)
FIG. 2B
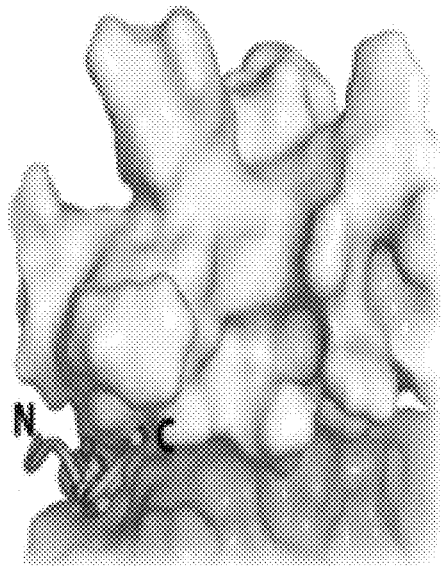
FIG. 2C

CXCL12₃

CXCL12₁

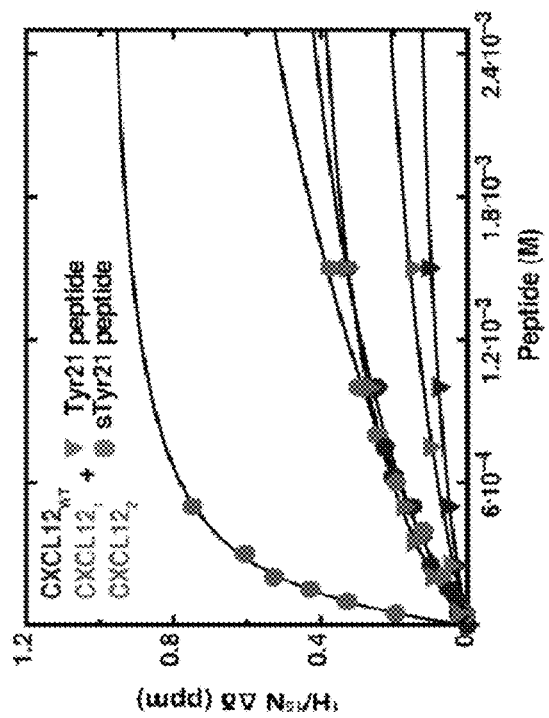
FIG. 3A
FIG. 3B
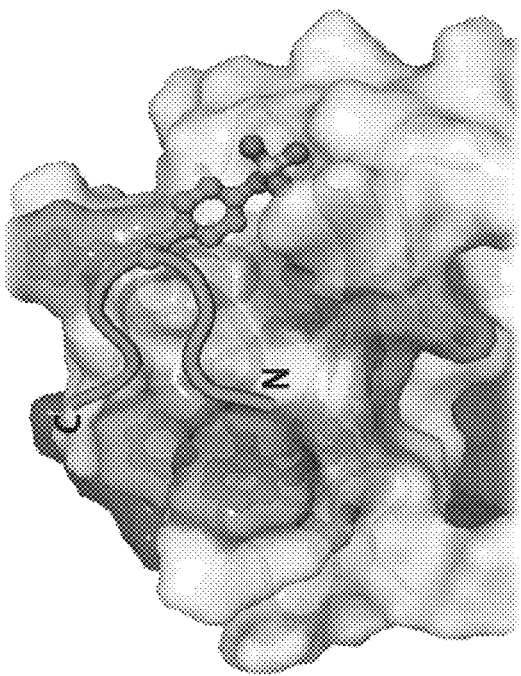
FIG. 3C
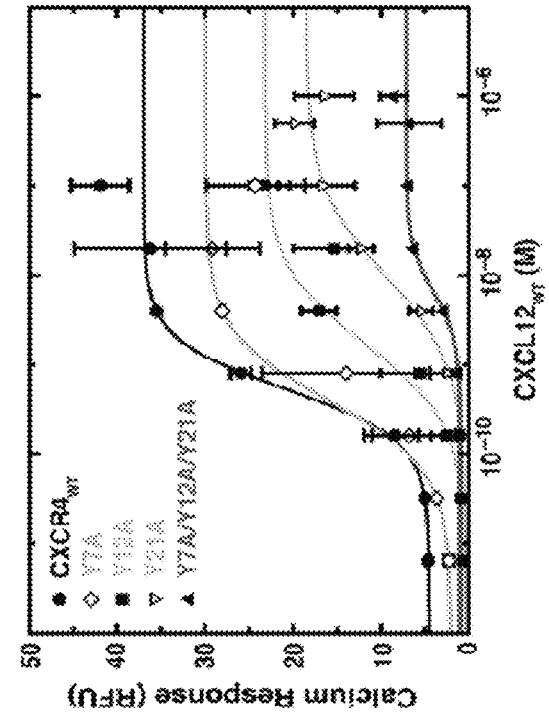
FIG. 3D
| CXCR4 variant | EC$_{50}$ (nM) | Max Response (RFU) |
|---|---|---|
| CXCR4$_{WT}$ | 0.5 ± 0.1 | 37.0 ± 0.6 |
| Y7A | 0.4 ± 0.3 | 29.9 ± 3.4 |
| Y12A | 1.7 ± 0.7* | 23.2 ± 1.8* |
| Y21A | 9.9 ± 3.0* | 18.6 ± 1.1* |
| Y7A/Y12A/Y21A | 6.6 ± 0.6* | 7.1 ± 0.3* |

| (SEQ ID NO:4) | (SEQ ID NO:5) |
| :---: | :---: |
| $_{18}$SGDsYDSM$_{24}$ | $_{18}$SGDYDSM$_{24}$ |

CXCL12$_{WT}$

CXCL12$_2$

CXCL12$_1$ (SEQ ID NO:6)      SEQ ID NO:7)
$_9$SDNsYTEE$_{15}$      $_9$SDNYTEE$_{15}$

CXCL12$_{WT}$

CXCL12$_2$

CXCL12$_1$

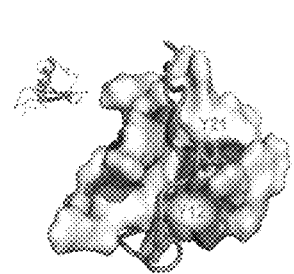 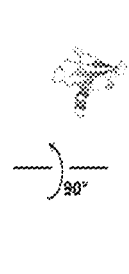 
FIG. 11A  FIG. 11B  FIG. 11C
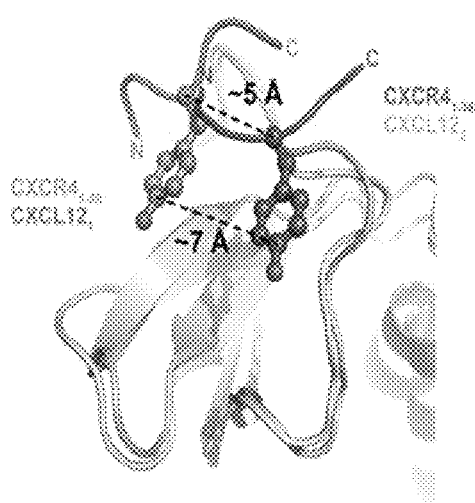 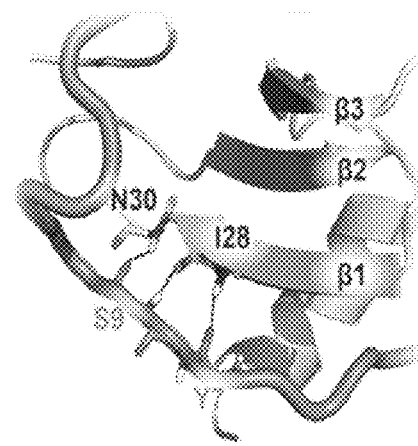
FIG. 11D  FIG. 11E 1:1 complex 2:2 complex Amino Acid Residue (SEQ ID NO:3)

FIG. 17A
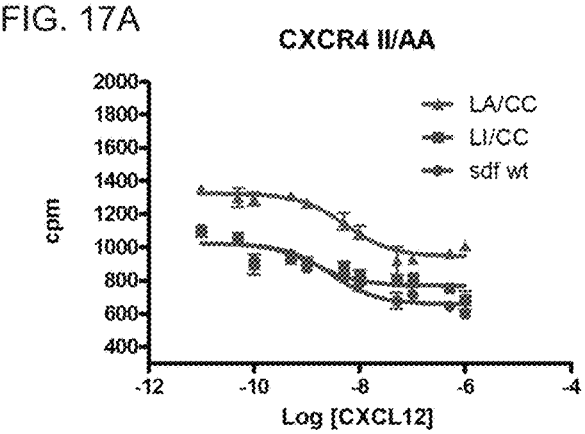
FIG. 17B
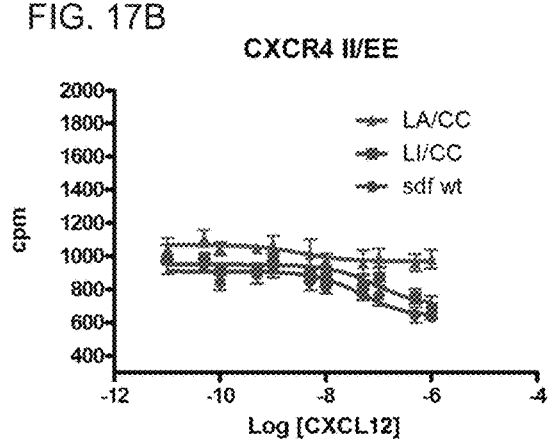
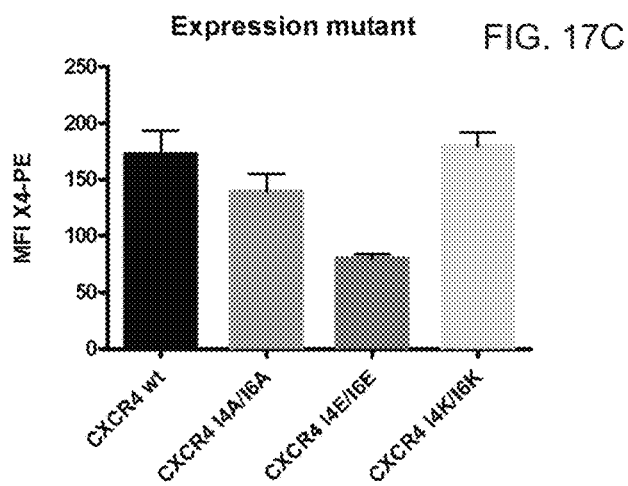
FIG. 17C

FIG. 19A
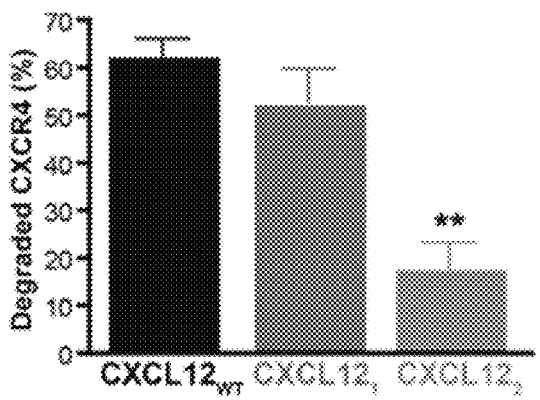
FIG. 19B
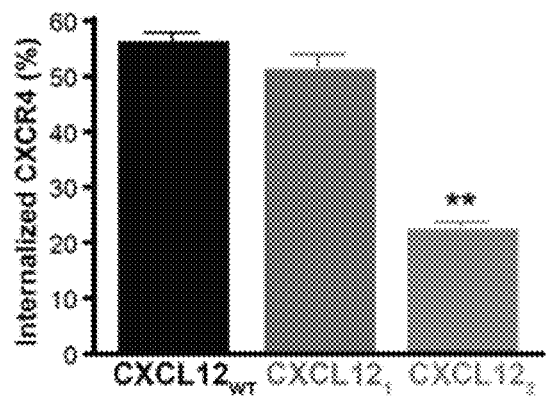
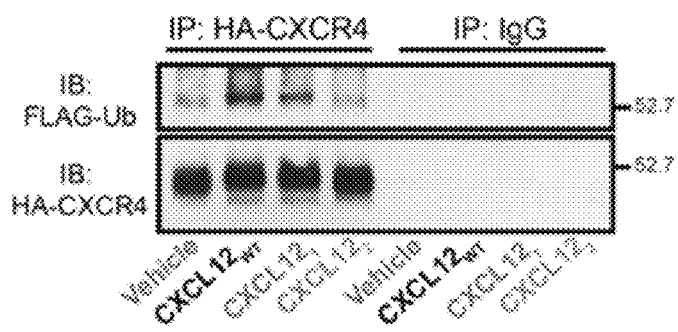
FIG. 19C
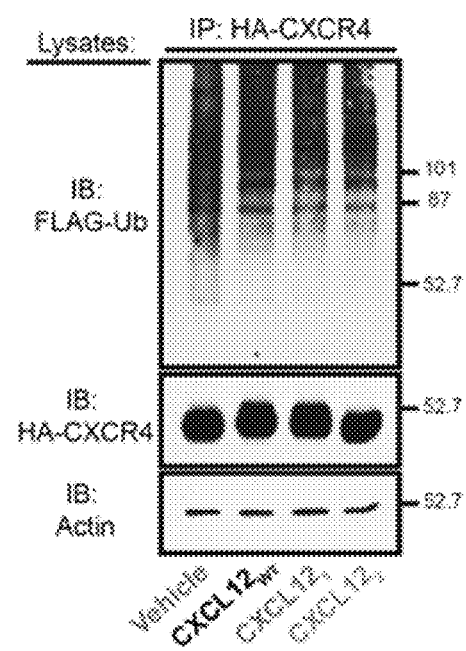
FIG. 19D

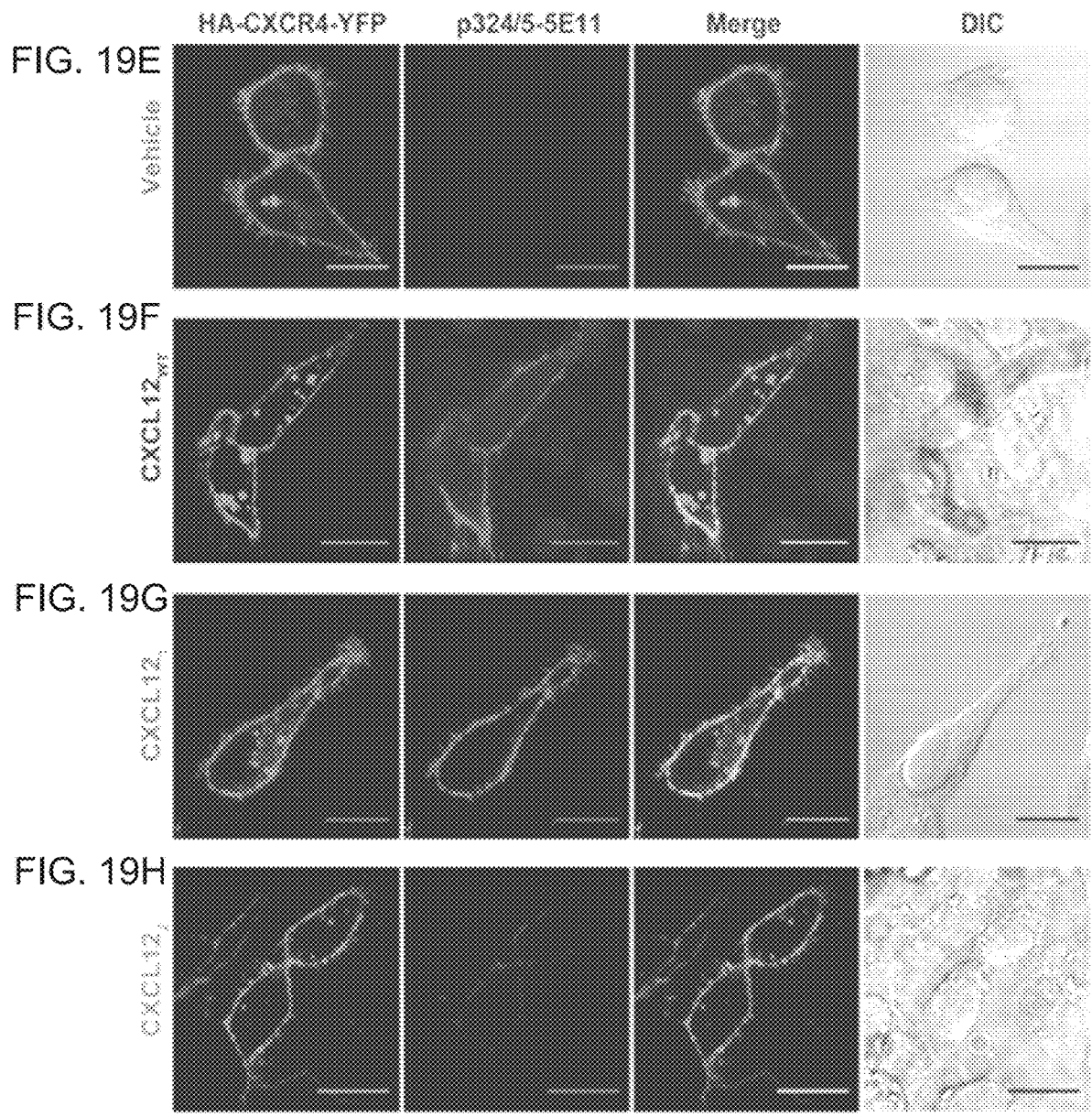

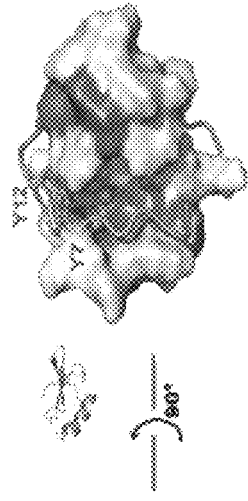
FIG. 20A
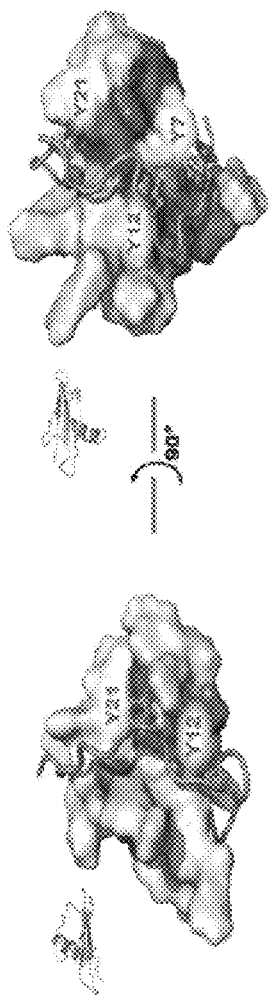
FIG. 20B
FIG. 20C
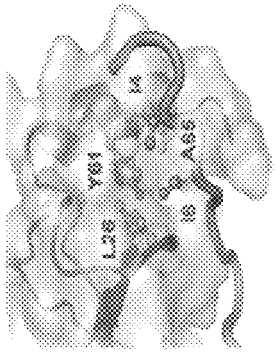
FIG. 20D
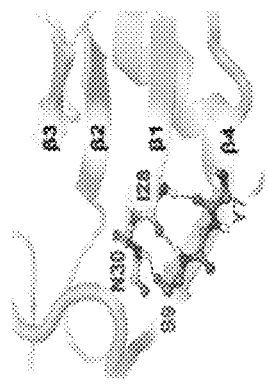
FIG. 20E
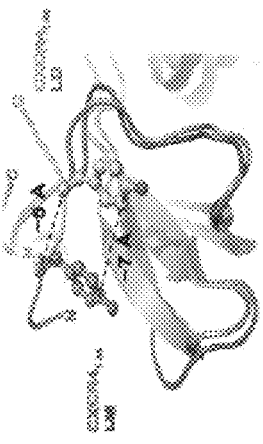
FIG. 20F
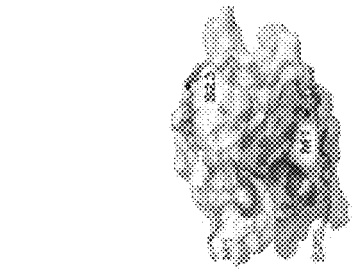
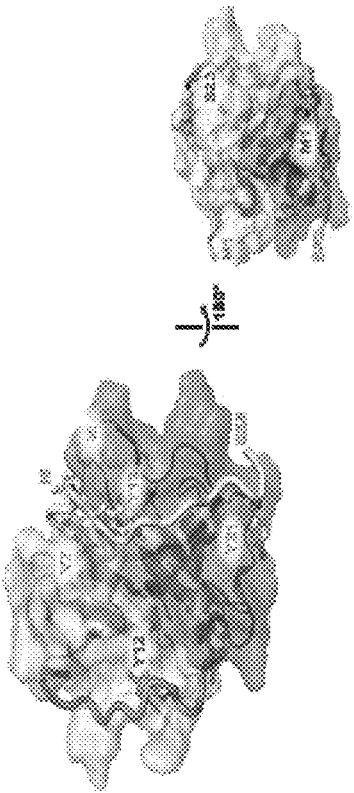
FIG. 20H
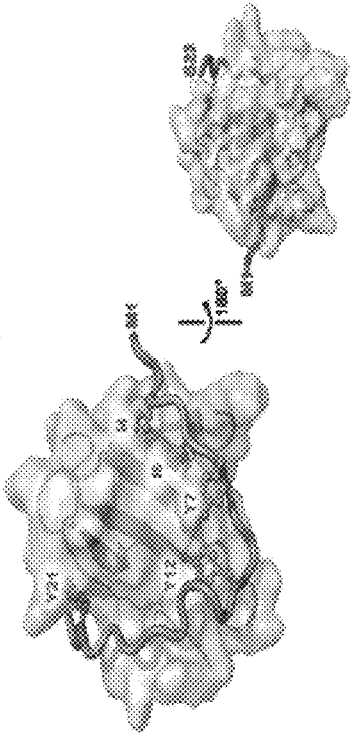
FIG. 20G (SEQ ID NO:3)

(SEQ ID NO:3)

SEQUENCE LISTING

<160> NUMBER OF SEQ ID NOS: 10

<210> SEQ ID NO 1
<211> LENGTH: 68
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 68
<212> TYPE: PRT
<213> ORGANISM: Artificial Sequence
<220> FEATURE:
<223> OTHER INFORMATION: synthetic

<400> SEQUENCE: 2

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

```
Val Cys Ile Asp Pro Lys Cys Lys Trp Cys Gln Glu Tyr Leu Glu Lys
 50                  55                  60

Ala Leu Asn Lys
 65

<210> SEQ ID NO 3
<211> LENGTH: 38
<212> TYPE: PRT
<213> ORGANISM: Homo sapiens

<400> SEQUENCE: 3

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Ala Phe Arg Glu Glu
                20                  25                  30

Asn Ala Asn Phe Asn Lys
         35

<210> SEQ ID NO 4
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Sulfated tyrosine

<400> SEQUENCE: 4

Ser Gly Asp Tyr Asp Ser Met
 1               5

<210> SEQ ID NO 5
<211> LENGTH: 7
<212> TYPE: PRT
<213> ORGANISM: Homo sapiens

<400> SEQUENCE: 5

Ser Gly Asp Tyr Asp Ser Met
 1               5

<210> SEQ ID NO 6
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Sulfated tyrosine

<400> SEQUENCE: 6

Ser Asp Asn Tyr Thr Glu Glu
 1               5

<210> SEQ ID NO 7
<211> LENGTH: 7
<212> TYPE: PRT
<213> ORGANISM: Homo sapiens

<400> SEQUENCE: 7

Ser Asp Asn Tyr Thr Glu Glu
 1               5
```

```
<210> SEQ ID NO 8
<211> LENGTH: 7
<212> TYPE: PRT
<213> ORGANISM: Homo sapiens

<400> SEQUENCE: 8

Ile Ser Ile Tyr Thr Ser Asp
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Sulfated tyrosine

<400> SEQUENCE: 9

Ile Ser Ile Tyr Thr Ser Asp
1               5

<210> SEQ ID NO 10
<211> LENGTH: 6
<212> TYPE: PRT
<213> ORGANISM: Homo sapiens

<400> SEQUENCE: 10

Arg Phe Phe Glu Ser His
1               5
```

METHODS OF TREATING INFLAMMATION WITH MONOMERIC CXCL12 PEPTIDE

CROSS-REFERENCE TO RELATED APPLICATIONS

This application is a continuation of U.S. application Ser. No. 15/874,476 filed on Jan. 18, 2018, which is a continuation of U.S. application Ser. No. 14/736,535, filed Jun. 11, 2015 now U.S. Pat. No. 9,908,923, which claims the benefit of U.S. Provisional Patent Application Ser. No. 62/010,655 filed on Jun. 11, 2014, each of which is incorporated by reference for all purposes.

STATEMENT REGARDING FEDERALLY FUNDED RESEARCH AND DEVELOPMENT

This invention was made with government support under grants R01AI058072 (BFV), R01GM097381 (BFV), R56AI063325 (BFV), U01GM094612 (TMH), and R01GM081763 (TMH) awarded by the National Institutes of Health. The government has certain rights in the invention.

STATEMENT REGARDING SEQUENCING LISTING

A Sequence Listing accompanies this application and is submitted as an ASCII text file of the sequence listing named "2020-01-17_650053-00665_SEQ_LISTING.txt" which is 3,394 t in size and was created on Jan. 17, 2020. The sequence listing is electronically submitted via EFS-Web with the application and is incorporated herein by reference in its entirety.

FIELD OF THE INVENTION

This invention relates generally to a $CXCL12_1$ monomer, pharmaceutical compositions thereof, and methods of using the $CXCL12_1$ monomer in the treatment of cancer, autoimmune and inflammatory disease, and HIV/AIDS.

BACKGROUND OF THE INVENTION

Chemokines are small soluble proteins that stimulate chemotactic cell migration via activation of a G protein-coupled receptor (GPCR). In addition to their vital roles in inflammation, wound healing, and stem cell homing, chemokines also contribute to many pathologies including autoimmune diseases and cancer. Interactions of the chemokine CXCL12 (stromal cell-derived factor-1/SDF-1) and its receptor CXCR4 are particularly well studied because of their participation in neurogenesis, cardiogenesis, angiogenesis, myocardial infarction/reperfusion injury, HIV infection, and numerous carcinomas and sarcomas.

Chemokine receptor recognition and activation occurs via a two-step, two-site process. First, the CXCR4 extracellular N-terminus binds to CXCL12 (site 1). The N-terminus of CXCL12 then recognizes the receptor transmembrane domain and activates signaling (site 2). In addition to one site of O-linked glycosylation, CXCR4 possesses three tyrosine residues (Tyr7, Tyr12, and Tyr21) in the N-terminus capable of being O-sulfated in the Golgi apparatus. Mutational studies suggested that sulfation of Tyr21 enhances the binding of wild type CXCL12 ($CXCL12_{WT}$, SEQ ID NO:1), but the level of sulfation at each tyrosine and their relative contributions to chemokine recognition were not quantified. Consistent with studies of the full-length CXCR4 receptor expressed in cells, sequential sulfation of a peptide comprising residues 1-38 ($CXCR4_{1-38}$) enhanced the affinity for CXCL12. Full-length chemokine receptors CCR2b, CCR5, CCR8, CXCR3, and $CX_3CR1$ have since been shown to also exhibit increased ligand binding affinity upon tyrosine sulfation; replacement of tyrosines with phenylalanine residues resulted in 10 to 200-fold decreases in affinity and, in some cases, undetectable binding demonstrating the importance of sulfotyrosine recognition in chemokine signaling.

While most chemokines form dimers or other oligomers, receptor activation is typically restricted to the monomeric ligand. However, structure-function studies of CXCL12 using preferentially monomeric ($CXCL12_{H25R}$) and constitutively dimeric ($CXCL12_2$) variants demonstrated that dimerization converts CXCL12 into a partial CXCR4 agonist that potently inhibits chemotaxis. As a CXCR4 ligand that stimulates intracellular calcium flux but fails to activate F-actin polymerization or β-arrestin recruitment, the $CXCL12_2$ dimer causes a type of 'cellular idling' that can block metastatic tumor formation in animal models for colorectal cancer and melanoma. Differences in how the CXCR4 N-terminus is recognized by CXCL12 monomers and dimers may contribute to their distinct receptor activation profiles (26). For instance, in the NMR structure of the $CXCL12_2$:$CXCR4_{1-38}$ complex the receptor fragment wraps around both subunits of the CXCL12 dimer, placing sulfotyrosine 12 (sTyr12) and sTyr21 in distinct sites on one subunit while sTyr7 occupies a cleft at the dimer interface that would not exist in a CXCL12 monomer. In concordance with this structural model, it was observed that $CXCR4_{1-38}$ binding promotes CXCL12 dimerization. However, individual contributions of CXCR4 sulfotyrosines to the affinity and specificity of CXCL12 recognition and their impact on the monomer-dimer equilibrium remain unknown.

Site 1 contacts that contribute most to binding are potential targets for development of novel chemokine probes and antagonists. For example, we recently demonstrated that the sTyr21 binding pocket of CXCL12 can be targeted for inhibition by small molecule ligands that block CXCR4-mediated calcium signaling and chemotaxis (29, 30). This appears to be a conserved binding site, suggesting that sulfotyrosine-guided drug discovery may be a general strategy for targeting the chemokine family and other protein-protein interactions in the extracellular space.

Accordingly, there is a current need for cost-effective pharmaceutical agents and treatment methods for treating various conditions including autoimmune or inflammation disorders, immune suppression conditions, infections, blood cell deficiencies, cancers and other described conditions and to mobilize stem cells by manipulating and controlling CXCL12 and CXCR4.

SUMMARY OF THE INVENTION

The present invention provides a $CXCL12_1$ peptide. In one embodiment, the $CXCL12_1$ peptide has been engineered to resist peptide-induced dimerization by maintaining steric repulsion of the chemokine helix. Specifically, in one embodiment, the $CXCL12_1$ peptide (SEQ ID NO:2) comprises L55C and I58C substitutions as compared to the wild-type peptide (SEQ ID NO:1).

In other embodiments, the invention provides a composition comprising a $CXCL12_1$ peptide, wherein the peptide comprises L55C and I58C substitutions, and a pharmaceutically acceptable carrier or diluent.

In other embodiments, the invention provides a method of treating an autoimmune disease in a subject comprising administering to the subject a therapeutically effective amount of a composition comprising a $CXCL12_1$ peptide.

In other embodiments, the invention provides a method of treating a solid tumor in a subject comprising administering to the subject a therapeutically effective amount of a composition comprising a $CXCL12_1$ peptide.

In other embodiments, the invention provides a method of inhibiting angiogenesis in a subject by administering to the subject a therapeutically effective amount of a composition comprising a $CXCL12_1$ peptide.

In other embodiments, the invention provides a method of treating cancer in a subject comprising administering to the subject a therapeutically effective amount of a composition comprising a $CXCL12_1$ peptide.

In other embodiments, the invention provides a method of treating HIV/AIDS in a subject comprising administering to the subject a therapeutically effective amount of a composition comprising a $CXCL12_1$ peptide.

In other embodiments, the invention provides a method of inducing apoptosis in a subject comprising administering to the subject a therapeutically effective amount of a composition comprising a $CXCL12_1$ peptide.

In other embodiments, the invention provides a method of treating leukemia in a subject comprising administering to the subject a therapeutically effective amount of a composition comprising a $CXCL12_1$ peptide, wherein the leukemia cells express CXCR4.

In other embodiments, the invention provides a method of inhibiting migration of cancer cells in a subject comprising administering to the subject a therapeutically effective amount of a composition comprising a $CXCL12_1$ peptide, wherein the cancer cells express CXCR4.

In other embodiments, the invention provides a method of inhibiting migration of leukemia cells in a subject comprising administering to the subject a therapeutically effective amount of a composition comprising a $CXCL12_1$ peptide, wherein the leukemia cells express CXCR4. In one embodiment, the leukemia cells are selected from the group consisting of leukemia, lymphoma and myeloma.

In other embodiments, the invention provides a kit comprising a $CXCL12_1$ peptide, a pharmaceutically acceptable carrier or diluent, and instructional material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A. Chemical shift perturbations of CXCR4 sulfopeptides designed from the extracellular N-terminus. The residues corresponding to the sTyr7 (cyan), sTyr12 (wheat), and sTyr21 (green) heptapeptides are indicated on the CXCR4 N-terminus amino acid sequence. The previously defined positions of sTyr7.

FIG. 2B. The residues corresponding to the sTyr7 (cyan), sTyr12 (wheat), and sTyr21 (green) heptapeptides are indicated on the CXCR4 N-terminus amino acid sequence. The previously defined positions of sTyr12.

FIG. 2C. The previously defined positions of sTyr21.

FIG. 3A. Sulfation of Tyr21 improves sulfopeptide binding affinity and modulates full-length receptor activity. The largest chemical shift perturbations (orange) are consistent with the putative sTyr21 sulfopeptide (green) binding site on $CXCL12_2$ (PDB ID 2K05).

FIG. 3B. Chemical shift perturbations induced by sulfated and unsulfated peptides were fitted to a quadratic binding equation to yield $K_d$ values. The sTyr21 sulfopeptide (circles) bound $CXCL12_{WT}$ with $K_d$=1.8±0.2 mM (black), $CXCL12_1$ with $K_d=1.6\pm0.2$ mM (blue) and $CXCL12_2$ with $K_d=211\pm23$ µM (red). The Tyr21 peptide (triangles) bound $CXCL12_{WT}$ with $K_d=2.7\pm0.5$ mM (black), $CXCL12_1$ with $K_d=1.5\pm0.4$ mM (blue) and $CXCL12_2$ with $K_d=831\pm137$ µM (red).

FIG. 3C. The calcium response of FLAG-tagged CXCR4 variants was measured as a function of $CXCL12_{WT}$ concentration. Data are representative of two experiments each performed with three replicates.

FIG. 3D. Four parameter fits yielded each CXCR4 variants $EC_{50}$ and maximum calcium response. CXCR4 variants with $EC_{50}$ or maximum calcium response values more than three standard deviations from the mean $CXCR4_{WT}$ quantities are indicated with an asterisk.

FIG. 11A. NMR structure of $CXCL12_1$ in complex with $CXCR4_{1-38}$. Surface representation of $CXCL12_1$ (gray) in complex with $CXCR4_{1-38}$ (orange). For visual clarification, $CXCR4_{1-38}$ tyrosine residues are represented by ball and stick, and only $CXCR4_{1-38}$ residues 1-28 are displayed. Previously published $CXCL12_1$ chemical shift perturbations induced by $CXCR4_{1-38}$ are mapped onto the surface in blue.

FIG. 11B. NMR structure of $CXCL12_1$ in complex with $CXCR4_{1-38}$. Surface representation of $CXCL12_1$ (gray) in complex with $CXCR4_{1-38}$ (orange). For visual clarification, $CXCR4_{1-38}$ tyrosine residues are represented by ball and stick, and only $CXCR4_{1-38}$ residues 1-28 are displayed. Previously published $CXCL12_1$ chemical shift perturbations induced by $CXCR4_{1-38}$ are mapped onto the surface in blue.

FIG. 11C. NMR structure of $CXCL12_1$ in complex with $CXCR4_{1-38}$. Surface representation of $CXCL12_1$ (gray) in complex with $CXCR4_{1-38}$ (orange). For visual clarification, $CXCR4_{1-38}$ tyrosine residues are represented by ball and stick, and only $CXCR4_{1-38}$ residues 1-28 are displayed. Previously published $CXCL12_1$ chemical shift perturbations induced by $CXCR4_{1-38}$ are mapped onto the surface in blue.

FIG. 11D. The CXCL12$_1$·CXCR4$_{1-38}$ NMR structure (gray and orange) was aligned to the CXCL12$_2$:CXCR4$_{1-38}$ NMR structure (yellow and blue; PDB 2K04) with a backbone RMSD=1.41 Å. The position of Tyr21 C$^\alpha$ and C$^\zeta$ are translated by an average of 5 Å and 7 Å, respectively.

FIG. 11E. Representation of beta-sheet hydrogen bond network between CXCL12$_1$ (gray) and CXCR4$_{1-38}$ (orange) Hydrogen bonds are indicated with black dashed lines.

FIGS. 17A-C. CXCR4 Ile4 and Ile6 are critical for receptor binding and activation.

FIG. 19A. CXCL12 tertiary structure controls CXCR4 fate and function. HeLa cells were stimulated with vehicle or 80 ng/ml CXCL12 variants for 2 h. Endogenous CXCR4 receptor levels were determined by SDS-PAGE followed by immunoblotting with an anti-CXCR4 antibody. Bars represent the mean CXCR4 degraded±S.E.M., n=3.

FIG. 19B. HeLa cells were stimulated with vehicle or 80 ng/ml CXCL12 variants for 20 min. Cells were stained with a PE-conjugated anti-CXCR4 antibody or isotype control antibody, and endogenous CXCR4 surface expression was analyzed by flow cytometry. Bars represent the mean CXCR4 internalized±S.E.M., n=3.

FIG. 19C. HEK293 cells stably expressing HA-CXCR4 were stimulated with vehicle or 80 ng/ml CXCL12 variants for 30 min. HA-CXCR4 was immunoprecipitated using an anti-HA polyclonal antibody and samples were analyzed by immunoblotting to detect incorporated FLAG-ubiquitin. Shown are representative blots from one of three independent experiments performed.

FIG. 19D. HEK293 cells stably expressing HA-CXCR4 were stimulated with vehicle or 80 ng/ml CXCL12 variants for 30 min. HA-CXCR4 was immunoprecipitated using an anti-HA polyclonal antibody and samples were analyzed by immunoblotting to detect incorporated FLAG-ubiquitin. Shown are representative blots from one of three independent experiments performed.

FIG. 19E. HeLa cells transiently transfected with HA-CXCR4-YFP were stimulated for 30 min with vehicle or 80 ng/ml.

FIG. 19F. HeLa cells transiently transfected with HA-CXCR4-YFP were stimulated for 30 min with CXCL12$_{WT}$.

FIG. 19G. HeLa cells transiently transfected with HA-CXCR4-YFP were stimulated for 30 min with CXCL12$_1$.

FIG. 19H. HeLa cells transiently transfected with HA-CXCR4-YFP were stimulated for 30 min with CXCL12$_2$. Cells were fixed, permeabilized and stained with an anti-CXCR4-p324/5 monoclonal antibody and analyzed by confocal immunofluorescence microscopy. Shown in green is YFP-tagged CXCR4 (far left panels) and shown in red is staining for phosphorylated CXCR4 Ser324 and Ser325 (middle left panels). Co-localization between YFP-tagged CXCR4 and phosphorylated CXCR4 appear yellow in the merge (middle right panels). Differential interference contrast (DIC) images are also shown (far right panels). Shown are representative micrographs from three independent experiments. Bars, 20 μm.

FIG. 20A. NMR structure of CXCL12$_1$ in complex with CXCR4$_{1-38}$. Surface representation of CXCL12$_1$ (gray) in complex with CXCR4$_{1-38}$ (orange). For visual clarification, CXCR4$_{1-38}$ tyrosine residues are represented by ball and stick, and only CXCR4$_{1-38}$ residues 1-28 are displayed. Previously published CXCL12$_1$ chemical shift perturbations induced by CXCR4$_{1-38}$ are mapped onto the surface in blue.

FIG. 20B. NMR structure of CXCL12$_1$ in complex with CXCR4$_{1-38}$. Surface representation of CXCL12$_1$ (gray) in complex with CXCR4$_{1-38}$ (orange). For visual clarification, CXCR4$_{1-38}$ tyrosine residues are represented by ball and stick, and only CXCR4$_{1-38}$ residues 1-28 are displayed. Previously published CXCL12$_1$ chemical shift perturbations induced by CXCR4$_{1-38}$ are mapped onto the surface in blue.

FIG. 20C. NMR structure of CXCL12$_1$ in complex with CXCR4$_{1-38}$. Surface representation of CXCL12$_1$ (gray) in complex with CXCR4$_{1-38}$ (orange). For visual clarification, CXCR4$_{1-38}$ tyrosine residues are represented by ball and stick, and only CXCR4$_{1-38}$ residues 1-28 are displayed. Previously published CXCL12$_1$ chemical shift perturbations induced by CXCR4$_{1}$_38 are mapped onto the surface in blue.

FIG. 20D. The CXCL12$_1$:CXCR4$_{1-38}$ NMR structure (gray and orange) was aligned to the CXCL12$_2$:CXCR4$_{1-38}$ NMR structure (yellow and blue; PDB 2K04) with a backbone RMSD=1.41 Å. The position of Tyr21 C$^\alpha$ and C$^\zeta$ are translated by an average of 5 Å and 7 Å, respectively.

FIG. 20E. Representation of β-sheet hydrogen bond network between CXCL12$_1$ (gray) and CXCR4$_{1-38}$ (orange) Hydrogen bonds are indicated with black dashed lines.

FIG. 20F. CXCR4$_{1-38}$ residues Ile4 and Ile6 pack into a cleft against residues CXCL12$_1$ residues Leu26 and Tyr61.

FIG. 20G. Comparison of the CXCL12$_1$.CXCR4$_{1-38}$ complex NMR structures.

FIG. 20H. Comparison of the CXCL12$_2$:CXCR4$_{1-38}$ complex NMR structures.

DETAILED DESCRIPTION OF THE INVENTION

Figure 1A:
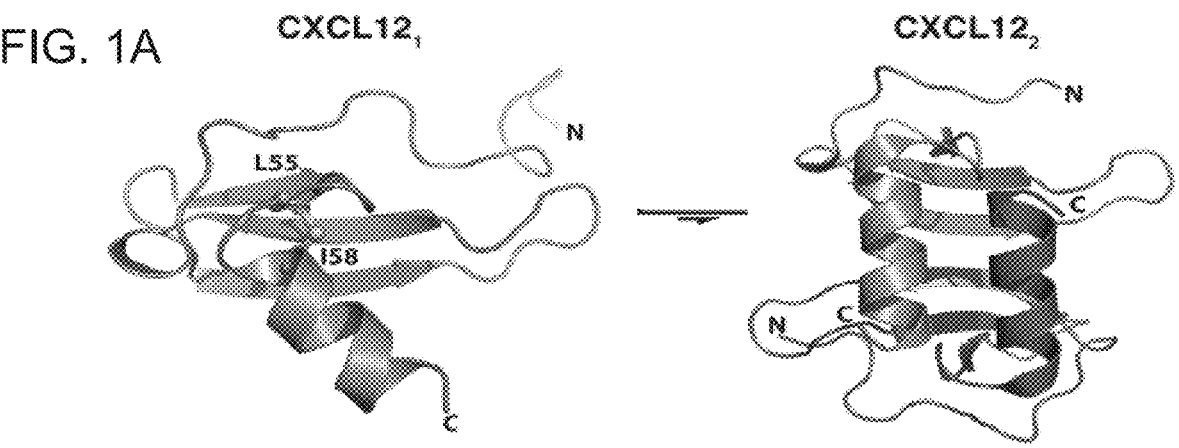
FIG. 1A. $CXCL12_1$ and $CXCL12_2$ have discrete $CXCR4_{1-38}$ binding sites. The CXCL12 NMR structure (PDB ID 1SDF) solved in acetate (pH 4.9) was used to identify and model the I55C/L58C mutations for disulfide formation (yellow). Dimerization is inhibited when the helix is constrained to an acute angle relative to the β-sheet.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

I. THE INVENTION

The present invention provides a constitutively monomeric CXCL12 variant (CXCL12$_1$) engineered to resist peptide-induced dimerization by maintaining steric repulsion of the chemokine helix. Six short CXCR4 peptides, centered on Tyr7, Tyr12, or Tyr21, were synthesized to study the contributions of individual sulfotyrosines in peptide binding and specificity. Peptides were titrated into CXCL12$_{WT}$, CXCL12$_2$(a consitutatively dimeric variant of CXCL12 containing L36C/A65C mutations), or CXCL12$_1$ and the interaction was monitored by 2D NMR. While sulfopeptides encompassing sTyr7 and sTyr12 interacted nonspecifically, an unsulfated Tyr7 peptide induced a new set of chemical shift perturbations in the CXCL12 monomer that were also observed upon binding of the intact CXCR4$_{1-38}$ N-terminal domain. In contrast, the Tyr21 peptides bound specifically to the sTyr21 recognition site in all three CXCL12 variants, but exhibited a significantly higher affinity for CXCL12$_2$. The sTyr21 sulfopeptide correspondingly increased the CXCL12 dimerization affinity by eight-fold, revealing an allosteric coupling between the sulfotyrosine binding site and CXCL12 dimerization.

Tyrosine sulfation is a post-translational modification that enhances protein-protein interactions and may identify druggable sites in the extracellular space. The G protein-coupled receptor CXCR4 is a prototypical example with three potential sulfation sites at positions 7, 12 and 21. Each receptor sulfotyrosine participates in specific contacts with its chemokine ligand in the structure of a soluble, dimeric CXCL12:CXCR4(1-38) complex, but their relative importance for CXCR4 binding and activation by the monomeric chemokine remains undefined. NMR titrations with short sulfopeptides showed that the tyrosine motifs of CXCR4 varied widely in their contributions to CXCL12 binding affinity and site specificity. Whereas the Tyr21 sulfopeptide bound the same site as in previously solved structures, the Tyr7 and Tyr12 sulfopeptides interacted nonspecifically. Surprisingly, the unsulfated Tyr7 peptide occupied a hydrophobic site on the CXCL12 monomer that is inaccessible in the CXCL12 dimer.

Functional analysis of CXCR4 mutants validated the relative importance of individual CXCR4 sulfotyrosine modifications (Tyr21>Tyr12 >Tyr7) for CXCL12 binding and receptor activation. Biophysical measurements also revealed a cooperative relationship between sulfopeptide binding at the Tyr21 site and CXCL12 dimerization, the first example of allosteric behavior in a chemokine. Future ligands that occupy the sTyr21 recognition site may act as both competitive inhibitors of receptor binding and allosteric modulators of chemokine function. Together, our data suggests that sulfation does not ubiquitously enhance complex affinity and that distinct patterns of tyrosine sulfation could encode oligomer selectivity—implying another layer of regulation for chemokine signaling.

CXCL12$_1$ monomer. In one embodiment, the invention provides a constitutively monomeric CXCL12 variant, termed CXCL12$_1$, engineered to resist peptide-induced dimerization by maintaining steric repulsion of the chemokine helix. Specifically, the monomeric CXCL12 peptide of the present invention has been modified to exhibit at least L55C and I58C substitutions (SEQ ID NO:2). Other substitutions are also contemplated by this invention.

In one embodiment, the CXCL12$_1$ monomer of the present invention comprises a substantially pure preparation. By "substantially pure" we mean a preparation in which more than 90%, e.g., 95%, 98% or 99% of the preparation is that of the CXCL12$_1$ monomer.

The CXCL12$_1$ monomer of the present invention could also be incorporated into a larger protein or attached to a fusion protein that may function to increase the half life of the monomer in vivo or be used as a mechanism for time released and/or local delivery (U.S. Patent Appn. No. 20060088510). In another embodiment, the invention provides an isolated CXCL12$_1$ monomer as described above. By "isolated" we mean a nucleic acid sequence that is identified and separated from at least one component or contaminant with which it is ordinarily associated. An isolated nucleic acid is present in a form or setting that is different from that in which it is found in nature. In contrast, non-isolated nucleic acids such as DNA and RNA are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, an isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

The CXCL12$_1$ monomer of the present invention can be prepared by standard techniques known in the art. The peptide component of CXCL12 is composed, at least in part, of a peptide, which can be synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York (1992). Automated peptide synthesizers are commercially available (e.g., Advanced ChemTech Model 396; Milligen/Biosearch 9600). Additionally, one or more modulating groups can be attached to the CXCL12 derived peptidic component by standard methods, such as by using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)). Exemplary syntheses of preferred CXCL12$_1$ monomer according to the present invention are described further in the Examples below.

Peptides of the invention may be chemically synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York, (1992) (all of which are incorporated herein by reference).

In another aspect of the invention, peptides may be prepared according to standard recombinant DNA techniques using a nucleic acid molecule encoding the peptide. A nucleotide sequence encoding the peptide can be determined using the genetic code and an oligonucleotide molecule having this nucleotide sequence can be synthesized by standard DNA synthesis methods (e.g., using an automated DNA synthesizer). Alternatively, a DNA molecule encoding a peptide compound can be derived from the natural precursor protein gene or cDNA (e.g., using the polymerase chain reaction (PCR) and/or restriction enzyme digestion) according to standard molecular biology techniques.

CXCL12$_1$ Pharmaceutical Compositions. In another embodiment, the invention provides a composition comprising a substantially pure CXCL12$_1$ monomer of the present invention, and a pharmaceutically acceptable carrier. By "pharmaceutically acceptable carrier" we mean any and all solvents, dispersion media, coatings, antibacterial and antifungal agents, isotonic and absorption delaying agents, and the like that are physiologically compatible. In one embodiment, the carrier may be suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, membrane nanoparticle or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, such as, monostearate salts and gelatin.

Moreover, the CXCL12$_1$ monomer of the present invention can be administered in a time-release formulation, such as in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. CXCR4 agonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The $CXCL12_1$ monomer of the present invention also may be formulated with one or more additional compounds that enhance the solubility of the $CXCL12_1$ monomer.

Administration. The $CXCL12_1$ monomer of the present invention, optionally comprising other pharmaceutically active compounds, can be administered to a patient orally, rectally, parenterally, (e.g., intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the $CXCL12_1$ monomer of the invention combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (e.g., propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the $CXCL12_1$ monomer is provided in dry (i.e., powder or granular) form for reconstitution with a suitable vehicle (e.g., sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The $CXCL12_1$ monomer of the present invention may also contain adjuvants such as suspending, preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, such as aluminum monostearate and/or gelatin.

Dosage forms can include solid or injectable implants or depots. In preferred embodiments, the implant comprises an effective amount of the $CXCL12_1$ monomer and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of the $CXCL12_1$ monomer and a silastic polymer. The implant provides the release of an effective amount of $CXCL12_1$ monomer for an extended period ranging from about one week to several years.

Solid dosage forms for oral administration include capsules, tablets, powders, and granules. In such solid dosage forms, the $CXCL12_1$ monomer is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Tablets may be manufactured with pharmaceutically acceptable excipients such as inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Dose Requirements. In particular embodiments, a preferred range for therapeutically or prophylactically effective amounts of $CXCL12_1$ may include 0.1 nM-0.1M, 0.1 nM-0.05M, 0.05 nM-15 µM or 0.01 nM-10 µM. It is to be noted that dosage values may vary with the severity of the condition to be alleviated, especially with multiple sclerosis. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of $CXCL12_1$ monomer in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such as active compound for the treatment of sensitivity in individuals.

Methods of Use. The invention also provides corresponding methods of use, including methods of medical treatment, in which a therapeutically effective dose of $CXCL12_1$ is administered in a pharmacologically acceptable formulation. Accordingly, the invention also provides therapeutic compositions comprising the $CXCL12_1$ and a pharmacologically acceptable excipient or carrier, as described above. The therapeutic composition may advantageously be soluble in an aqueous solution at a physiologically acceptable pH.

In one embodiment, the invention provides a method of treating autoimmune disease in a subject comprising administering to the subject a therapeutically effective amount of a composition comprising $CXCL12_1$. By "autoimmune disease" we mean illnesses generally understood to be caused by the over-production of cytokines, lymphotoxins and antibodies by white blood cells, including in particular T-cells. Such autoimmune diseases include but are not limited to Multiple Sclerosis (MS), Guillain-Barre Syndrome, Amyotrophic Lateral Sclerosis, Parkinson's disease, Alzheimer's disease, Diabetes Type I, gout, lupus, and any other human illness that T-cells play a major role in, such as tissue graft rejection. In addition, diseases involving the degradation of extra-cellular matrix include, but are not limited to, psoriatic arthritis, juvenile arthritis, early arthritis, reactive arthritis, osteoarthritis, ankylosing spondylitis. osteoporosis, muscular skeletal diseases like tendonitis and periodontal disease, cancer metastasis, airway diseases (COPD, asthma or other reactive airways disease), renal and liver fibrosis, cardio-vascular diseases like atherosclerosis and heart failure, and neurological diseases like neuroinflammation and multiple sclerosis. Diseases involving primarily joint degeneration include, but are not limited to, rheumatoid arthritis, psoriatic arthritis, juvenile arthritis, early arthritis, reactive arthritis, osteoarthritis, ankylosing spondylitis. Diseases involving the eye include, but are not limited to autoimmune uveitis and uveoconjunctivitis and dry eye syndrome. Diseases involving post-infections complications of viral or bacterial diseases such as glomerulonephritis, vasculitis, meningoencephalitis. Diseases involving the gastrointestinal system include but are not limited to inflammatory bowel diseases.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace both preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the $CXCL12_1$ monomer of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the $CXCL12_1$ monomer of the present invention is administered to a subject or is used in an assay or other method described herein or a cited reference, e.g., within about 1 hour of the administration or use of the $CXCL12_1$ monomer of the present invention to about 3, 6, 9 months or more after a subject(s) has received the $CXCL12_1$ monomer of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the $CXCL12_1$ monomer of the present invention, where the untreated subjects have, or are subject to developing, the same or similar disease, condition, symptom or the like. Such increases or decreases may be at least about 2%, 5%, 10%, 15%, 200/%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the $CXCL12_1$ monomer of the present invention is administered to a subject or is used in an assay or other method described herein or a cited reference, e.g., within about 1 hour of the administration or use of the $CXCL12_1$ monomer of the present invention to about 3, 6, 9 months or more after a subject(s) has received the $CXCL12_1$ monomer of the present invention.

By "administering" we mean any means for introducing the $CXCL12_1$ monomer of the present invention into the body, preferably into the systemic circulation. Examples include but are not limited to oral, buccal, sublingual, pu$CXCL12_1$onary, transdermal, transmucosal, as well as subcutaneous, intraperitoneal, intravenous, and intramuscular injection.

By "therapeutically effective amount" we mean an amount effective, at dosages and for periods of time necessary, to achieve the desired therapeutic result, such as reduction or reversal of angiogenesis in the case of cancers, or reduction or inhibition of T-cells in autoimmune diseases. A therapeutically effective amount of $CXCL12_1$ may vary according to factors such as the disease state, age, sex, and weight of the subject, and the ability of $CXCL12_1$ to elicit a desired response in the subject. Dosage regimens may be adjusted to provide the optimum therapeutic response. A therapeutically effective amount is also one in which any toxic or detrimental effects of $CXCL12_1$ are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor or the onset of bouts or episodes of multiple sclerosis. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In another embodiment, the invention provides a method of treating a tumor in a subject comprising administering to the subject a therapeutically effective amount of a composition comprising the $CXCL12_1$ monomer. By "tumor" we mean any abnormal proliferation of tissues, including solid and non-solid tumors. For instance, the composition and methods of the present invention can be utilized to treat cancers that manifest solid tumors such as breast cancer, colon cancer, lung cancer, thyroid cancer, ovarian cancer and the like. The composition and methods of the present invention can also be utilized to treat non-solid tumor cancers such as non-Hodgkin's lymphoma, leukemia and the like.

In another embodiment, the present invention provides a method of inhibiting angiogenesis in a subject by administering to the subject a therapeutically effective amount of a composition comprising $CXCL12_1$. By "angiogenesis" we mean the process whereby new blood vessels penetrate tissue thus supplying oxygen and nutrients while removing waste in various pathological conditions including but not limited to diabetic retinopathy, macular degeneration, rheumatoid arthritis, inflammatory bowel disease, cancer, psoriasis, osteoarthritis, ulcerative colitis, Crohn's disease and coronary thrombosis.

In another embodiment, the present invention provides a method of treating inflammation in a subject by administering to the subject a therapeutically effective amount of a composition comprising $CXCL12_1$. By "inflammation" we mean the complex biological response of vascular tissues to harmful stimuli, such as pathogens, damaged cells, or irritants. It is a protective attempt by the organism to remove the injurious stimuli as well as initiate the healing process for the tissue. For instance, the composition and methods of the present invention can be utilized to treat inflammation associated with: an allergic disease such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy; a neurodegenerative disease; a cardiovascular disease; a gastrointestinal disease; a tumor such as a malignant tumor, a benign tumor, a solid tumor, a metastatic tumor and a non-solid tumor; septic shock; anaphylactic shock; toxic shock syndrome; cachexia; necrosis; gangrene; a prosthetic implant such as a breast implant, a silicone implant, a dental implant, a penile implant, a cardiac implant, an artificial joint, a bone fracture repair device, a bone replacement implant, a drug delivery implant, a pacemaker and a respirator tube; menstruation; an ulcer such as a skin ulcer, a bed sore, a gastric ulcer, a peptic ulcer, a buccal ulcer, a nasopharyngeal ulcer, an esophageal ulcer, a duodenal ulcer and a gastrointestinal ulcer; an injury such as an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound; a musculoskeletal inflammation such as a muscle inflammation, myositis, a tendon inflammation, tendinitis, a ligament inflammation, a cartilage inflammation, a joint inflammation, a synovial inflammation, carpal tunnel syndrome and a bone inflammation.

Kits. In another embodiment, the present invention provides a kit comprising a pharmaceutical composition according to the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The monomer of the present invention may also further comprise a delivery device for delivering the composition to a subject. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

The delivery device may comprise a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

II. THE EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1: Engineering a CXCL12 Constitutive Monomer

Figure 5A:
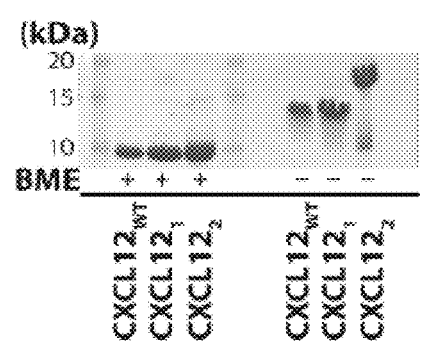
FIG. 5A. Comparison of reducing (left three lanes) and non-reducing (right three lanes) SDS-PAGE of $CXCL12_1$, $CXCL12_{WT}$ and $CXCL12_2$.
Figure 5B:
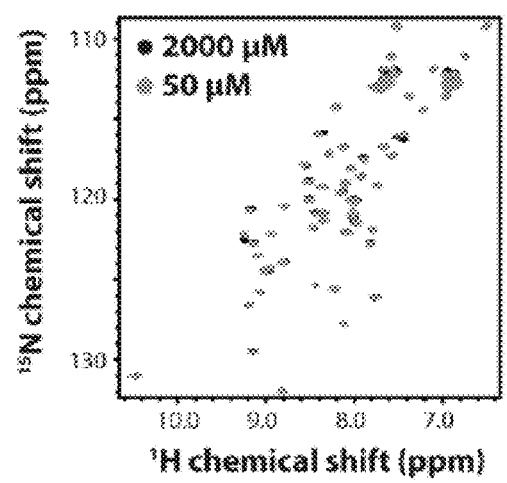
FIG. 5B. Chemical shifts in the $^1H$-$^{15}N$ HSQC of $CXCL12_1$ are negligibly perturbed upon dilution from 2 mM (black) to 50 µM (magenta) in 100 mM $NaPO_4$ (pH 7.4). In comparison $CXCL12_{WT}$ and $CXCL12_{H25R}$ exhibit dimerization $K_d=140$ µM and 1522 µM under identical solution conditions.
Figure 5C:
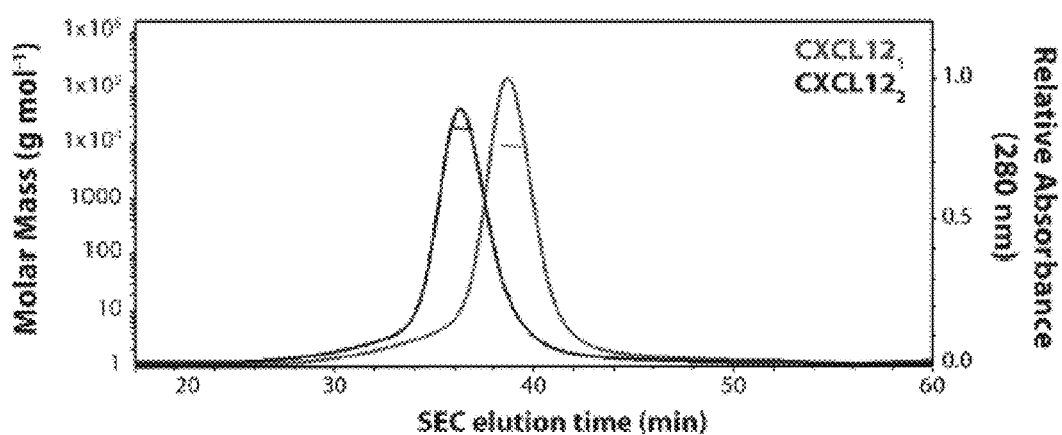
FIG. 5C. SEC-MALS analysis of 40 mg $ml^{-1}$ $CXCL12_1$ (red) and $CXCL12_2$ (black) resulted in homogenous, monodisperse peaks of $8711\pm0.1\%$ g $mol^-$ and $17920\pm0.1\%$ g $mol^-$, respectively. The theoretical molar masses of $CXCL12_1$ and $CXCL12_2$ are 7937 g $mol^-$ and 15958 g $mol^-$, respectively.

The monomer-dimer equilibrium complicates the structural analysis of CXCL12 interactions. A H25R substitution at the dimer interface discourages but does not prevent CXCL12 self-association, as binding of the CXCR4 N-terminus induces CXCL12H25R dimerization. In addition to Coulomb repulsion, a steric clash between the C-terminal α-helices of interacting CXCL12 monomers also limits dimer formation. The original NMR structure of $CXCL12_{WT}$ in acetate buffer (PDB ID 1SDF) possesses a helix orientation (~55° relative to the β-sheet) incompatible with dimerization. After analyzing the proximity and geometry of backbone and $C^\beta$ atoms using the program Disulfide by Design, we constructed a disulfide-constrained CXCL12 monomer using L55C and I58C substitutions to limit helix rearrangement and prevent dimer formation (FIG. 1A). Non-reducing SDS-PAGE, 2D NMR and SEC-MALS analyses of $CXCL12_1$ demonstrate a properly folded, monomeric species (FIG. 5). Whereas $CXCL12_{WT}$ self-associates with a $K_d$=140 µM in 100 mM sodium phosphate, an HSQC dilution series of $CXCL12_1$ in the same conditions produced minimal chemical shift perturbations (FIG. 5B). We concluded that the L55C/I58C disulfide stabilizes a monomeric CXCL12 conformation that is incompatible with dimer formation. In other examples, L66C, I28C, L62C and I38C were also tested.

Figure 1B:
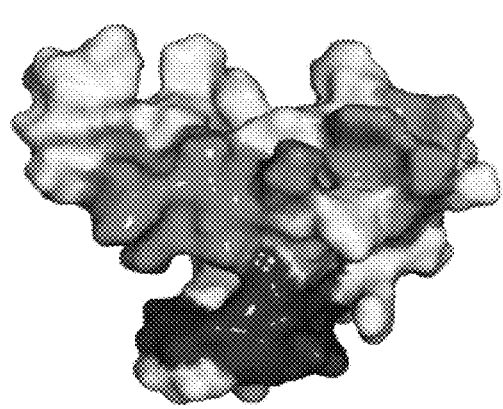
FIG. 1B. Chemical shift perturbations (orange) produced by $CXCR4_{1-38}$ mapped onto CXCL12r (PDB ID 1SDF).
Figure 1C:
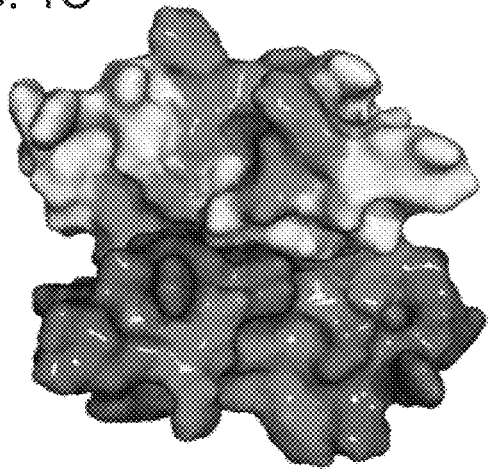
FIG. 1C. Chemical shift perturbations (orange) produced by $CXCR4_{1-38}$ mapped onto $CXCL12_2$ (PDB ID 2K01). Chemical shift perturbations unique to $CXCL12_1$ are highlighted in ruby. Both structures are rotated 180° relative to their respective ribbon representations.
Figure 1D:
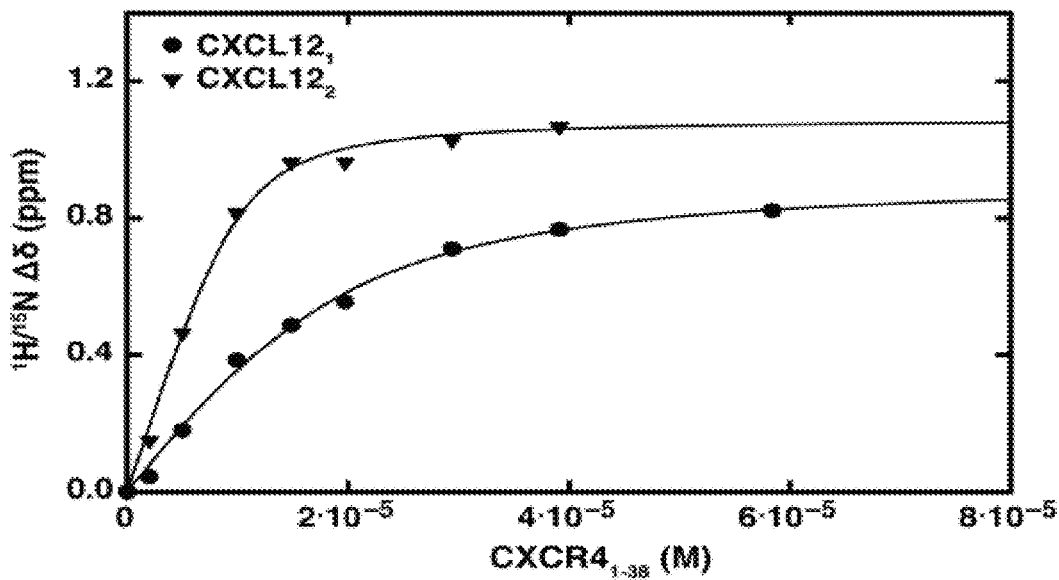
FIG. 1D. $CXCR4_{1-38}$ induced chemical shift perturbations fitted to a quadratic binding equation resulted in $CXCL12_1$ and $CXCL12_2$ affinities of 3.5±0.1 and 0.9±0.3 μM, respectively.

The CXCL12 monomer and dimer possess distinct $CXCR4_{1-38}$ binding sites. To establish a point of reference for subsequent measurements with smaller peptides, we monitored the binding of $CXCR4_{1-38}$ to the $CXCL12_1$ and $CXCL12_2$ variants by 2D NMR. Chemical shift mapping onto the $CXCL12_1$ model and $CXCL12_2$ NMR structure (FIG. 1B, 1C) highlighted perturbations across the β2 and β3 strands, consistent with the previous studies, but CXCL12$_1$ also displayed additional contacts involving residues 58-61, 65, and 66 of the helix. Nonlinear fitting of chemical shift perturbations yielded K$_d$ values of 3.5±0.1 μM (CXCL12$_1$) and 0.9±0.3 μM (CXCL12$_2$) (FIG. 1D). We recently demonstrated that perturbations induced by CXCL12$_{WT}$ binding to [U-$^{15}$N]-CXCR4$_{1-38}$ arise from the combination of distinct monomeric and dimeric interactions; in particular, CXCR4 residues 4-9 interact strongly with the preferentially monomeric CXCL12$_{H25R}$ variant but weakly with CXCL12$_2$. Taken together, these results suggest that the CXCR4 N-terminus makes unique contacts with the helix of monomeric CXCL12 that are occluded by dimerization of the chemokine.

Figure 6A:
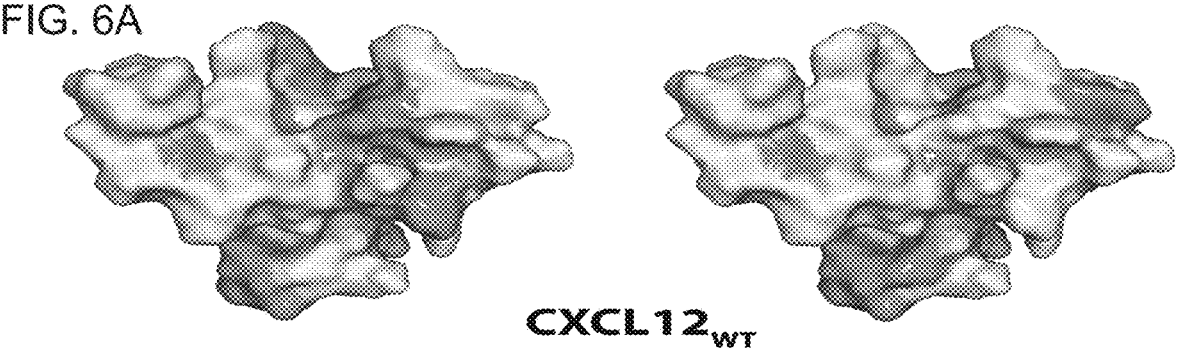
FIG. 6A. Chemical shift mapping of $_{18}SGDsYDSM_{24}$ (SEQ ID NO:4) and $_{18}SGDYDSM_{24}$ (SEQ ID NO:5) peptides on CXCL12 variants. Sulfated and unsulfated Tyr21 peptides produce similar chemical shift changes in the Tyr21 pocket of $CXCL12_{WT}$.
Figure 6B:
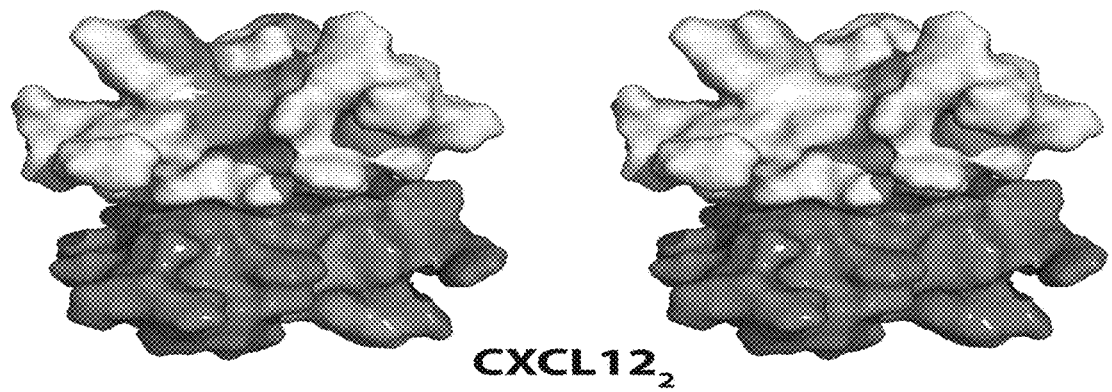
FIG. 6B. Sulfated and unsulfated Tyr21 peptides produce similar chemical shift changes in the Tyr21 pocket of $CXCL12_2$.
Figure 6C:
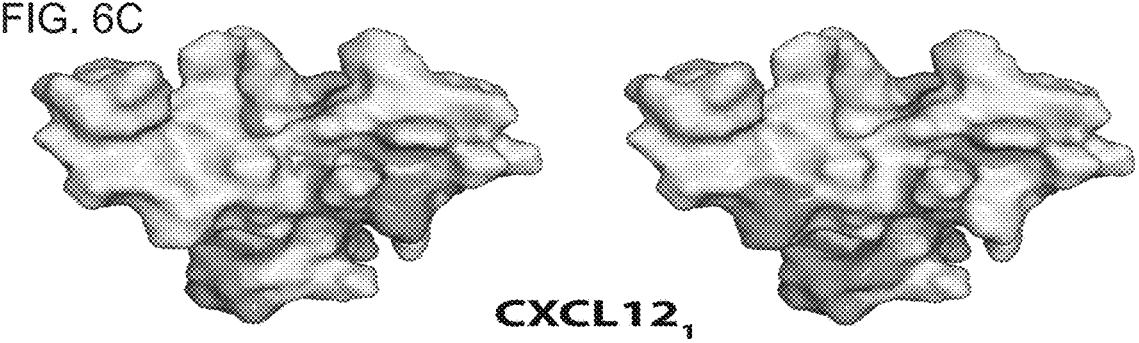
FIG. 6C. Sulfated and unsulfated Tyr21 peptides produce similar chemical shift changes in the Tyr21 pocket of $CXCL12_1$.
Figure 7A:
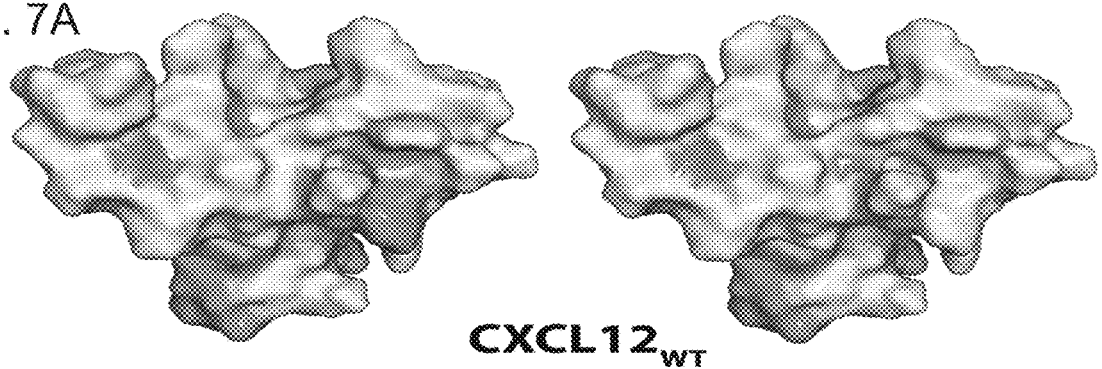
FIG. 7A. Chemical shift mapping of $_9SDNsYTEE_{15}$ (SEQ ID NO:6) and $_9SDNYTEE_{15}$ (SEQ ID NO:7) peptides on CXCL12 variants. No conserved Tyr12 pocket was observed for any Tyr12 peptide variant on $CXCL12_{WT}$.
Figure 7B:
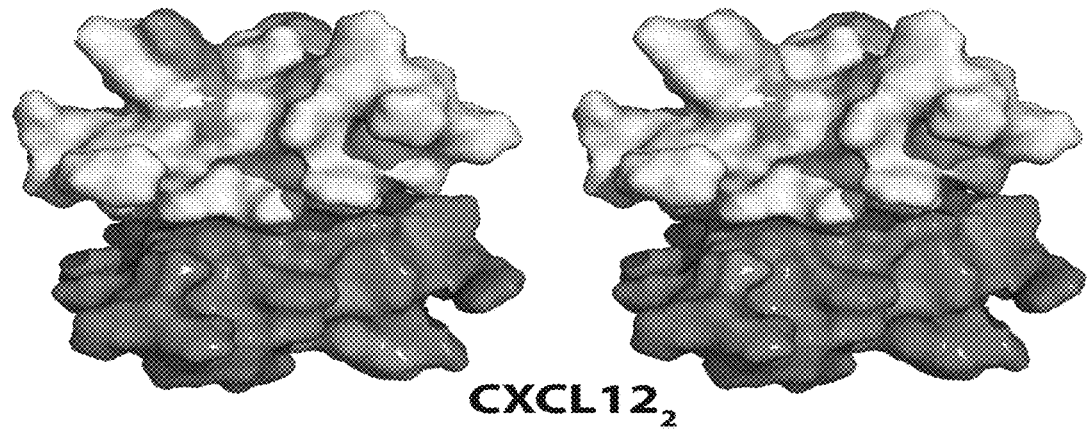
FIG. 7B. No conserved Tyr12 pocket was observed for any Tyr12 peptide variant on $CXCL12_2$.
Figure 7C:
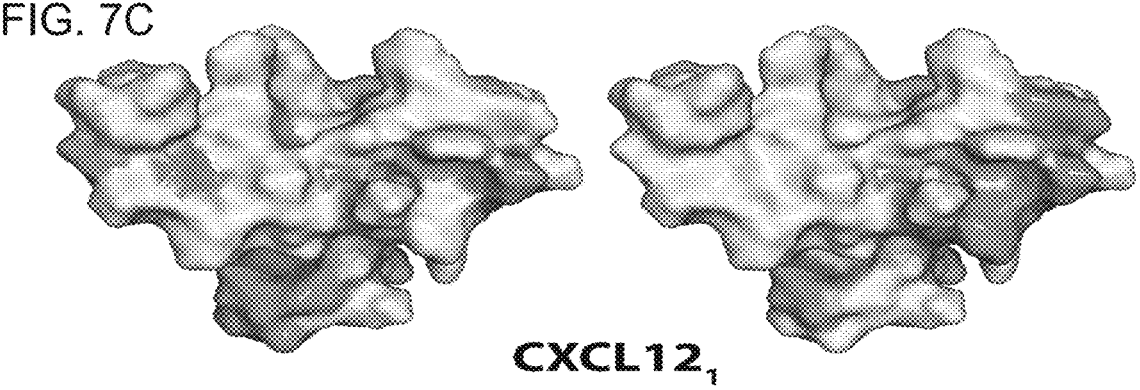
FIG. 7C. No conserved Tyr12 pocket was observed for any Tyr12 peptide variant on $CXCL12_1$.
Figure 8A:
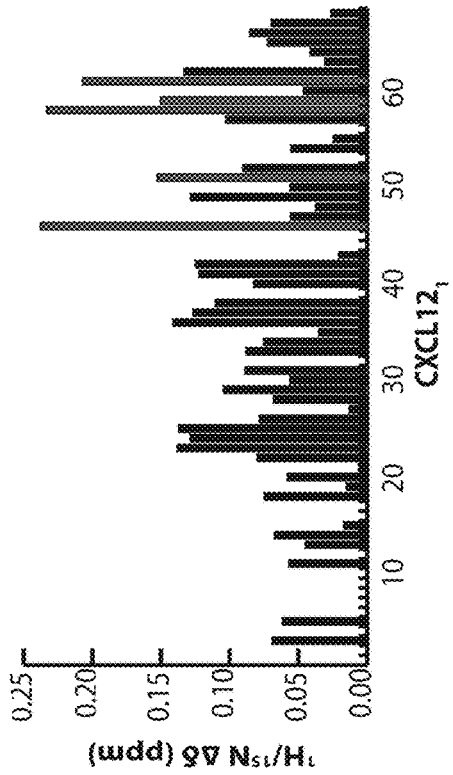
FIG. 8A. The $_4ISIYTSD_{10}$ (SEQ ID NO:8) peptide binds similar pockets on $CXCL12_{WT}$ and $CXCL12_1$. The $4ISIYTSD_{10}$ (SEQ ID NO:8) peptide induces significant chemical shifts at the Tyr7 pocket of $CXCL12_{WT}$.
Figure 8B:
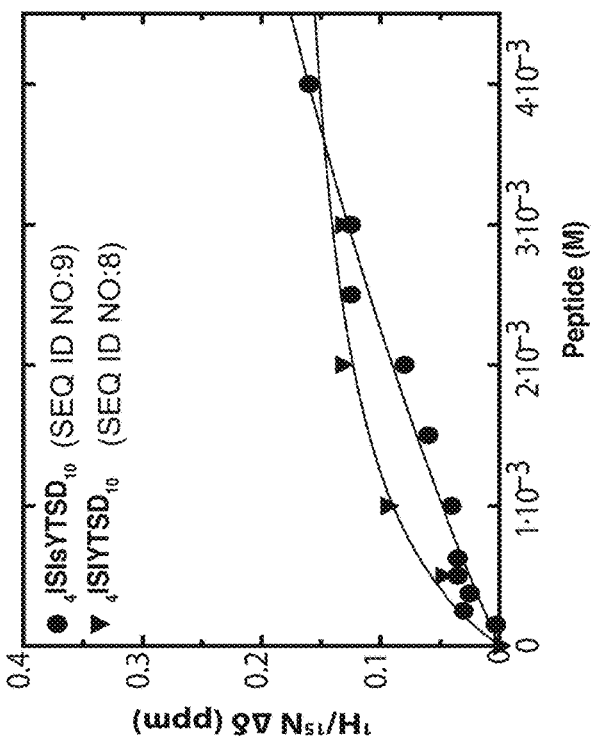
FIG. 8B. The $4ISIYTSD_{10}$ (SEQ ID NO:8) peptide binds similar pockets on $CXCL12_{WT}$ and $CXCL12_1$. The $4ISIYTSD_{10}$ (SEQ ID NO:8) peptide induces significant chemical shifts at the Tyr7 pocket of $CXCL12_1$.
Figure 8C:
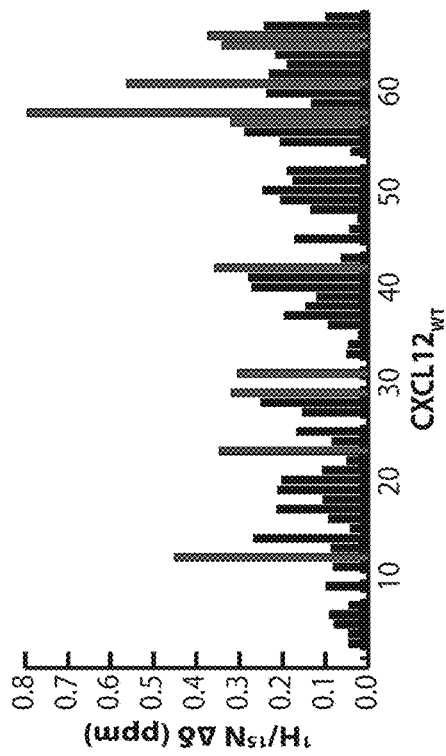
FIG. 8C. Sulfation at Tyr7 reduces sulfopeptide affinity for $CXCL12_{WT}$ from $1.9\pm0.3$ mM to $4.3\pm0.3$ mM.
Figure 8D:
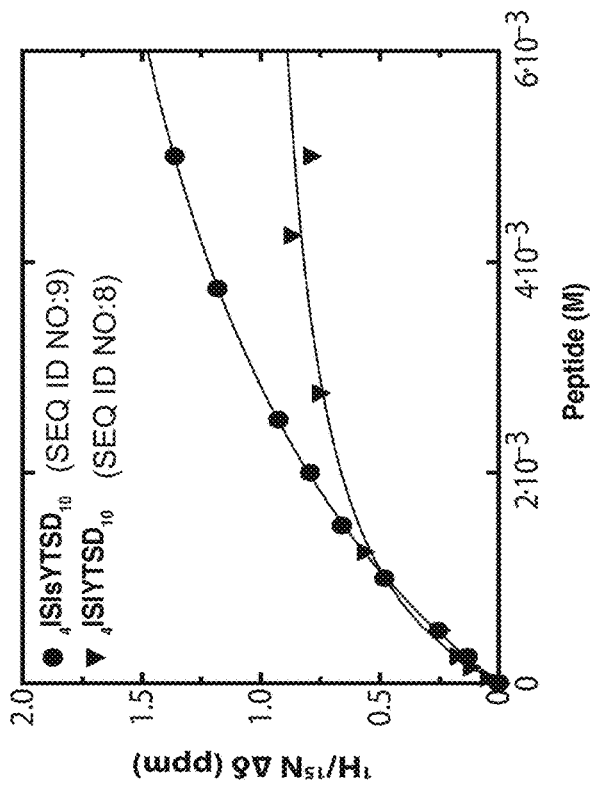
FIG. 8D. Sulfation at Tyr7 reduces sulfopeptide affinity for $CXCL12_1$ from $1.1\pm0.6$ mM to $6.1\pm1.3$ mM.

CXCL12 binding of short CXCR4 sulfopeptides. Sulfation of the CXCR4 N-terminal extracellular domain at either Tyr21 alone or in combination with Tyr12 and Tyr7 enhances its affinity for CXCL12. To assess the respective contribution of each sulfotyrosine, we synthesized short sulfated and unsulfated CXCR4 heptapeptides centered on each of the three tyrosine residues (FIG. 2A). Each peptide was acetylated and amidated to create uncharged N- and C-termini, respectively. A total of six peptides were titrated into each CXCL12 variant and monitored by 2D $^1$H-$^{15}$N HSQC experiments. For each titration, the chemical shift change of every residue was used to identify the binding site and calculate the interaction affinity. Table 1 contains a complete list of peptide binding affinities and binding energies.

cleft at the dimer interface enabling sTyr7 to contact the R20 and V23 side chains of CXCL12. Here, the greatest shift perturbations (V49, T31 and F14) induced by the sTyr7 and sTyr12 sulfopeptides were more consistent with binding to the sTyr21 recognition site (FIGS. 2, 6 and 7).

Sulfopeptides bound with higher affinity than their unsulfated analogs, as observed in previous studies with one notable exception. Binding of the unsulfated Tyr7 peptide to CXCL12$_1$ was roughly five-fold stronger than the sTyr7 sulfopeptide (Table 1). In contrast to the sTyr7 sulfopeptide, the unsulfated version induced substantial chemical shift changes in residues 23-25, 58-59, and 61 (FIG. 2E), matching the monomer-specific shift perturbations detected with CXCR4$_{1-38}$ (FIG. 1B). Titrations with CXCL12$_{WT}$ produced a similar pattern of shift perturbations and a two-fold higher affinity for the unsulfated Tyr7 peptide (FIG. 8), but there was no preferential binding to the CXCL12$_2$ dimer. Unlike Tyr21 which is rapidly modified by recombinant tyrosylprotein sulfotransferase-1 (TPST-1), Tyr7 sulfation is slow and not consistently predicted by the available algorithms. Contacts with the CXCR4 N-terminus are predominantly hydrophobic and favored when Tyr7 is unmodified and CXCL12 is monomeric.

The Tyr21 peptide exhibits high specificity and affinity. We monitored the binding of unsulfated $_{18}$SGDYDSM$_{24}$ (SEQ ID NO:5) and sulfated $_{18}$SGDsYDSM$_{24}$ (SEQ ID NO:4) to each CXCL12 variant by 2D NMR. Consistent with the CXCL12$_2$:CXCR4$_{1-38}$ complex structure, the unsulfated peptide produced chemical shift perturbations

TABLE 1

Equilibrium dissociation constants and Gibbs' free energy of binding for peptide: CXCL12 variant complexes.

| Peptide | CXCL12$_{WT}$ | | CXCL12$_1$ | | CXCL12$_2$ | |
|---|---|---|---|---|---|---|
| | K$_d$ | ΔG (kcal mol$^{-1}$) | K$_d$ | ΔG (kcal mol$^{-1}$) | K$_d$ | ΔG (kcal mol$^{-1}$) |
| CXCR4$_{1-38}$ | 4.5 ± 2.2 μM* | −7.29* | 3.5 ± 0.1 μM | −7.43 | 0.9 ± 0.3 μM | −8.24 |
| $_{18}$SGDsYDSM$_{24}$ (SEQ ID NO: 4) | 1.8 ± 0.2 mM | −3.74 | 1.6 ± 0.2 mM | −3.81 | 211 ± 23 μM | −5.01 |
| $_{18}$SGDYDSM$_{24}$ (SEQ ID NO: 5) | 2.7 ± 0.5 mM | −3.50 | 1.5 ± 0.4 mM | −3.85 | 831 ± 137 μM | −4.20 |
| $_9$SDNsYTEE$_{15}$ (SEQ ID NO: 6) | 1.0 ± 0.1 mM | −4.09 | 1.8 ± 0.3 mM | −3.74 | **266 ± 38 μM | −4.87 |
| $_9$SDNYTEE$_{15}$ (SEQ ID NO: 7) | 2.1 ± 0.3 mM | −3.65 | 2.7 ± 0.8 mM | −3.50 | 332 ± 91 μM | −4.74 |
| $_4$ISIsYTSD$_{10}$ (SEQ ID NO: 9) | 4.3 ± 0.3 mM | −3.22 | 6.1 ± 1.3 mM | −3.02 | **386 ± 91 μM | −4.65 |
| $_4$ISIYTSD$_{10}$ (SEQ ID NO: 8) | 1.9 ± 0.3 mM | −3.71 | 1.1 ± 0.6 mM | −4.03 | **418 ± 60 μM | −4.60 |

Figure 2D:
FIG. 2D. The previously defined positions of heptapeptides are reproduced from the $CXCL12_2:CXCR4_{1-38}$ NMR structure (PDB ID 2K05).
Figure 2E:
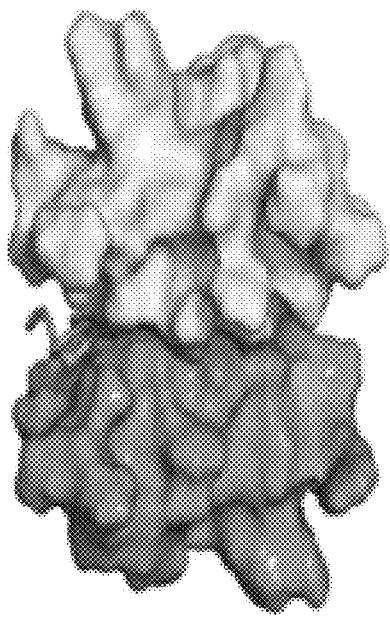
FIG. 2E. Chemical shift perturbations induced by sTyr7. Chemical shift perturbations identify distinct binding sites for the sTyr7.
Figure 2F:
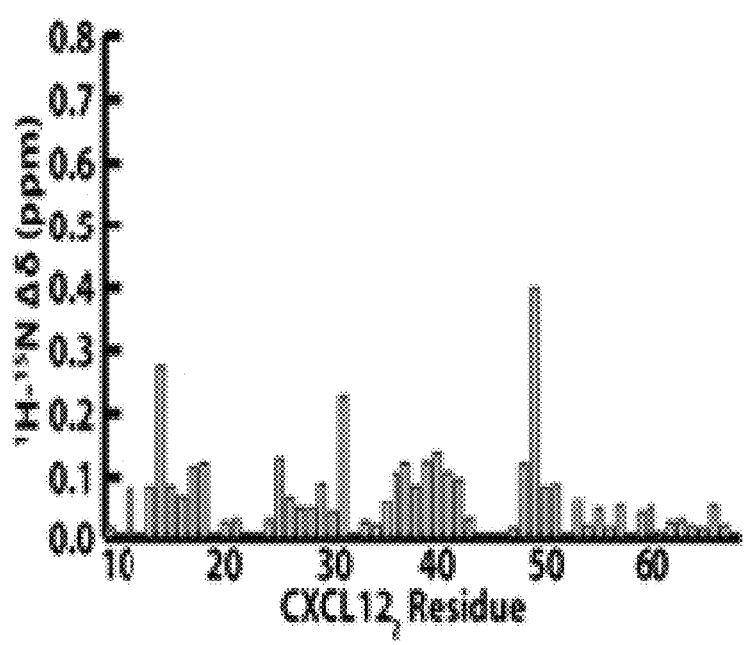
FIG. 2F. Chemical shift perturbations induced by sTyr7. Chemical shift perturbations identify distinct binding sites for the sTyr7.
Figure 2G:
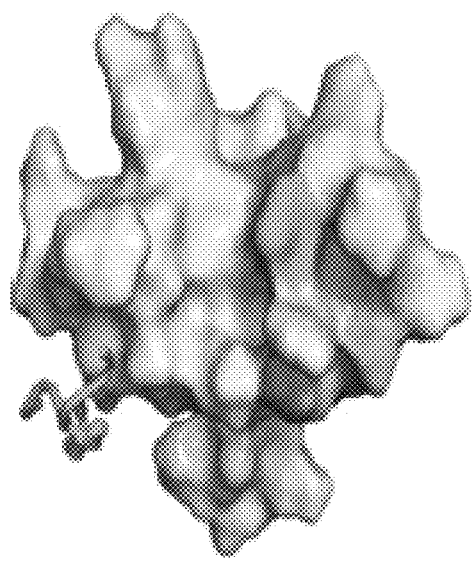
FIG. 2G. Chemical shift perturbations induced by sTyr7. Chemical shift perturbations identify distinct binding sites for the sTyr7.
Figure 2H:
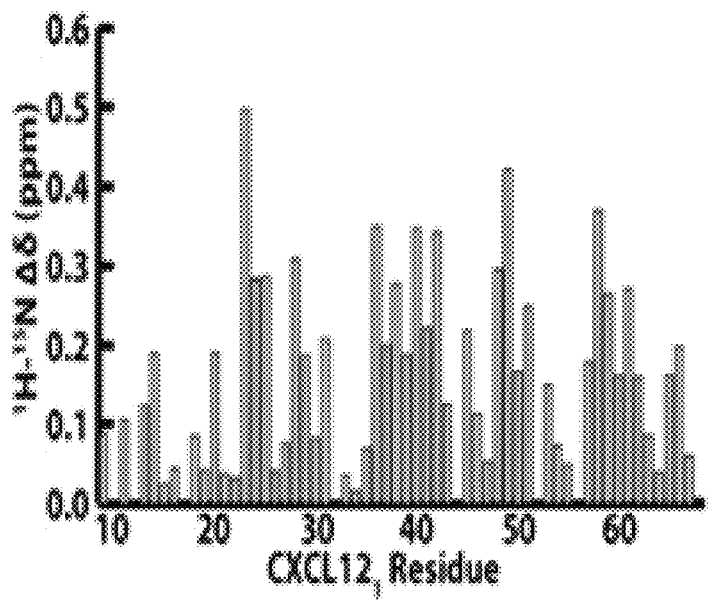
FIG. 2H. Chemical shift perturbations induced by sTyr7. Chemical shift perturbations identify distinct binding sites for the sTyr7.
Figure 2I:
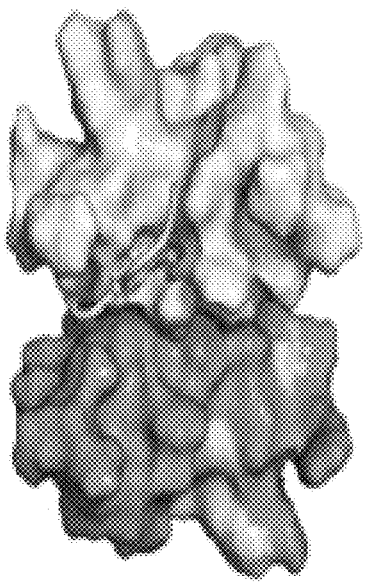
FIG. 2I. Chemical shift perturbations induced by sTyr12. Non-specific binding was observed for the sTyr12 sulfopeptide.
Figure 2J:
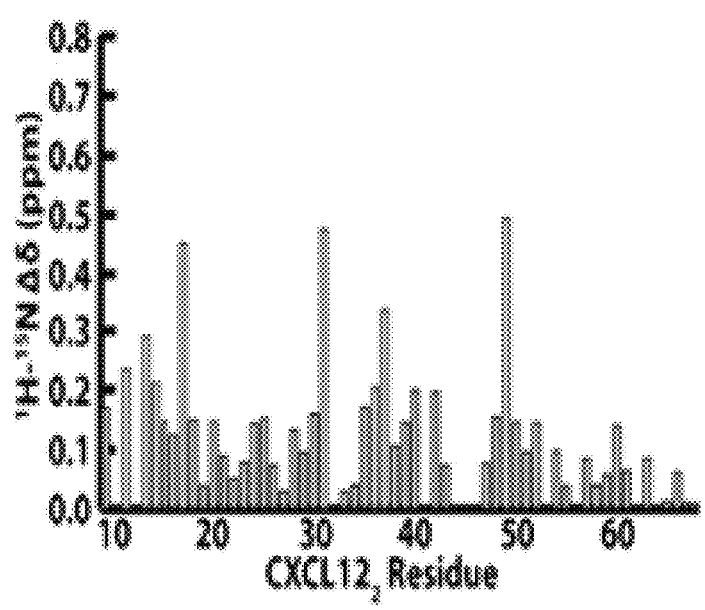
FIG. 2J Chemical shift perturbations induced by sTyr12. Non-specific binding was observed for the sTyr12 sulfopeptide.
Figure 2K:
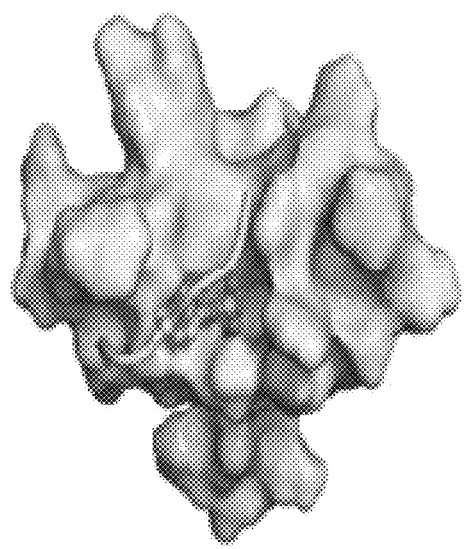
FIG. 2K. Chemical shift perturbations induced by sTyr12. Non-specific binding was observed for the sTyr12 sulfopeptide.
Figure 2L:
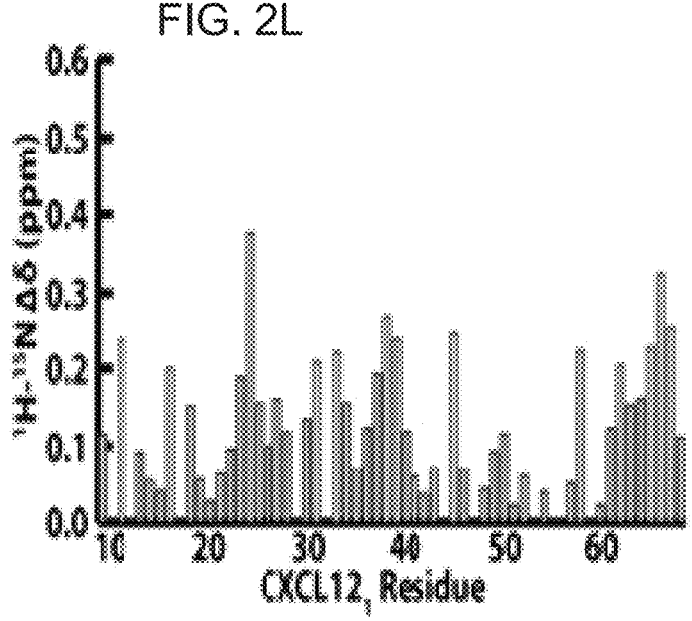
FIG. 2L. Chemical shift perturbations induced by sTyr12 Non-specific binding was observed for the sTyr12 sulfopeptide.
Figure 2M:
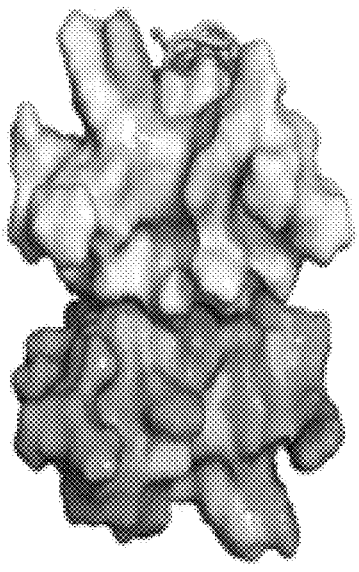
FIG. 2M. Chemical shift perturbations induced by sTyr21 sulfopeptides map to the Tyr21 pocket on $CXCL12_2$ (PDB 2K05). Chemical shift perturbations identify distinct binding sites for the sTyr21.
Figure 2N:
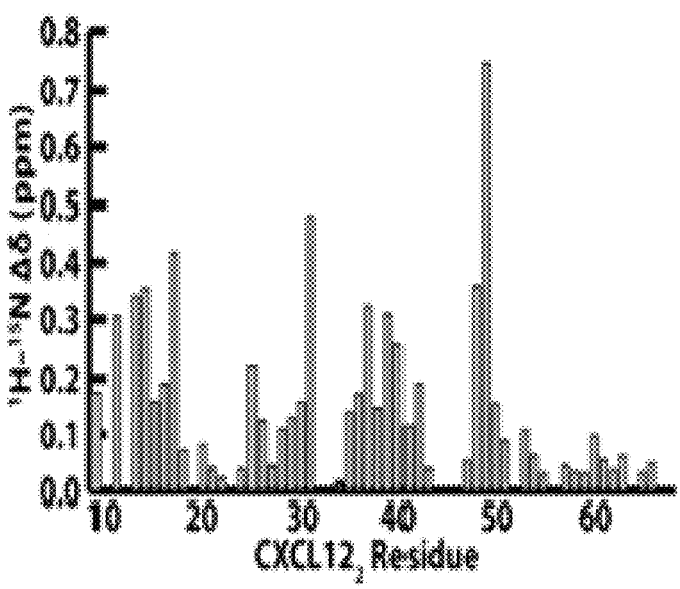
FIG. 2N. Chemical shift perturbations induced by sTyr21 sulfopeptides map to the Tyr21 pocket on $CXCL12_2$ (PDB 2K05). Chemical shift perturbations identify distinct binding sites for the sTyr21.
Figure 2O:
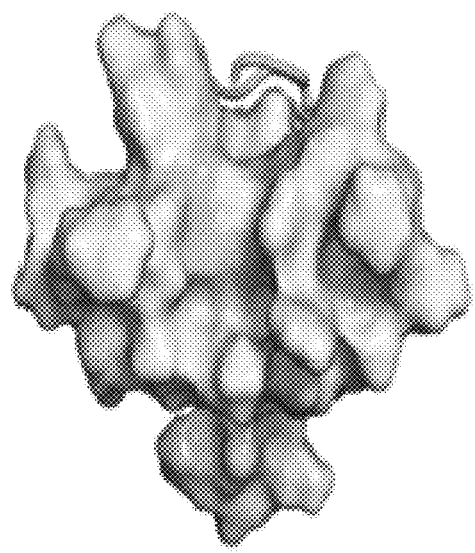
FIG. 2O. Chemical shift perturbations induced by sTyr21 sulfopeptides map to the Tyr21 pocket on $CXCL12_2$ (PDB 2K05). Chemical shift perturbations identify distinct binding sites for the sTyr21.
Figure 2P:
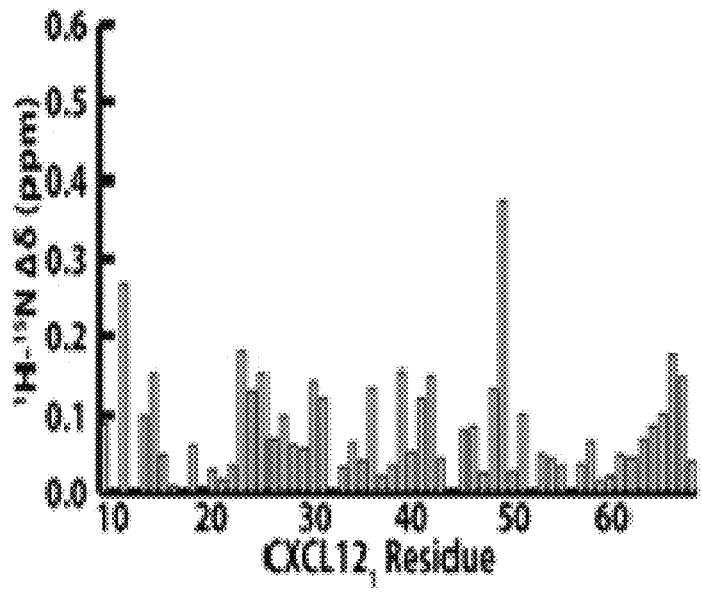
FIG. 2P. Chemical shift perturbations induced by sTyr2l sulfopeptides map to the Tyr21 pocket on $CXCL12_2$ (PDB 2K05). Chemical shift perturbations identify distinct binding sites for the sTyr21.

ΔG = −RT ln K$_d$ @ 298 K
*K$_d$ and ΔG calculated from Veldkamp et al. (32)
**Non-specific binding to sY21 position As expected, the affinity of short CXCR4 peptides for all CXCL12 variants was greatly reduced relative to the intact CXCR4$_{1-38}$ N-terminal domain, with K$_d$ values ranging from ~0.2-6 mM (Table 1). Interestingly, nearly all peptides bound most tightly to the CXCL12$_2$ locked dimer, whereas binding to CXCL12$_{WT}$ and CXCL12$_1$ were roughly equivalent. In titrations with each of the CXCL12 variants, chemical shift mapping indicated that peptides encompassing Tyr21 consistently bound to the previously defined sTyr21 pocket, as detailed below (FIG. 2D, FIG. 6). In contrast, the Tyr7 and Tyr12 peptides did not localize to their corresponding interaction surfaces observed in the dimeric CXCL12$_2$: CXCR4$_{1-38}$ complex structure (FIGS. 2B, 2C). For example, in the NMR structure residues 4-10 of CXCR4 occupied a localized to residues in the β2 strand, β3 strand and N-loop of each variant (FIG. 3A; FIG. 6). CXCL12$_{WT}$ and CXCL12$_1$ further exhibited shifts in residues 58 and 65-67 of the helix (FIG. 6). Sulfation of Tyr21 strengthened the affinity of $^{18}$SGDYDSM$_{24}$ (SEQ ID NO:5) for all three CXCL12 variants and increased the magnitude of each perturbation without altering the pattern of responding residues (Table 1; FIG. 3B). The sTyr21 sulfopeptide bound to CXCL12$_2$ with the highest affinity (K$_d$=211 μM) compared to all other peptide:chemokine combinations—four-fold stronger than the unsulfated variant (K$_d$=831 μM).

Given that unsulfated CXCR4$_{1-38}$ (K$_d$=0.9 μM) binds CXCL12$_2$ with a Gibbs free energy of −8.24 kcal mol$^-$, our results suggest that the $^{18}$SGDYDSM$_{24}$ (SEQ ID NO:5)

fragment alone provides about half of the binding energy (ΔG=−4.2 kcal mol⁻¹) for the CXCR4:CXCL12₂ 'site 1' interaction. The identification of such hot spots, or regions of binding interfaces that contribute substantial binding energy, are of particular interest in the generation of protein-protein interface inhibitors. The major energetic contributions of the Tyr21 pocket justify our recent success in developing small molecules that antagonize receptor activation. Further, identification of the hydrophobic Tyr7 pocket on monomeric CXCL12 demonstrates the utility of small receptor peptides in identifying druggable chemokine hot spots.

Tyr7 and Tyr12 are dispensable for CXCR4 activation by CXCL12. TPST enzymes catalyze the O-sulfation of Tyr21 much more efficiently than the Tyr12 or Tyr7 residues in vitro. Further, sTyr21 recognizes a cleft on CXCL12 that may be conserved across most members of the chemokine superfamily. To test the hypothesis that Tyr21 sulfation is critical for receptor activation, tyrosine to alanine mutations were introduced into FLAG-tagged CXCR4 and expressed in CHO-K1 cells. CHO cells were chosen because they do not express endogenous CXCR4 and yield high levels of sulfated protein. Receptor activation was assessed by monitoring the calcium response as a function of increasing $CXCL12_{WT}$ concentrations (FIG. 3C). The response of CXCR4(Y7A) was similar to wildtype CXCR4 whereas the potency of CXCR4(Y12A) was reduced 3-fold. In contrast, CXCR4(Y21A) was significantly impaired both in terms of $EC_{50}$ and efficacy. The combined mutation of Y7A, Y12A, and Y21A did not further diminish the potency relative to CXCR4(Y21A) but reduced the efficacy to ~20% of the wildtype receptor.

Figure 9:
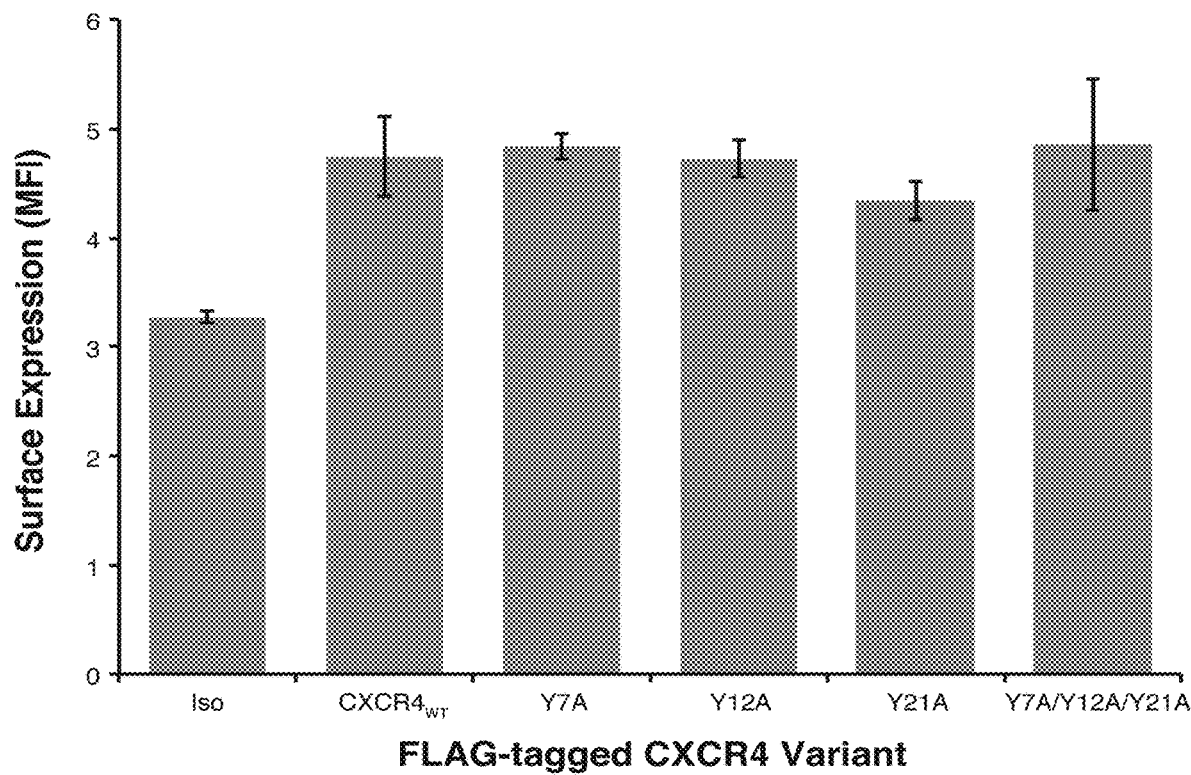
FIG. 9. FLAG-tagged CXCR4 variants possess similar surface expression. CHO cells transiently-transfected with FLAG-tagged CXCR4 variants were strained with either IgG1 control or anti-FLAG and then analyzed by flow cytometry. Results are representative of two experiments with three replicates each.

We hypothesize that protein misfolding is not responsible for the altered efficacies for two reasons. First, all of the mutants are surface-expressed at levels equivalent to the wildtype CXCR4 receptor (FIG. 9). Second, the CXCR4 N-terminus is disordered and is not believed to participate in folding the overall tertiary structure of the receptor. This prompts the question of why there are efficacy changes at all. Our data suggests that the two-site model, in which site 1 is discretely responsible for chemokine binding and site 2 is specific for activation, is oversimplified and that both of these regions are ultimately required for full receptor activation. We conclude that sulfotyrosine modifications serve both to enhance CXCL12 binding affinity, and therefore potency, as well as signaling efficacy. Taken together, our results define the relative importance of individual CXCR4 sulfotyrosine modifications (Tyr21>Tyr12>Tyr7) for CXCL12 binding and receptor activation.

Figure 4A:
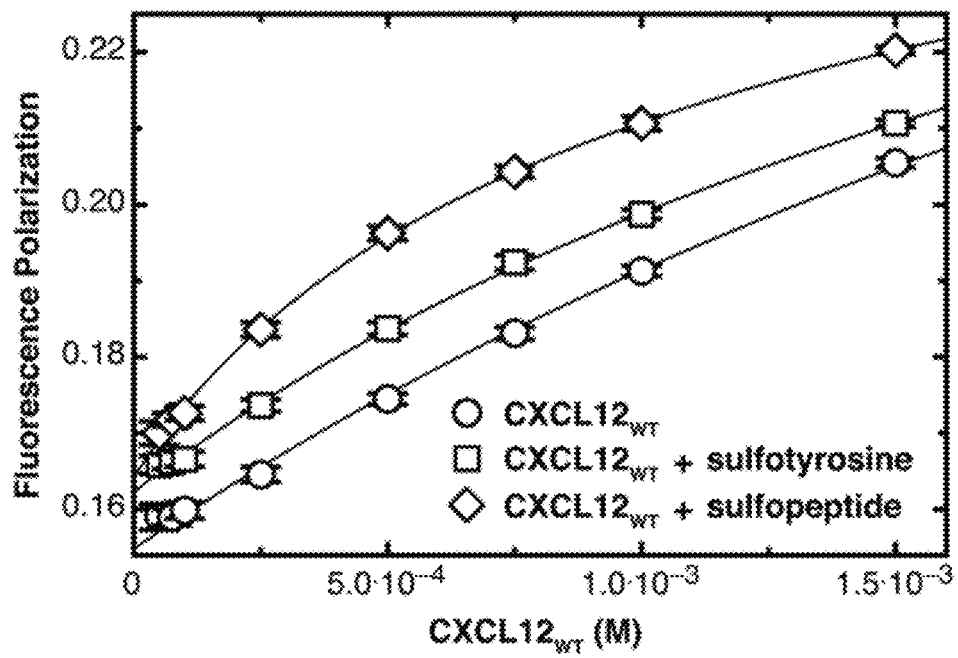
FIG. 4A. The sTyr21 binding site is allosterically linked to CXCL12 dimerization. Intrinsic tryptophan fluorescence was used to calculate the $CXCL12_{WT}$ dimerization affinity alone (circles, $K_d=15.1\pm0.4$ mM), in the presence of 50 mM sulfotyrosine (squares; $K_d=8.9\pm1.8$ mM), or in the presence of 3 mM sTyr21 sulfopeptide (diamonds; $K_d=2.6\pm0.4$ mM).

Binding at the Tyr21 site promotes dimerization. Chemokine dimerization is highly sensitive to numerous factors including GAGs, divalent anions, and pH (32). The CXCR4 N-terminus also promotes CXCL12 dimerization, which drastically alters the cellular response. Interestingly, sTyr21 sulfopeptide binding to CXCL12₂ is 20-fold stronger than to $CXCL12_{WT}$ or CXCL12₁ (FIG. 3B). In addition, the sulfopeptide produces large perturbations at the dimer interface of $CXCL12_{WT}$ (FIG. 6) suggesting it may allosterically induce CXCL12%'r dimerization. We used intrinsic tryptophan fluorescence polarization (FP) to determine the $K_d$ for $CXCL12_{WT}$ dimerization in the presence and absence of 3 mM sTyr21 sulfopeptide. The sulfopeptide shifts the $K_d$ for $CXCL12_{WT}$ dimerization from 15.1±0.4 mM to 2.6±0.4 mM. Free sulfotyrosine (Tyr-SO₃H), which also binds the sTyr21 pocket, also promotes CXCL12 dimerization ($K_d$=9.3±1.8 mM; FIG. 4A).

Figure 4B:
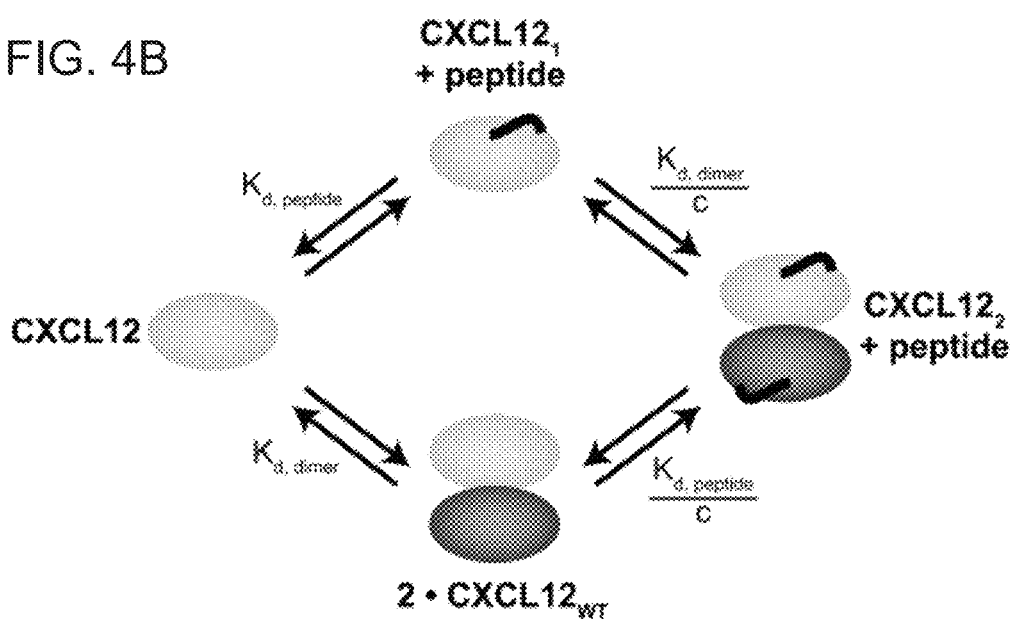
FIG. 4B FP and NMR derived binding affinities were used to produce a thermodynamic cycle, which illustrates that CXCL12 dimerization and sTyr21 sulfopeptide binding are coupled. After one ligand has bound, the affinity for the second ligand is enhanced with a cooperativity factor.

The free energy changes derived from NMR binding ($\Delta G_{bind}$) and FP dimerization ($\Delta G_{dimer}$) measurements at 298 K were used to construct a thermodynamic cycle diagram (FIG. 4B). In pathway 1, CXCL12 binds the sTyr21 sulfopeptide ($\Delta G_{bind}$=−3.8 kcal mol⁻) and then dimerizes ($\Delta G_{dimer}$=−3.5 kcal mol⁻). When the sequence is reversed (pathway 2), CXCL12 dimerizes with $\Delta G_{dimer}$=−2.5 kcal mol⁻ and then binds the sTyr21 sulfopeptide with $\Delta G_{bind}$=−5.0 kcal mol⁻. Analysis of both pathways yields similar coupling energies of −1.2 kcal mol⁻ and −1.0 kcal mol⁻, respectively, that link CXCL12 dimerization to ligand binding in the sTyr21 recognition pocket. Similar studies with both CCL5 and CCL2 report binding of their respective N-terminal peptides, both sulfated and unsulfated, to promote dimer dissociation. The apparent disparity between these studies and our data is most easily explained by the spatially distinct dimerization interfaces of CXC- and CC-type chemokines. CXCL12 dimerizes through the β1 strand and α-helix whereas CC-type chemokines self-associates using the N-terminus, N-loop and β3 strand. Nonetheless, both chemokines bind sulfopeptides in the cleft formed by the N-loop and β3 strand. The close proximity of the sulfopeptide-binding site to the CC-type dimer interface is more consistent with dissociation through direct binding competition rather than an allosteric mechanism.

Many intracellular signal transduction complexes involve recognition of a recurring sequence motif by a protein interaction domain. Binding to certain short linear motifs (or SLiMs) depends on post-translational modifications (PTMs) like phosphorylation, acetylation or methylation, and their corresponding recognition sites are often viewed as promising targets for drug discovery. Likewise, tyrosine sulfation enhances protein-protein interactions in the extracellular space and sulfotyrosine recognition likely defines a new class of druggable extracellular targets. However, selective binding may require the combination of multiple SLiMs as observed for the WASP interacting protein (WIP) which uses three distinct recognition epitopes, including the conserved polyproline motif, to bind the EVH1 domain of N-WASP.

Many chemokine receptors contain multiple N-terminal tyrosines, which are predicted to be sulfated to different levels based on the suitability of the flanking sequences for TPST recognition. We treated each tyrosine in the CXCR4 N-terminus as the center of a SLiM and found that the most efficient site of enzymatic sulfation (Tyr21) is also the most important motif for binding to both CXCL12 monomers and dimers. Surprisingly, neither the Tyr7 or Tyr12 motif bound to a unique site on the CXCL12 dimer, and sulfation of the Tyr7 motif eliminated the site-specific binding to the CXCL12 monomer observed with the unsulfated Tyr7 motif. To our knowledge, this is the first demonstration that sulfation of chemokine receptors does not universally enhance complex affinity.

In contrast, our data suggests that distinct patterns of tyrosine sulfation could encode selectivity either by enhancing or reducing affinity for unique recognition sites. Taken together, this implies another layer of regulation for chemokine signaling. The structural basis for this effect awaits further study, but it appears that monosulfated (Tyr7/Tyr12/sTyr21) CXCR4 would exhibit a preference for the monomeric CXCL12 ligand while sulfation of Tyr7 would bias CXCR4 toward interactions with a CXCL12 dimer. Regardless, we conclude that the most functionally relevant mode of CXCL12-CXCR4 interaction involves specific recognition of a sulfotyrosine at position 21, and additional interactions with the receptor N-terminus that are independent of tyrosine sulfation.

Our results for CXCL12 binding to the sTyr21 motif in CXCR4 also suggest that chemokine oligomerization may be subject to allosteric control. Binding of the sTyr21 sulfopeptide, which is too short to contact both subunits of a CXCL12 dimer, significantly enhances CXCL12 dimerization by an indirect mechanism. Because dimerization converts CXCL12 into a partial agonist that potently inhibits chemotaxis and tumor metastasis, variations in the sulfation pattern of CXCR4 could in principle have functional consequences in vivo. Moreover, ligands that occupy the sTyr21 recognition site of CXCL12 may act as competitive inhibitors of receptor binding and allosteric modulators of chemokine function.

Construction of $CXCL12_1$ plasmid. The $CXCL12_1$ variant was produced via mutagenesis of the $CXCL12_{WT}$ construct using complementary primers and the QuikChange Site-Directed Mutagenesis Kit (Stratagene) as per the manufacturer's instructions. The expression vector insert was confirmed by DNA sequencing.

Protein expression and purification. $CXCL12_{WT}$, $CXCL12_1$ and $CXCL12_2$ were expressed and purified as described previously. $CXCR4_{1-38}$ comprising the first 38 amino acids of CXCR4 preceded by a residual GlyMet dipeptide tag, was expressed and purified as previously described.

Size-exclusion chromatography multi-angle light scattering (SEC-MALS). SEC was performed at a flow rate of 0.4 ml min⁻ on a Superdex 75 10/300 GL analytical column (GE Healthcare) and monitored by an 18-angle MALS detector (Dawn Heleos II). $CXCL12_1$ (40 mg ml$^{-1}$; 5 mM) and $CXCL12_2$ (40 mg ml$^{-1}$; 2.5 mM) were solubilized in 25 mM MES (pH 6.8), 650 mM NaCl, and 0.02% (w/v) $NaN_3$. Samples were then applied to the column in a mobile phase of identical composition. Peak dispersion and average molar mass were calculated using Astra software.

NMR spectroscopy. All NMR spectra were acquired on a Bruker DRX 600 MHz spectrometer equipped with a $^1$H, $^{15}$N, $^{13}$C TXI cryoprobe at 298 K. Experiments were performed with either 50 µM [U-$^{15}$N]-$CXCL12_{WT}$, -$CXCL12_1$, or -$CXCL12_2$ proteins in a solution containing 25 mM deuterated MES (pH 6.8), 10% (v/v) $D_2O$, and 0.02% (w/v) $NaN_3$. Full-length $CXCR4_{1-38}$ peptide titrations required 20 µM [U-$^{15}$N]-$CXCL12_1$ and -$CXCL12_2$ protein samples. Sulfated CXCR4 peptides were reconstituted at 100 mM in 25 mM deuterated MES, 10% (v/v) $D_2O$, and 0.02% (w/v) $NaN_3$ buffer. Unsulfated CXCR4 peptides were similarly reconstituted to 15 mM. Two separate 4ISIYTSD$_{10}$ (SEQ ID NO:8) peptide samples were reconstituted at 10 mM and 15 mM peptide in 25 mM deuterated MES, 10% (v/v) $D_2O$, 0.02% (w/v) $NaN_3$ buffer, from lyophilized powder. The 10 mM batch of 4ISIYTSD$_{10}$ (SEQ ID NO:8) peptide was titrated into $CXCL12_{WT}$ and $CXCL12_2$ and the 15 mM batch was titrated into $CXCL12_1$. $CXCL12_{WT}$ and $CXCL12_2$ chemical shift assignments ($^1$H and $^{15}$N) were acquired from previously published sources (BMRB ID 16145 and 15633, respectively).

Peptides were titrated into CXCL12 samples and monitored by $^1$H-$^{15}$N Heteronuclear Single Quantum Coherence (HSQC) experiments. Total peptide additions differed for individual peptide titrations but ranged from 0-160 equivalencies. Spectra were processed using in-house scripts and chemical shift tracking was performed using CARA software. Combined $^1$H/$^{15}$N chemical shift perturbations were calculated as $((5 \Delta\delta_H)^2+(\Delta\delta_{NH})^2)^{0.5}$, where $\delta_H$ and $\delta_{NH}$ are the amide proton and nitrogen chemical shifts, respectively. Equilibrium dissociation constants ($K_d$) were determined by non-linear fitting of the combined $^1$H/$^{15}$N$_H$ chemical shift perturbations as a function of peptide concentration to a single-site quadratic equation. For a given interaction, residues with the largest chemical shift perturbations were fitted individually. The resulting $K_d$ values and their respective fitting errors were then averaged to produce the reported affinity and standard deviation for that interaction.

Peptide HPLC purfication. HPLC was performed on a Waters 600E multisolvent delivery system with a Waters U6K injector, Waters 490E programmable multi-wavelength detector operating at 230 nm, Waters busSAT/IN module and Waters Empower 2 software. Separation was achieved on a Sunfire™ SemiPrepC$_{18}$ OBS™ column (5 µm, 150×19 mm ID) at a flow rate maintained at 7.0 mL min$^{-1}$, or on a Sunfire™ SemiPrepC$^{18}$ OBS™ column (5 µm, 250×10 mm ID) at a flow rate maintained at 4.0 mL min$^{-1}$. Method A. Separation of non-sulfated peptides and neopentyl-protected sulfopeptides involved a mobile phase of 0.1% TFA in water (Solvent A) and 0.1% TFA in acetonitrile (Solvent B) using a linear gradient from 0% to 100% solvent B. Method B: Separation of unprotected sulfopeptides involved a mobile phase of 0.1 M $NH_4OAc$ (Solvent C) and 100% acetonitrile (Solvent D) using the stated linear gradient.

Peptide synthesis—Loading of amino acid onto Rink Amide resin. Solid-phase synthesis was carried out in poly-propylene syringes equipped with Teflon filters, purchased from Torviq. Rink Amide resin (resin capacity 0.74 mmol g$^{-1}$) (200 µmol) was initially washed with DMF (5×5 mL), DCM (5×5 mL) and DMF (5×5 mL), then allowed to swell in DMF (5 mL) for 30 min. The resin was drained and treated with a solution of piperidine/DMF (2×5 mL, 1:9 v/v) and gently agitated for 5 min. The resin was then washed sequentially with DMF (5×5 mL), DCM (5×5 mL) and DMF (5×5 mL). The efficiency of the deprotection was determined by measurement of the fulvene-piperidine adduct at λ=301 nm (see below). A solution of protected amino acid (800 µmol), PyBOP (416 mg, 800 µmol) and NMM (16 µL, 800 µmol) in DMF (8 mL) was added to the resin and the resulting suspension was gently agitated for 2 h. At this time the resin was drained and washed with DMF (5×5 mL), DCM (5×5 mL) and DMF (5×5 mL). A mixture of acetic anhydride/piperidine (5 mL, 1:9 v/v) was then added to the resin and agitated for 10 min. The resin was subsequently drained and washed with DMF (5×5 mL), DCM (5×5 mL) and DMF (5×5 mL).

Peptide synthesis—Estimation of resin loading. The N-terminal Fmoc protecting group was removed according to the procedure described above and the combined drained Fmoc deprotection solutions were diluted with a solution of piperidine/DMF (1:9 v/v) so that the maximum concentration of the fulvene-piperidine adduct was in the range of 2.5–7.5×10$^{-5}$ M. A sample of this solution (2×3 mL) was transferred to two matched 1 cm quartz glass cuvettes and the UV-Vis absorbance at λ=301 nm was measured using the solution of piperidine/DMF (1:9 v/v) as a reference. An average of the two absorbance values were used to calculate the resin loading using e=7800 M$^{-1}$ cm$^{-1}$ Peptide synthesis—Iterative Fmoc-strategy peptide assembly (100 µmol). N-terminal Fmoc deprotection: A solution of piperidine/DMF (2×5 mL, 1:9 v/v) was added to the resin and agitated for 5 min. the resin was subsequently drained and washed with DMF (5×3 mL), DCM (5×3 mL) and DMF (5×3 mL). The resulting resin-bound amine was used immediately in the next peptide coupling step. The efficiency of the previous amino acid couplings were determined by measurement of the resulting fulvene-piperidine adduct at λ=301 nm, as described above. Amino acid coupling: a solution of Fmoc-protected amino acid (100

µmol), PyBOP (208 mg, 400 µmol) and NMM (22 µL, 200 µmol) in DMF (1 mL) was added to the resin and the resulting suspension was gently agitated for 1 h. The resin was then drained and washed sequentially with DMF (5-3 mL), DCM (5-3 mL), and DMF (5×3 mL). Fmoc-Tyr(SO$_3$nP)-OH (prepared as described previously (35, 36)), was coupled using 1.5 equiv. of the modified amino acid, PyBOP (1.5 equiv.) and NMM (3 equiv.) in DMF (1 mL), and the suspension was gently agitated for a minimum of 4 h. Capping: a mixture of acetic anhydride/pyridine (2×5 mL, 1:9 v/v) was added to the resin and agitated at room temperature for 5 min. At this time the resin was drained and washed with DMF (5×3 mL), DCM (5×3 mL) and DMF (5×3 mL). Final N-terminal Fmoc deprotection and acetylation: the fully assembled resin bound peptide was treated with piperidine/DMF (2×5 mL, 1:9 v/v) and agitated for 5 min, The loading was determined by measuring the absorbance of the fulvene-piperidine adduct at $\lambda$=301 nm. The N-terminus was subsequently acetylated by treatment with a mixture of acetic anhydride/pyridine (5 mL, 1:9 v/v) for 5 min and the resin subsequently washed with DMF (10×3 mL) then DCM (10×3 mL).

Peptide synthesis—General procedure for cleavage of peptides and protected sulfopeptides from resin. A mixture of TFA/triisopropylsilane/water (3 mL, 90:5:5 v/v/v) [or TFA/triisopropylsilane/water/thioanisole (3 mL, 85:5:5:5 v/v/v/v) for peptides containing methionine residues] was added to the resin and the resulting suspension gently agitated for 2 h. The resin was then drained and washed with TFA (3×3 mL) and the combined cleavage/washing solutions were concentrated under reduced pressure. The resulting residue was dissolved in water (2 mL) with dropwise addition of MeCN to facilitate dissolution. Purification by preparative reverse-phase HPLC (method A) and concentration of the appropriate fractions provided the desired peptides and neopentyl-protected sulfopeptides.

Peptide synthesis—General procedures for deprotection of neopentyl protected sulfopeptides. Method A: Neopentyl-protected sulfopeptides (100 µmol) were dissolved in 1 M NH$_4$OAc solution (~2 mL/10 mg peptide) and the resulting mixture was incubated at 310 K for 24 h. At this time, the reaction mixture was purified by preparative reverse-phase HPLC (Method B). Lyophilization of the appropriate fractions provided the desired free sulfopeptides. Lyophilization was performed three times until a constant weight was achieved suggesting complete removal of residual NH$_4$OAc. Method B: To a solution of neopentyl protected sulfopeptide (100 µmol) in a mixture of DMF/DMSO (~1 mL/10 mg peptide, 3:1 v/v) was added sodium azide (1000 µmol) and the resulting mixture was stirred at 338 K for 12 h under an atmosphere of nitrogen. The reaction mixture was subsequently purified by preparative reverse-phase HPLC (Method B). Lyophilization of the appropriate fractions provided the desired sulfopeptides. The sulfopeptides were resuspended in MilliQ water and lyophilized three times to remove residual NH$_4$OAc.

Fluorescence polarization assay. Fluorescence polarization (FP) assays were performed on a PTI spectrofluorometer equipped with automated polarizers, using a time base polarization method provided by the program Felix32. Lyophilized CXCL12$_{WT}$ was reconstituted in H$_2$O and diluted to appropriate concentrations in a 25 mM MES (pH 6.8) buffer, filtered and degassed. $^{18}$SGDsYDSM$_{24}$ (SEQ ID NO:4) peptide and sulfotyrosine (Tyr-SO$_3$H) stocks were prepared separately at 25 mM and 500 mM, respectively, in a 25 mM MES (pH 6.8) buffer, filtered and degassed. Experiments were performed at 298 K and intrinsic tryptophan fluorescence was observed with emission and excitation wavelengths of 325 nm and 295 nm, respectively. FP was monitored as a function of increasing CXCL12$_{WT}$ concentration (10, 25, 50, 75, 100, 250, 500, 750, 1000 and 1500 µM) alone or in the presence of 3 mM $^{18}$SGDsYDSM$_{24}$ (SEQ ID NO:4) or 50 mM sulfotyrosine. The CXCL12$_{WT}$ dimerization equilibrium dissociation constant (K$_d$) was determined by non-linear fitting to a three-parameter function as previously described. Experiments were performed in duplicate and the reported dimerization K$_d$ values reflect the average of both experiments.

Cell culture. Chinese hamster ovary K1 (CHO-K1) cells, stably transfected with the Gα15 gene in pcDNA3.1+, were cultured in a 1:1 mixture of Dulbecco's modified Eagle medium (DMEM) with Glutamax (Gibco):F12 nutrient mixture (Gibco) supplemented with 10% (w/v) fetal bovine serum (FBS) (Gibco). Stable expression of the Gα15 transgene was maintained by further supplementing the growth medium with 700 µg ml$^{-1}$ geneticin (Gibco).

Transfections. For transient transfections with the Flag-CXCR4 WT and N-terminally mutated constructs, the CHO-K1 Gα15 stable cells were lifted using 0.25% (v/v) trypsin-EDTA (Gibco), and 2×10$^6$ cells were re-plated onto 10 cm culture dishes. To increase transfection efficiency, 0.25% (v/v) DMSO was added to the media when the cells were plated, and no geneticin was present in the plating medium. The cells were transfected 24 hours later using the Mirus TransIT-CHO Transfection Kit according to the manufacturers protocol, with the following exceptions: the amount of CHO transfection reagent was scaled up to 4 µl µg$^{-1}$ of DNA in the transfection mixtures, and the amount of CHO mojo reagent was scaled up to 1 µl µg$^{-1}$ of DNA in the mixtures. Immediately before transfection, the medium was replaced with a 1:1 mixture of DMEM with Glutamax:F12 nutrient mixture supplemented with 10% (w/v) FBS (without DMSO or geneticin).

Calcium flux. 24 hours after plating, the medium was removed and the cells were washed with 5 ml PBS. The adherent cells were then incubated for 10 minutes in 3 ml of Cellstripper non-enzymatic cell dissociation solution (Cellgro). Cells were then suspended by pipetting, washed twice in Calcium Flux Buffer (Hanks Balanced Salt Solution supplemented with 20 mM HEPES) supplemented with 0.1% (w/v) bovine serum antigen (BSA) and 4 mM probenecid (Invitrogen). Each washing was carried out by centrifuging the cells at 350×g and then re-suspending in Calcium Flux Buffer. After washing, the cell concentrations were normalized between samples and the cells were plated at 2.5×10$^5$ cells/well in poly-D-lysine coated 96 well plates (Becton Dickinson Labware). FLIPR 4 Calcium Flux assay kit dye (Molecular Devices) was then added to each well, such that the ratio of dye to cell suspension was 1:1. The plates were then centrifuged for 3 minutes at 250×g to ensure the cells settled onto the surface of the plates. The plated cells were incubated at 310 K for 90 min. Fluorescence was measured at 310 K using a FlexStation2 Microplate Reader with excitation and emission wavelengths at 485 nm and 515 nm, respectively. After an 18 s baseline measurement, the indicated concentrations of CXCL12 were added and the resulting calcium response was measured for an additional 50 s. Fluorescence as a function of CXCL12 concentration was fitted to a four-parameter equation. Data are representative of two experiments each performed with three replicates. CXCR4 variants with EC$_{50}$ or maximum calcium response values more than three standard deviations from the mean CXCR4$_{WT}$ quantities were deemed significant.

Flow cytometry. For testing receptor surface expression, $3\times10^5$ cells were set-aside during the calcium flux assay preparations. The cells were then washed twice with PBS containing 0.5% BSA (w/v) (FACS buffer). Staining was carried out in a 50× dilution of either anti-DDDDK or mouse IgG1 isotype control conjugated to SureLight APC (Columbia Biosciences) for 45 minutes on ice. Cells were then washed 3× in FACS buffer before analysis, which was carried out using a Guava bench top mini-flow cytometer.

Example 2: Complex Structure of Chemokine-GPCR N-Terminus: Insight into CXCL12 Biased Agonism Chemokines are ubiquitous in the directed migration of cells for development, immune surveillance and disease. Approximately twenty receptors and more than twice that number of chemokine ligands create a complex system to regulate the appropriate physiologic response. The network is further complicated by receptor and ligand promiscuity, and more recently the discovery of biased agonism. The receptor CXCR4 recognizes both monomeric and dimeric forms of the chemokine CXCL12, but the structural mechanism for biased agonism remains unclear. We solved the structure of a 1:1 complex between CXCL12 and the CXCR4 N-terminus and observed a monomer-specific interaction that is required for receptor activation. Measurements of CXCL12-dependent arrestin recruitment, receptor modification, trafficking and degradation, cell migration and apoptotic cell death revealed distinct CXCR4 activation profiles that correlate with binding of the monomeric balanced agonist or dimeric arrestin-biased agonist.

The last decade witnessed major revisions to the classic model of G protein-coupled receptor (GPCR) signaling. Instead of a single type of agonist-driven intracellular response, different ligands can stabilize distinct active states in the same receptor to shift the balance of functional outputs. The predominant modes of GPCR signaling originate with GTPase activation and β-arrestin recruitment, and agonists can selectively activate one ('biased agonists') or both ('balanced agonists') pathways. In the chemokine family where receptor and ligand promiscuity is common, biased agonist GPCR signaling adds another layer of complexity to the in vivo orchestration of cell migration. Originally discovered as leukocyte chemoattractants that promote inflammation and direct the trafficking of immune cells, the biological responsibilities of chemokines include organogenesis, neurogenesis, would healing, and cardioprotection. In a family of more than 50 chemokines and 19 receptors, the chemokine CXCL12 (Stromal cell-derived factor-1; SDF-1) and its receptor CXCR4 have been the focus of intense study for over two decades. CXCL12 and CXCR4 are essential in developmental and housekeeping roles but also participate in numerous pathologies including HIV infection and more than 23 different types of cancer. Despite numerous efforts to inhibit CXCL12/CXCR4 signaling, only one antagonist, AMD3100, is currently approved for clinical use. A better pharmacological understanding based on GPCR-ligand structure-function relationships is needed as a foundation for next-generation discovery research on this important therapeutic target.

Chemokine signaling is initiated by formation of an extensive protein-protein interface segregated into two distinct regions. First, the receptor N-terminus wraps around the folded chemokine domain and contributes most of the binding energy (site 1), and soluble chemokine-receptor complexes corresponding to the site 1 interaction have been analyzed by NMR (REFS). Subsequent docking of the flexible chemokine N-terminus into a pocket within the transmembrane domain activates receptor signaling (site 2). X-ray crystal structures of inhibitor-bound CXCR4 reveal the large orthosteric pocket but lack electron density for the receptor N-terminus. Thus, no structure of an intact, active chemokine-receptor complex has been solved.

Like most chemokines, CXCL12 forms dimers at high concentrations (Veldkamp 2006, and www.ncbi.nCXCL121.nih.gov/pubmed/17075134), when crystallized, or when bound to extracellular matrix glycosaminoglycans, but is presumed to bind CXCR4 as a monomer at chemotactic concentrations (~10 nM). However, we found that peptides derived from the CXCR4 N-terminus bind the CXCL12 monomer and also form a dimeric 2:2 complex at higher concentrations. We subsequently showed that preferentially-monomeric and constitutively-dimeric CXCL12 variants activate distinct intracellular signaling and migration profiles, a unique example of biased agonism arising from a change in oligomeric state of the ligand. Some of the contacts observed in the dimeric CXCL12-CXCR4$_{1-38}$ NMR structure would be absent in a monomeric complex, suggesting that distinct monomer- and dimer-specific contacts at the CXCL12-CXCR4 site 1 interface contribute to biased signaling.

To examine the structural basis for biased CXCR4 agonism, we solved the structure of a monomeric CXCL12 variant (CXCL12$_1$) bound to the N-terminal domain of CXCR4 (CXCR4$_{1-38}$). Apolar residues near the CXCR4 N-terminus dock into a cleft on the CXCL12 monomer that is inaccessible in the dimer, and this monomer-specific interaction is essential for full receptor activation. Functional comparisons of receptor activation by constitutively monomeric and dimeric ligands show that only the CXCL12 monomer induces CXCR4 phosphorylation at Ser 324 and Ser 325, ubiquitination, and degradation as well as the induction of apoptotic cell death. These results suggest that the two-site model for chemokine receptor activation must evolve to account for ligand-biased agonism arising from alternative site 1 interfaces.

CXCL12$_1$ binds and activates the CXCR4 chemokine receptor. For nearly two decades, the CXCL12 quaternary structure relevant to receptor activation has been debated. We and others have shown that CXCL12 exists in a solution-dependent dimer equilibrium that effects binding to glycosaminoglycans, receptor recognition and ultimately modulates intracellular signaling. Subsequent studies attempting to deconvolute the effects of dimerization have compared constitutively dimeric CXCL12 (CXCL12$_2$) to either wildtype (CXCL12$_{WT}$) or a preferential-monomer. We recently engineered a CXCL12 variant that remains strictly monomeric at millimolar concentrations (CXCL12$_1$).

Figure 10A:
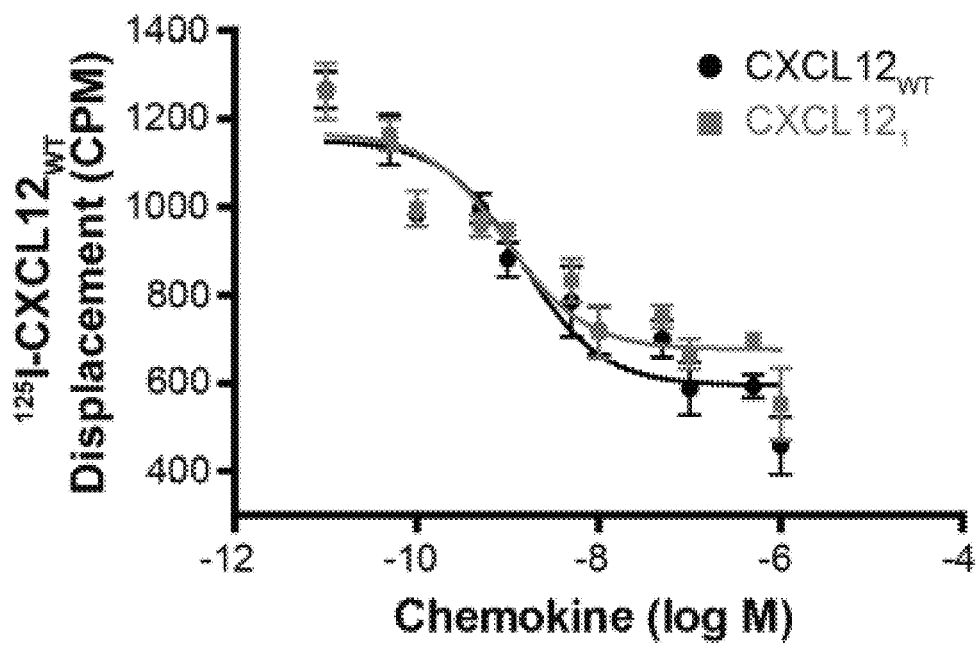
FIG. 10A. $CXCL12_1$ enhances CXCR4-mediated calcium flux, migration, and arrestin recruitment. The affinities of CXCL12 variants for CXCR4 were determined by $^{125}I$-CXCL12 displacement. $K_d$ values for binding of $CXCL12_{WT}$ and $CXCL12_1$ were calculated as $1.4\pm1.5$ nM and $0.97\pm1.5$ nM, respectively, from their corresponding $logEC_{50}$ values of $-8.867\pm0.08$ and $-8.459\pm0.06$.
Figure 10B:
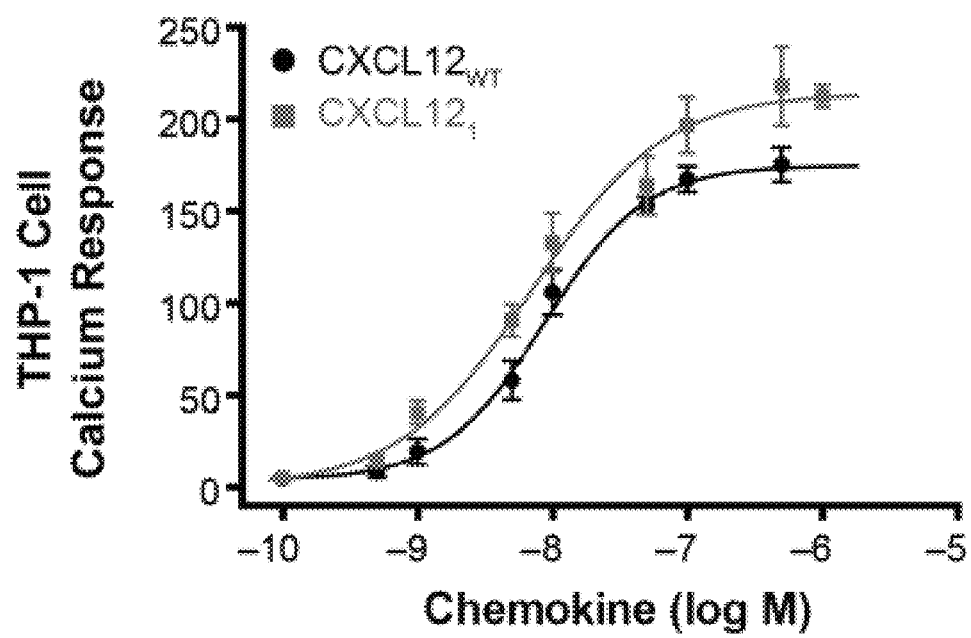
FIG. 10B. $CXCL12_1$ induced a CXCR4-mediated calcium response with an $EC_{50}=7.1\pm1.3$ nM similar to the $CXCL12_{WT}$ $EC_{50}=8.7\pm1.7$ nM.

Here, we tested whether the affinity of CXCL12$_1$ for full-length CXCR4 differed from CXCL12$_{WT}$. Radioligand displacement using CXCR4 cell membrane preparations yielded similar affinities for CXCL12$_{WT}$ and CXCL12$_1$ of 1.44±1.5 nM and 0.97±1.5 nM, respectively (FIG. 10A). We established the functional activity of CXCL12$_1$ as a CXCR4 agonist by measuring its ability to mobilize intracellular calcium, a sensitive indicator of chemokine receptor-mediated G protein activation. CXCL12$_1$ produced a robust calcium flux response with a potency equivalent to CXCL12$_{WT}$ (FIG. 10B).

Figure 10C:
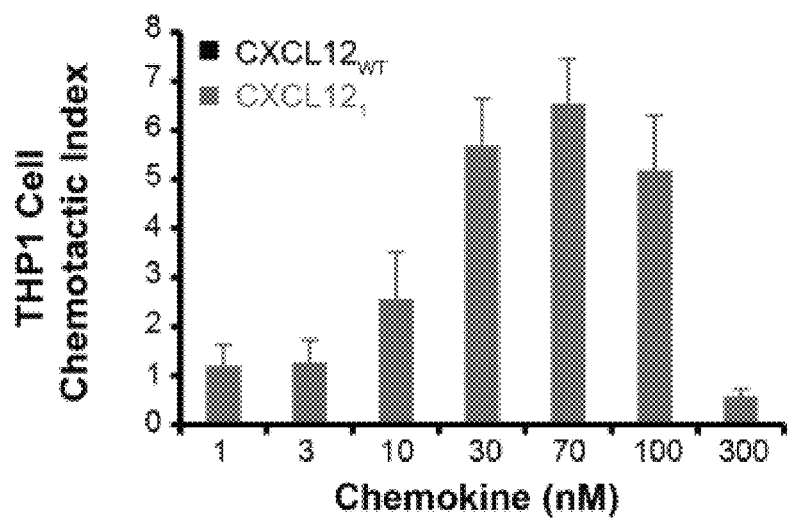
FIG. 10C. THP-1 cell chemotaxis was quantified after 3 h stimulation. The chemotactic index was calculated by normalizing the number of cells that migrated toward the stimulus to the number that migrated in the absence of stimulus.
Figure 10D:
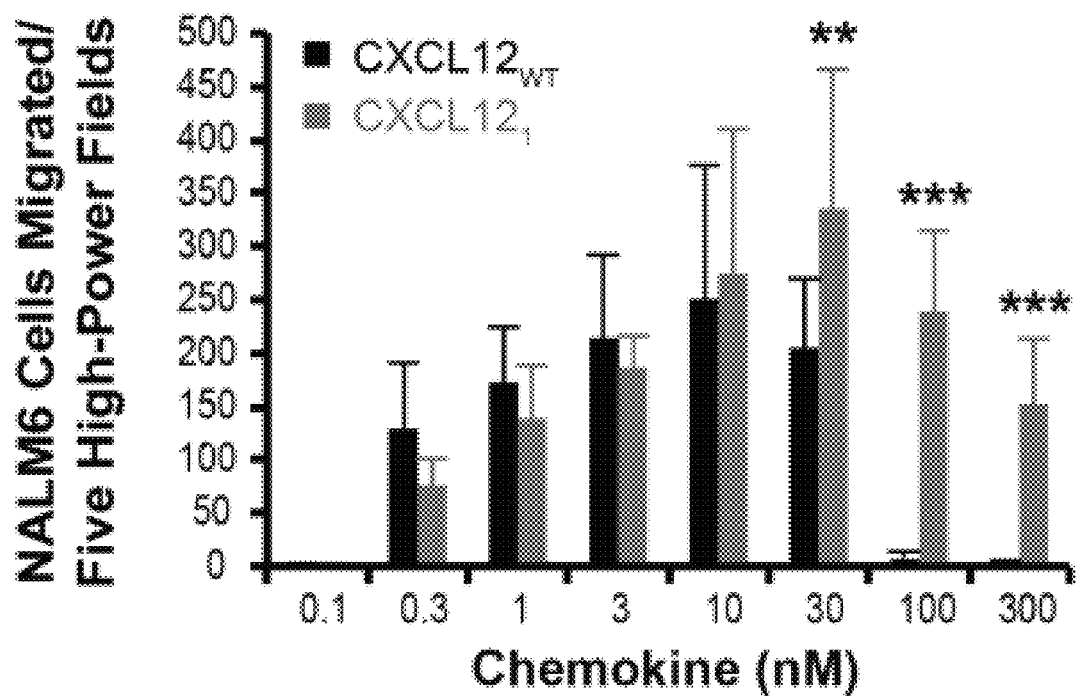
FIG. 10D. NALM6 cell migration was quantified after 90 min stimulation. Chemotaxis was determined from counting the number of migrated cells in five high power magnification fields.
Figure 10E:
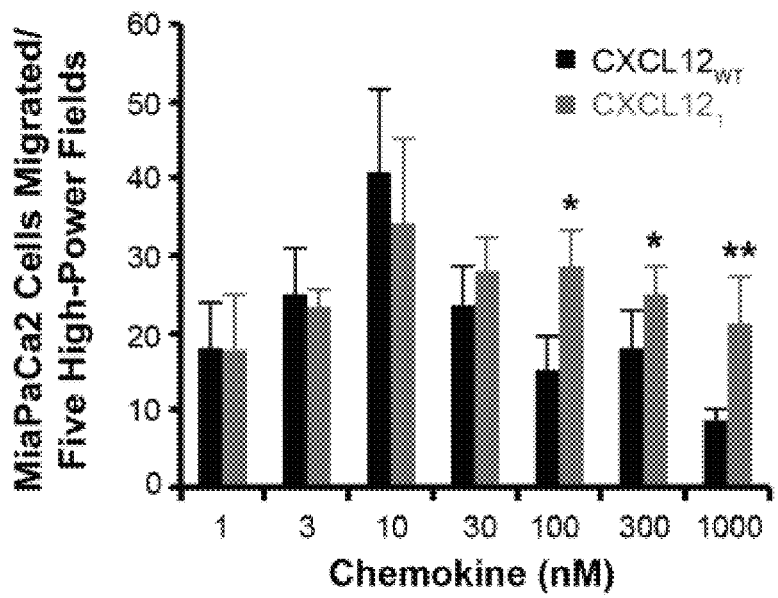
FIG. 10E. Migration of MiaPaCa2 was monitored after 6 h stimulation using Transwell migration chambers. Chemotaxis was determined from counting the number of migrated cells in five high power magnification fields.

CXCL12$_1$ has enhanced migratory capacity. CXCL12, like all chemokines, promotes a bell-shaped migratory response over a narrow concentration range. Although the mechanism is unclear, we suggested that the CXCL12 monomer-dimer equilibrium might be partially responsible for the narrow dose response. Whereas $CXCL12_2$ does not promote chemotaxis at any concentration, a preferentially monomeric CXCL12 variant produces a bell-shaped response over an extended concentration range. Because $CXCL12_1$ is incapable of dimerization, we tested if it generated a sigmoidal or biphasic migratory response. The chemotaxis of THP-1 monocytes, NACXCL1216 pre-B cells, and MiaPaCa2 pancreatic cancer cells was tested using Boyden or Transwell migration chambers (FIG. 10C-E). $CXCL12_1$ extended the effective dose at least 10-fold in all cell types but, nonetheless, still signaled migratory arrest.

Figure 10F:
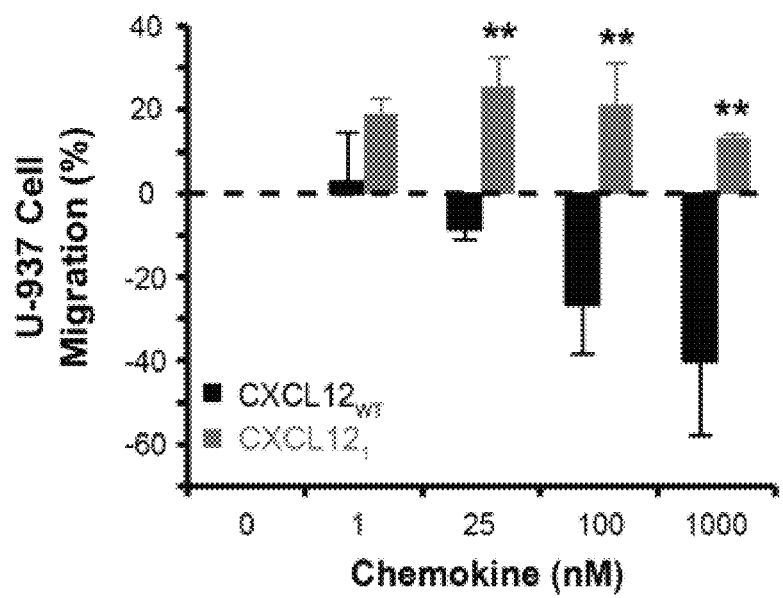
FIG. 10F. U-937 cells were confined to a 1 µl agarose droplet and migration was observed following 18-24 h incubation with test media containing $CXCL12_{WT}$ or $CXCL12_1$. Migration inhibition presented as mean±SD with chemokine-free control normalized to zero.

To assess how CXCR4 activation was interpreted in the presence of other migratory signals, U-937 leukemia cells confined to an agarose droplet were incubated in serum-containing media with increasing CXCL12 concentrations. $CXCL12_1$ significantly enhanced migration at all tested concentrations (FIG. 10F). Qualitatively, $CXCL12_1$ exhibits a bell-shaped dose response with a peak enhancement at 25 nM. In stark contrast, $CXCL12_{WT}$ prompted dose-dependent migratory arrest at nearly all concentrations with maximal inhibition of 40.1 t 18% (FIG. 10F).

Figure 10G:
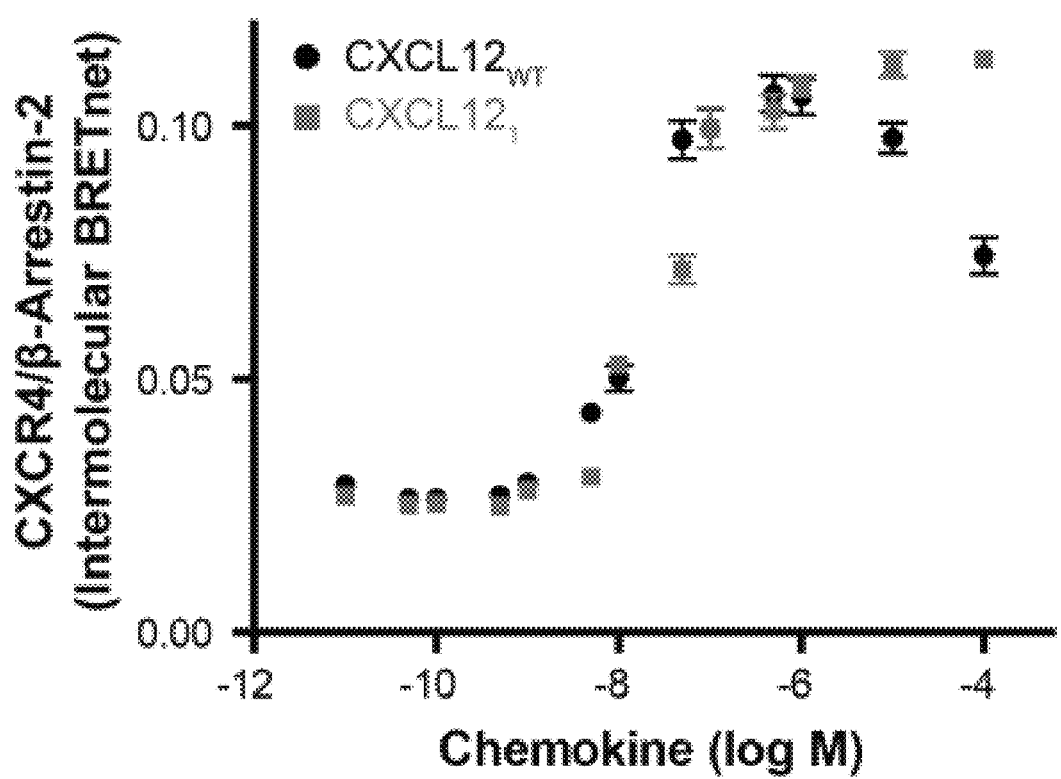
FIG. 10G. HEK293 cells transiently co-expressing β-arrestin-2-RLuc as a BRET donor and CXCR4-YFP as BRET acceptor were stimulated with increasing chemokine concentrations resulting in $EC_{50}$ values of $17.6\pm1.1$ nM for $CXCL12_{WT}$ and $30.6\pm1.1$ nM for $CXCL12_1$. $CXCL12_{WT}$ and $CXCL12_1$ responses were compared at each dose by two-tailed T-test (*, p<0.01; , p<0.01; *, p<0.001).

CXCR4-mediated chemotaxis is dependent upon β-arrestin recruitment and filamentous actin cytoskeleton rearrangement. Consistent with its non-migratory phenotype, $CXCL12_2$ produces little arrestin recruitment or F-actin formation. In contrast, $CXCL12_{WT}$ and $CXCL12_1$ recruit β-arrestin-2 to CXCR4 with similar potency and efficacy (FIG. 10G). Interestingly, as concentrations were increased to 10 and 100 µM $CXCL12_{WT}$ induced a bimodal recruitment of β-arrestin-2 that parallels the chemotactic dose response. As $CXCL12_1$ is incapable of dimerization, our data suggests that ligand-receptor stoichiometry, independent of the chemokine quaternary structure, may govern CXCR4 signaling.

Figure 12A:
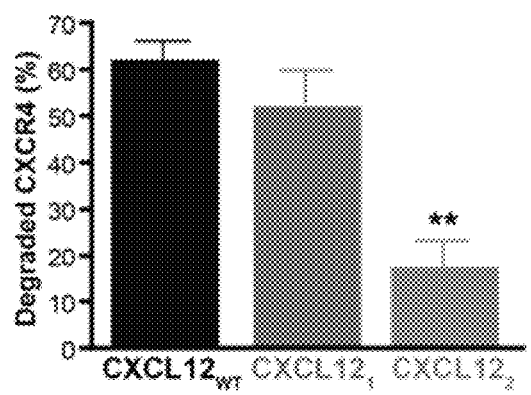
FIG. 12A. CXCL12 tertiary structure controls CXCR4 fate and function. HeLa cells were stimulated with vehicle or 80 ng/ml CXCL12 variants for 2 h. Endogenous CXCR4 receptor levels were determined by SDS-PAGE followed by immunoblotting with an anti-CXCR4 antibody. Bars represent the mean CXCR4 degraded±S.E.M., n=3.
Figure 12B:
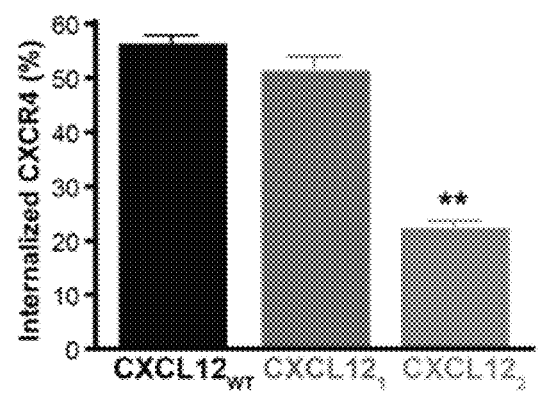
( FIG. 12B. HeLa cells were stimulated with vehicle or 80 ng/ml CXCL12 variants for 20 min. Cells were stained with a PE-conjugated anti-CXCR4 antibody or isotype control antibody, and endogenous CXCR4 surface expression was analyzed by flow cytometry. Bars represent the mean CXCR4 internalized±S.E.M., n=3.

The structure of $CXCL12_1$ in complex with $CXCR4_{1-38}$. The dimeric CXCR4 crystal structures reinforce the hypothesis that ligand-receptor occupancy may modulate CXCR4 signaling bias. In the two-step, two-site model for chemokine receptor activation, CXCL12 first binds to the N-terminus of CXCR4. Our recent 2D NMR studies suggest that the $CXCL12_1$:$CXCR4_{1-38}$ interface is partially distinct from the 2:2 site 1 interaction. We used HSQC titrations to confirm the 1:1 interaction. Increasing $CXCL12_{WT}$ concentrations caused $CXCR4_{1-38}$ resonances to shift in curved trajectories suggesting the simultaneous presence of both a 1:1 and 2:2 complexes. Titrating CXCL12 variants into [U-$^{15}$N]-$CXCR4_{1-38}$ produced chemical shift perturbations consistent with unique chemical environments for CXCR4 residues 1-13 (FIG. 12B).

Figure 16A:
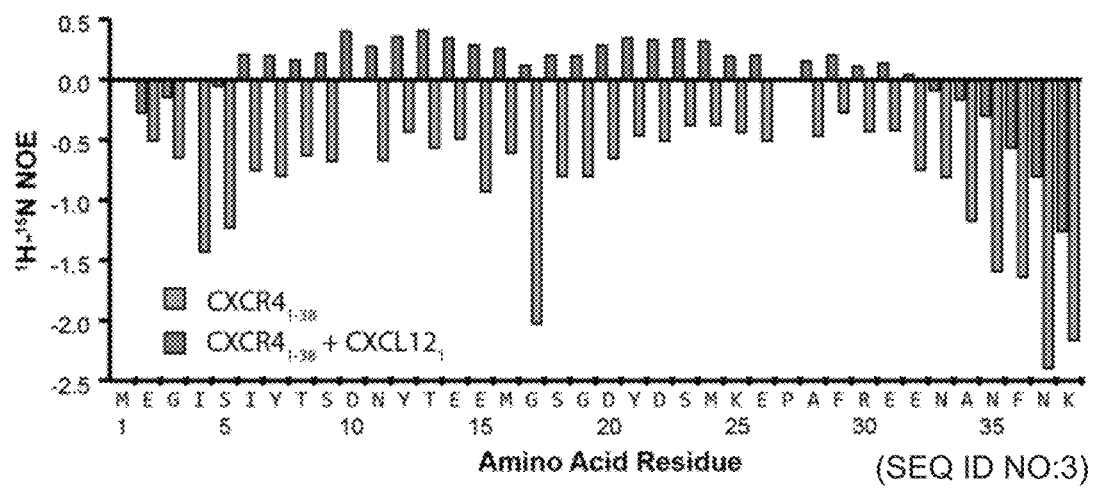
FIG. 16A. CXCL12$_1$ and CXCL12$_2$ interact disparately with the CXCR4 N-terminus. $^1$H/$^{15}$N heteronuclear NOE experiment of 250 µM [U-$^{15}$N]-CXCR4$_{1-38}$ in the absence (orange) and presence (green) of 500 µM CXCL12$_1$. CXCR4$_{1-38}$ residues 4-7 exhibit a more stable interaction with CXCL12$_1$ than with CXCL12$_2$.
Figure 16B:
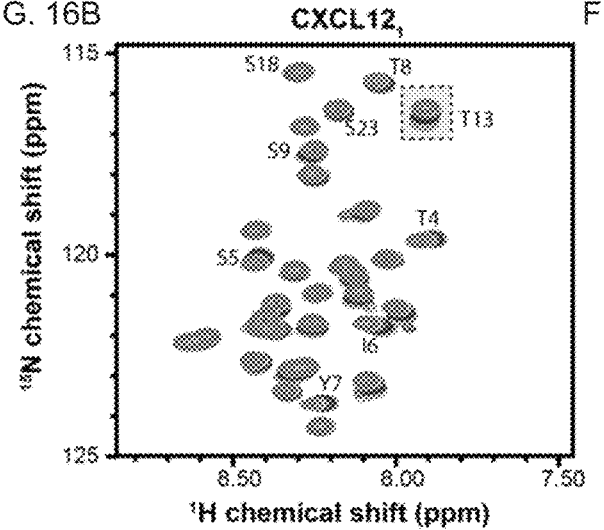
FIG. 16B. 2D $^1$H/$^{15}$N HSQC spectra of [U-$^{15}$N]-CXCR4$_{1-38}$ in 25 mM d-MES (pH 6.8) titrated with increasing concentrations (orange to green) of CXCL12$_2$).
Figure 16C:
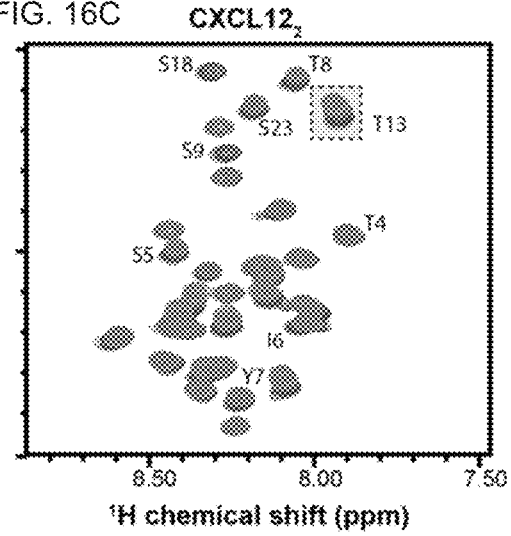
FIG. 16C. 2D $^1$H/$^{15}$N HSQC spectra of [U-$^{15}$N]-CXCR4$_{1-38}$ in 25 mM d-MES (pH 6.8) titrated with increasing concentrations (orange to green) of CXCL12$_2$).
Figure 16D:
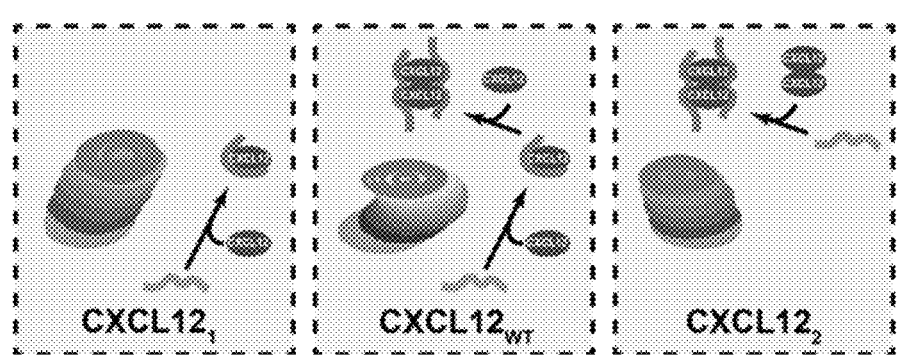
FIG. 16D. CXCL12$_1$ and CXCR12$_2$ perturb CXCR4$_{1-38}$ distinctly. In some instances, as illustrated with T13, the direction of their perturbations can be concatenated to produce CXCL12$_{WT}$ perturbation trajectories.

In contrast to previously published spectra of $CXCL12_{WT}$, all peaks in the N-terminus were visible throughout the titration and traversed linear paths. Concentration of the linear trajectories recreates the complicated chemical shifts induced by $CXCL12_{WT}$ and underscores the physiologic validity of both the $CXCL12_1$ and $CXCL12_2$ variants (FIG. 16B). To assess the rigidity of $CXCR4_{1-38}$ upon chemokine binding we measured $^1H$-$^{15}N$ heteronuclear NOE values, which reflect the backbone flexibility for each residue on picosecond to nanosecond timescales. When bound to the $CXCL12_2$ dimer, $CXCR4_{1-38}$ residues 5-10 remain relatively dynamic and imply a weak, transient interaction. $CXCL12_1$ stabilizes the high frequency motions of $CXCR4_{1-38}$ residues 5-10 (FIG. 16A).

Figure 14A:
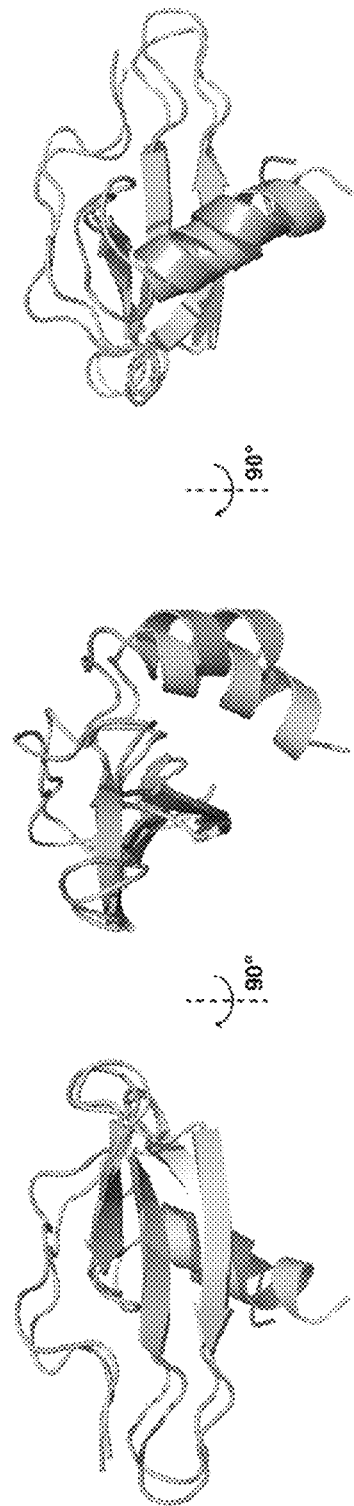
FIG. 14A. The α-helix angle of CXCL12$_1$ is inconsistent with dimerization. CXCL12$_1$ residues 9-49 aligned to respective residues of PDB ID 1SDF with a backbone RMSD=1.6 Å.
Figure 14C:
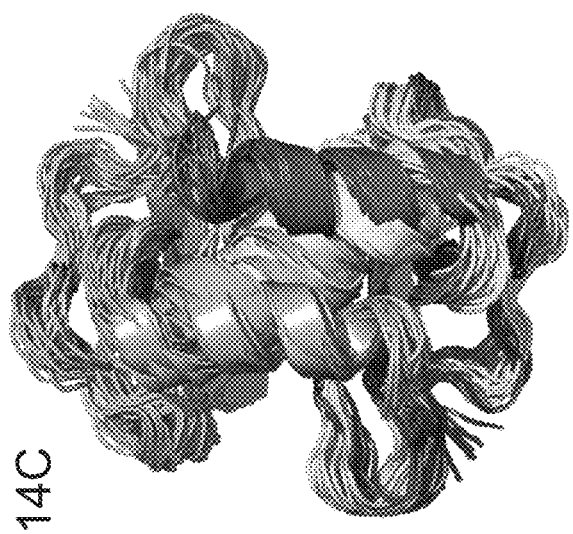
FIG. 14C. Two CXCL12$_1$ molecules (cyan and yellow) are aligned with each protomer of the CXCL12$_2$ NMR structure (PDB ID 2K05) with the entire 20 model ensemble visible.
Figure 14B:
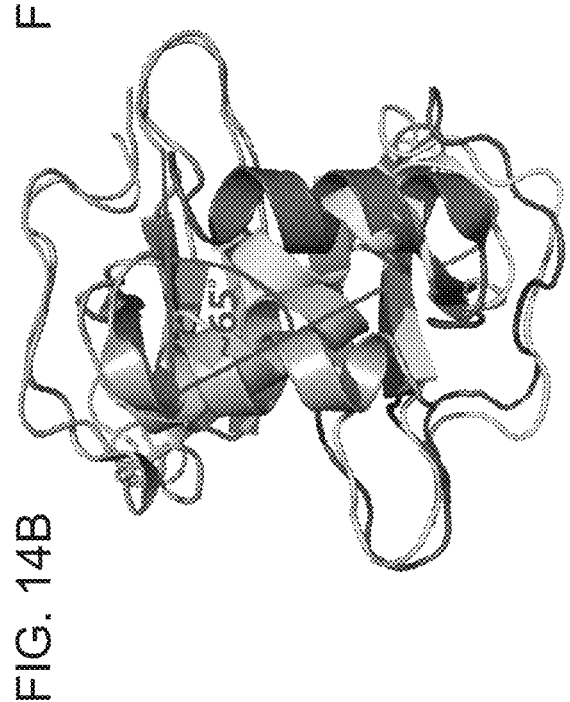
FIG. 14B. Two CXCL12$_1$ molecules (cyan and yellow) are aligned with each protomer of the CXCL12$_2$ NMR structure (PDB ID 2K05). The alignments possess backbone RMSD of 1.41 Å and 1.37 Å. The α-helices of the two CXCL12$_1$ molecules possess and average angle of 65°, relative to the β-sheet, and would sterically clash in this orientation.

To understand how the CXCR4 N-terminus recognizes $CXCL12_1$, we determined the complex structure by NMR. A suite of triple-resonance experiments were acquired on samples of [U-$^{13}$C,$^{15}$N]-$CXCL12_1$ saturated with $CXCR4_{1-38}$ and [U-$^{13}$C,$^{15}$N]-$CXCR4_{1-38}$ saturated with $CXCL12_1$ to assign the carbon, nitrogen, and hydrogen resonances. Next, a series of 3D nuclear Overhauser effect (NOE) spectroscopy (NOESY) experiments were collected to identify the position of neighboring hydrogen atoms within a 5 Å distance. As expected, $CXCL12_1$ adopts the canonical chemokine fold comprising a flexible N-terminus, followed by the N-loop, a three-stranded antiparallel β-sheet, and a C-terminal α-helix (FIG. 11). $CXCL12_1$ was designed to mimic the conformation of PDB 1SDF, a CXCL12 solution NMR structure determined in sodium acetate buffer at pH 4.9. In this structure the α-helix maintains a 550 relative to the β-sheet, which would be sterically incompatible with dimerization. As illustrated in FIG. 14, the $CXCL12_1$ α-helix is ~65° relative to the $-sheet and aligns to PDB 1SDF with a backbone RMSD of 1.6 Å.

Determination of the $CXCR4_{1-38}$ contact surface required F1-$^{13}$C-filtered/F3-$^{13}$C-edited NOESY-HSQC experiments to unambiguously identify intermolecular constraints. Intermolecular NOEs, indicative of a stable interaction on the millisecond timescale, were observed from residues 4-27 along the peptide (FIG. 11). Overall, $CXCR4_{1-38}$ adopts a random coil architecture with a short β-strand from Tyr7-Ser9. The position of CXCR1-38 overlaps well with the previously published chemical shift perturbations (FIGS. 11A-C). The ProCys motif (CXCR4 Pro27 and Cys28) is nearly conserved across all chemokine receptors and delineates the flexible N-terminus from the transmembrane portion. Here we observed intermolecular NOEs from both the CXCL12 N-loop and helix to CXCR4 Lys25, Glu26, and Ala28. This constrains CXCR4 Pro27 between the helix and N-loop, marking the point where our NMR data intersects with the recent CXCR4 crystal structure. The Pro27 $C^\alpha$ is translated an average 8.6 Å toward the N-loop compared to the 2:2 complex. Subsequently, the pocket formed by the N-loop and β3 strand, known as the chemokine cleft, is slightly distorted. $CXCL12_1$ residues Glu15-His17 shift toward the β3 strand to accommodate the peptide. $CXCL12_1$ Asn46 puckers away from the pocket allowing Arg47, and to a lesser extent Ans45, to interact with the CXCR4 Tyr21 hydroxyl. The $C^\zeta$ and $C^\alpha$ atoms of Tyr21 are translated an average of 7.0 Å and 5.3 Å, respectively, compared to the 2:2 complex (FIG. 11D). In this position the Tyr21 hydrophobic contacts appear to be primarily satisfied by Val49 and the methylene of Glu15. Upon sulfation, it's reasonable to predict that Lys47, Asn45 or His17 maintain sTyr2l electrostatic interactions with negligible pocket rearrangement.

Figure 15A:
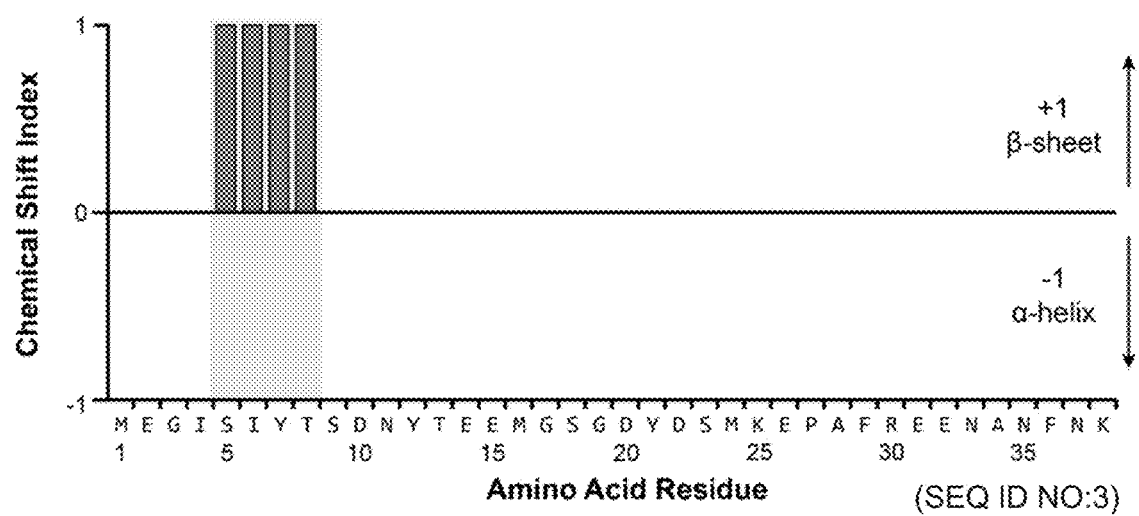
FIG. 15A. CXCR4 residues 7-9 form a fourth β-strand with CXCL12$_1$. Secondary chemical shifts were calculated for CXCR4$_{1-38}$. The consensus of H$^N$, N, C', H$^\alpha$, C$^\alpha$ and C$^\beta$ secondary chemical shifts indicate a short β-sheet comprising residues 5-8.
Figure 15B:
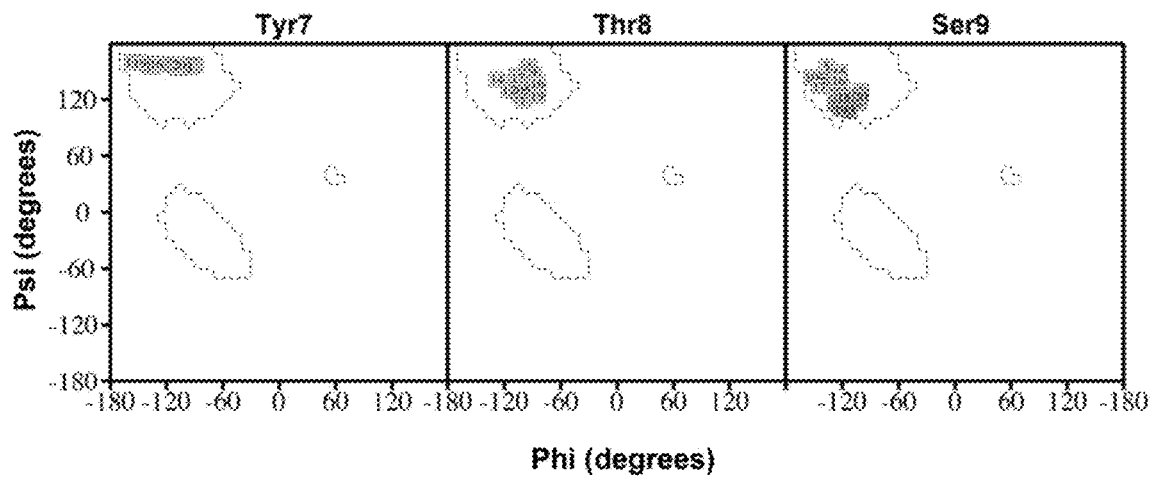
FIG. 15B. The Ramachandran statistics for Tyr7, Thr8, and Ser9 are consistent with a β-sheet.

The 1:1 and 2:2 complex interfaces sharply diverge at residues N-terminal of CXCR4 Tyr12. In the 2:2 complex, CXCR4 Tyr12 makes electrostatic contacts with Lys27 of one $CXCL12_2$ protomer and His25 of the other. Upon sulfation, sTyr12 preferentially forms salt bridges with Lys27 from a single protomer. Tyr7 also makes contacts with the other $CXCL12_2$ subunit by burying into a pocket formed by Val23 and Arg20. In the 1:1 complex Tyr12 buries into a deep cleft formed by Pro10, Lys27, Leu29, and Val 39 that possesses no obvious electrostatic or charge interactions for a sulfated tyrosine. Asp10 and Asn11 of $CXCR4_{1-38}$ then turn to place Tyr7 in close proximity to Tyr12. The Tyr7 hydroxyl is positioned toward His25 and Lys27, but productive contacts are not clear. $CXCR4_{1-38}$ residues Tyr7-Ser9 hydrogen bond with $CXCL12_1$ Ile28-Asn30 to form a four-stranded antiparallel β-sheet (FIG. 11E and FIG. 15).

Figure 11F:
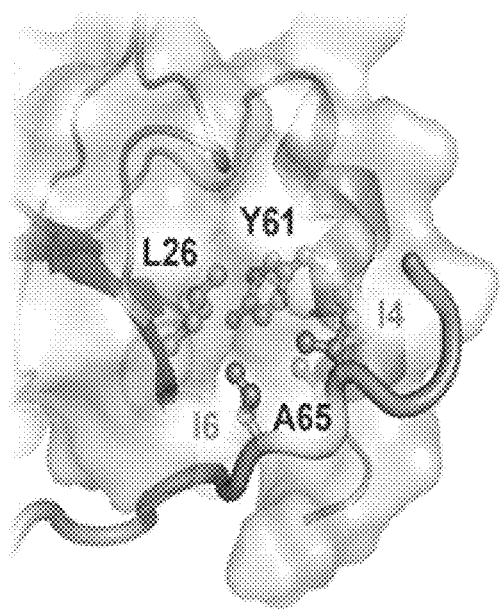
FIG. 11F. CXCR4$_{1-38}$ residues Ile4 and Ile6 pack into a cleft against residues CXCL12$_1$ residues Leu26 and Tyr61.

The position of Tyr7 enables Ile6 to bury into a hydrophobic cleft surrounded by Leu26, Tyr61, and Ala65 (FIG. 11F). Ile4 packs further up the helix against CXCR4 Ile6 and $CXCL12_1$ Leu26, Trp57, and Tyr61. The interaction of hydrophobic CXCR4 residues with the CXCL12 helix is consistent with previous NMR titration studies of $CXCR4_{1-38}$ and cross-saturation NMR experiments with full-length CXCR4. Sulfation of Tyr7 reduces the binding affinity of a CXCR4 Ile4-Asp10 heptapeptide two-fold. The reduced affinity may result from a sulfated Tyr7 straining to interact with Lys27 and displacing the isoleucines from their hydrophobic cleft.

Figure 11G:
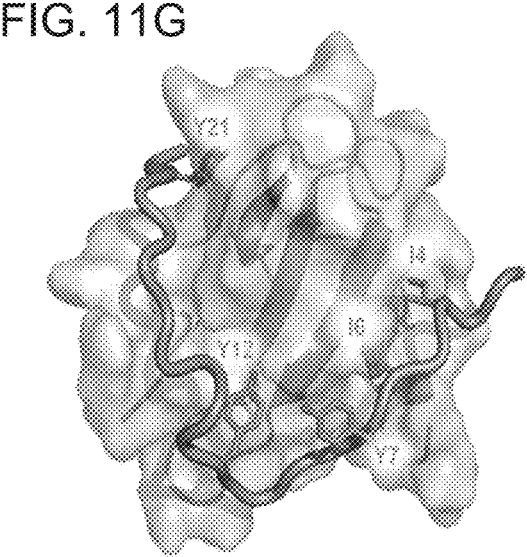
FIG. 11G. CXCL12$_1$:CXCR4$_{1-38}$ complex NMR structures.
Figure 11H:
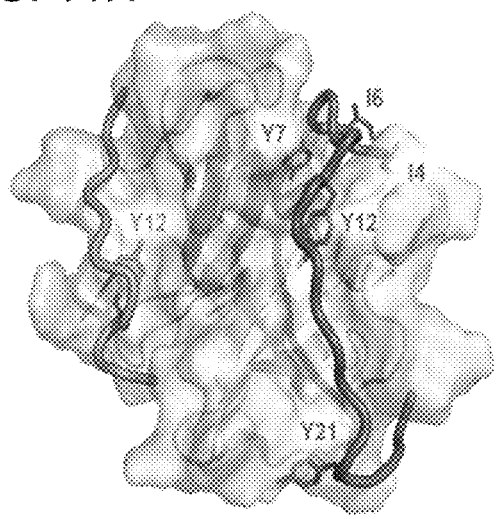
FIG. 11H. CXCL12$_2$:CXCR4$_{1-38}$ complex NMR structures.

The CXCR4 N-terminus is critical for chemokine recognition and activation. The structure of $CXCR4_{1-38}$ in complex with $CXCL12_1$ contains a unique interface for residues 1-12 compared to the $CXCL12_2$:$CXCR4_{1-38}$ complex (FIG. 11G). To assess the contributions of CXCR4 Ile4 and Ile6 to receptor binding and activation, we designed a series of CXCR4 mutants. Ile4 and Ile6 were simultaneously mutated to either alanine or glutamine residues in FLAG-tagged CXCR4. Whereas alanine substitution had no effect on binding affinity, the affinity of $CXCL12_{WT}$ and $CXCL12_1$ for glutamine mutants was reduced 30- and 90-fold, respectively (FIG. 17). Receptor activation was then monitored by the calcium response in CHO-KI cells. Alanine substitutions had no effect on the CXCR4 signaling consistent with an apolar binding interaction (FIG. 17). In contrast, mutation to charged side chains reduce the $EC_{50}$ nearly 10-fold (FIG. 17, Table 2).

TABLE 2

NMR refinement statistics of $CXCL12_1$:$CXCR4_{1-38}$ 20 model ensemble.

| Experimental constraints Distance constraints | |
|---|---|
| Intermolecular | 72 |
| Long | 414 |
| Medium $[1 < (i - j) \leq 5]$ | 241 |
| Sequential $[(i - j) = 1]$ | 441 |
| Intraresidue $[i = j]$ | 365 |
| Total | 1533 |
| Dihedral angle constraints ($\phi$ and $\psi$) | 109 |
| Average atomic R.M.S.D. to the mean structure (Å) $CXCL12_1$ residues 9-66 and $CXCR4_{1-38}$ residues 4-27 | |
| Backbone ($C^\alpha$, C', N) | 3.24 ± 0.73 |
| Heavy atoms | 4.07 ± 0.73 |
| Deviations from idealized covalent geometry | |
| Bond lengths       RMSD (Å) | 0.018 |
| Torsion angle violations    RMSD (°) | 1.4 |
| WHATCHECK quality indicators | |
| Z-score | −3.12 ± 0.27 |
| RMS Z-score | |
| Bond lengths | 0.78 ± 0.03 |
| Bond angles | 0.77 ± 0.02 |
| Bumps | 0 ± 0 |
| Lennard-Jones energy [a] (kJ mol⁻¹) | −2262 ± 99 |
| Constraint violations [b, c] | |
| NOE distance       Number >0.5 Å | 0 ± 0 |
| NOE distance       RMSD (Å) | 0.0196 ± 0.0013 |
| Torsion angle violations    Number >5° | 0 ± 0 |
| Torsion angle violations    RMSD (°) | 0.6474 ± 0.1020 |
| Ramachandran statistics (% of all residues) | |
| Most favored | 73.1 ± 2.9 |
| Additionally allowed | 22.3 ± 3.6 |
| Generously allowed | 2.96 ± 2.0 |
| Disallowed | 1.57 ± 1.2 |

[b] Final X-PLOR force constants were 250 (bonds), 250 (angles), 300 (impropers), 100 (chirality), 100 (omega), 50 (NOE constraints), and 200 (torsion angle constraints).
[c] Nonbonded energy was calculated in XPLOR-NIH.
[d] The largest NOE violation in the ensemble of structures was 0.274 Å.

Monomeric CXCL12 mediates CXCR4 degradation, phosphorylation and ubiquitination. We recently demonstrated that CXCR4 signaling exhibits agonist bias for wildtype and dimeric CXCL12. β-arrestin-2 signaling was diminished and β-arrestin-2 is necessary for many G protein independent signaling. In addition to desensitization, arrestins mediate secondary signaling and ubiquitination. To investigate the effect of CXCL12 oligomeric state on CXCR4 trafficking, we initially examined CXCR4 lysosomal targeting and degradation. HeLa cells were treated for 3 h with 80 ng/ml CXCL12, $CXCL12_1$, and $CXCL12_2$ and receptor levels were detected by immunoblot analysis, as previously described. Both CXCL12 and $CXCL12_1$ promoted approximately 60% CXCR4 degradation compared to vehicle treated cells. In contrast, degradation promoted by $CXCL12_2$ was significantly reduced (~15% vs 60%; FIG. 12A). Internalization is a prerequisite for degradation; therefore, we next examined the ability of these ligands to promote CXCR4 internalization. HeLa cells were treated with CXCL12, $CXCL12_1$, and $CXCL12_2$ for 20 min followed by FACS to measure CXCR4 surface expression. $CXCL12_1$ promoted CXCR4 internalization to the same levels as that promoted by CXCL12 (FIG. 12B). However, internalization promoted by $CXCL12_2$ was significantly consistent with inefficient degradation (FIG. 12B).

Figure 12C:
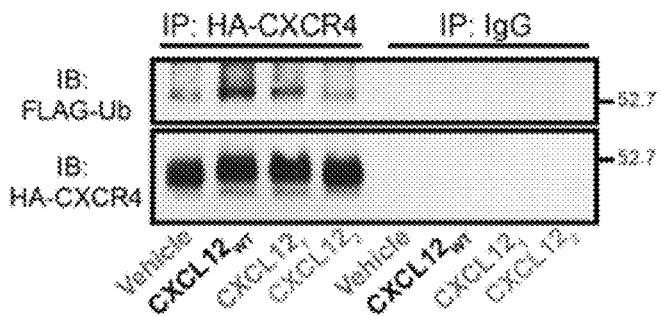
FIG. 12C. HEK293 cells stably expressing HA-CXCR4 were stimulated with vehicle or 80 ng/ml CXCL12 variants for 30 min.

Ubiquitination of CXCR4 by the E3 ubiquitin ligase AIP4 on carboxy-terminal lysine residues is essential for its targeting and degradation in lysosomes. We next examined the effect of CXCL12, $CXCL12_1$, and $CXCL12_2$ on CXCR4 ubiquitination. HEK293 cells stably expressing HA-CXCR4 and transfected with FLAG-ubiquitin were treated with vehicle and each CXCL12 variant for 30 min. HA-CXCR4 was immunoprecipitated and ubiquitinated receptor was detected by immunoblotting for the FLAG epitope to detect incorporated ubiquitin. Treatment with CXCL12 promoted ubiquitination of CXCR4, compared to vehicle treated cells, similar to what we have previously observed (FIG. 12C). $CXCL12_1$ also promoted CXCR4 ubiquitination, although not to the same degree as CXCL12 (FIG. 12C). In contrast, dimeric SDF-1α failed to promote CXCR4 ubiquitination, consistent with its inability to promote CXCR4 degradation (FIG. 12C).

Figure 12D:
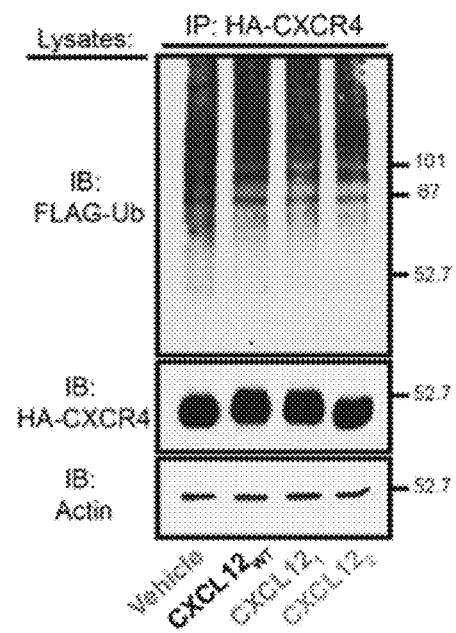
FIG. 12D. HA-CXCR4 was immunoprecipitated using an anti-HA polyclonal antibody and samples were analyzed by immunoblotting to detect incorporated FLAG-ubiquitin. Shown are representative blots from one of three independent experiments performed.

We have previously shown that AIP4-dependent ubiquitination of CXCR4 is dependent upon phosphorylation of serine residues 324 and 325 in the C-tail. To examine the effect of CXCL12 variants on serine phosphorylation, we performed confocal immunofluorescence microscopy using an anti-mouse CXCR4 antibody that selectively recognizes pS324 and pS325. HeLa cells transfected with HA-CXCR4-YFP were treated with 80 ng/ml vehicle, CXCL12, $CXCL12_1$, and $CXCL12_2$ for 15 min. Vehicle treated cells exhibited very little staining consistent with CXCR4 being unphosphorylated under basal conditions CXCR4 (FIG. 12D).

Figure 12I:
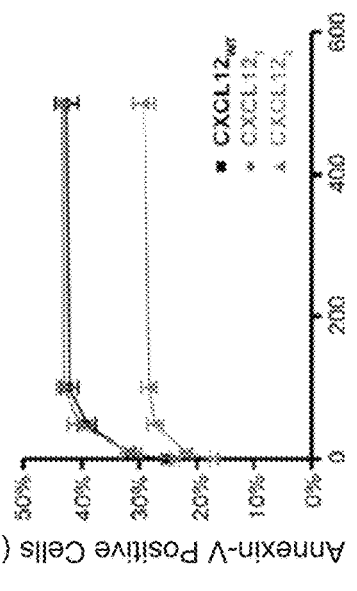
FIG. 12I. KG1a cells transiently expressing CXCR4-YFP were stimulated with increasing concentrations of each CXCL12 variant. Cells were stained with APC-conjugated annexin V and apoptosis was quantified by flow cytometry. Points denote the mean percentage of cells positive for annexin V±S.E.M, n=3. The level of annexin V staining was significantly different between both CXCL12$_{WT}$ and CXCL12$_2$, and CXCL12$_1$ and CXCL12$_2$, at all concentrations except 1 ng/ml ($p<0.05$).
Figure 12J:
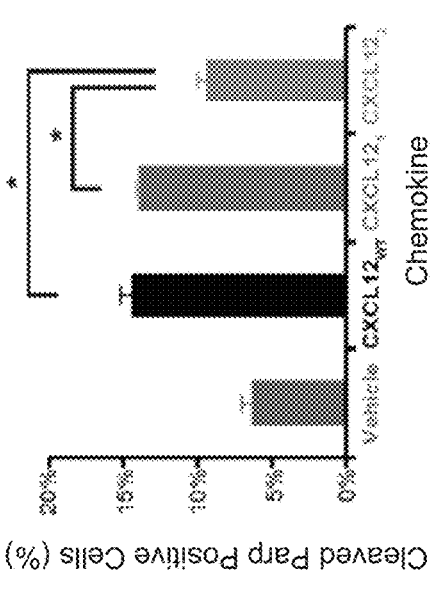
FIG. 12J. To confirm apoptosis, PARP cleavage was monitored in KG1a cells transiently transfected with CXCR4-YFP stimulated with 100 ng/ml CXCL12$_{WT}$, CXCL12$_1$, or CXCL12$_2$. Bars denote the percentage of cells positive for cleaved PARP±S.E.M., n=3. (*, $p<0.05$; **, $p<0.001$).
Figure 12E:
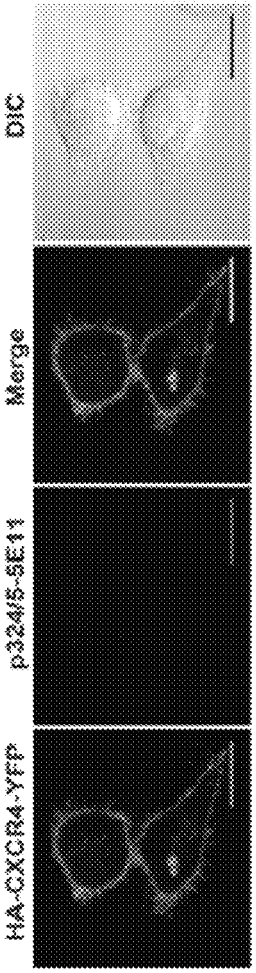
FIG. 12E. HeLa cells transiently transfected with HA-CXCR4-YFP were stimulated for 30 min with vehicle.
Figure 12F:
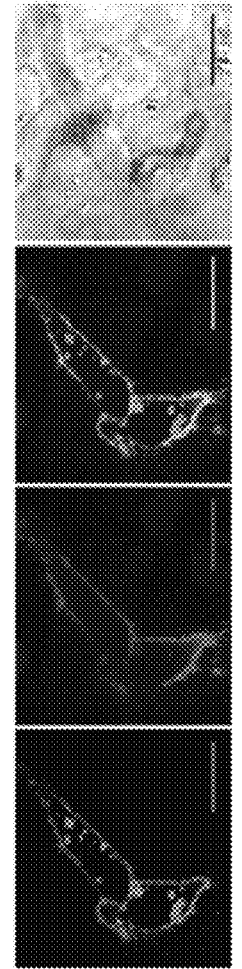
FIG. 12F. HeLa cells transiently transfected with HA-CXCR4-YFP were stimulated for 30 min with 80 ng/ml CXCL12$_{WT}$.
Figure 12G:
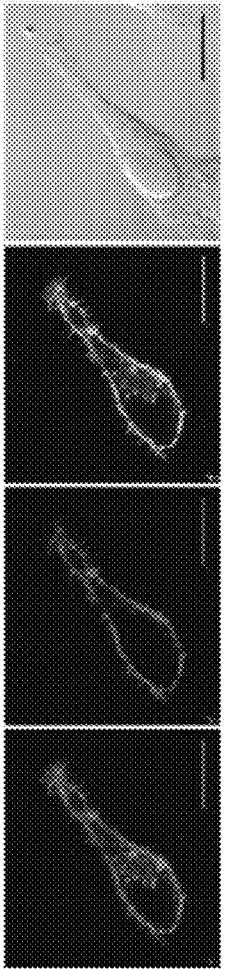
FIG. 12G. HeLa cells transiently transfected with HA-CXCR4-YFP were stimulated for 30 min with 80 ng/ml CXCL12$_1$.

In contrast, treatment with CXCL12 or $CXCL12_1$ produces strong staining suggesting that CXCR4 is robustly phosphorylated on serine residues 324 and 325 (FIG. 12E, 12F). However, $CXCL12_2$ treatment resulted in weak staining similar to vehicle indicating that $CXCL12_2$ does not promote CXCR4 phosphorylation on serine residues 324 and 325.

In summary, $CXCL12_1$ is able to promote robust internalization, phosphorylation and ubiquitination of CXCR4 and hence its degradation. In contrast, $CXCL12_2$ does not efficiently promote internalization, phosphorylation and ubiquitination of CXCR4 and thus does not promote CXCR4 degradation.

Figure 12H:
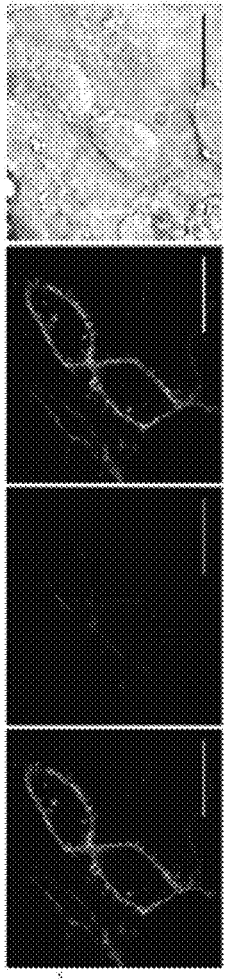
FIG. 12H. HeLa cells transiently transfected with HA-CXCR4-YFP were stimulated for 30 min with 80 ng/ml CXCL12$_2$. Cells were fixed, permeabilized and stained with an anti-CXCR4-p324/5 monoclonal antibody and analyzed by confocal immunofluorescence microscopy. Shown in green is YFP-tagged CXCR4 (far left panels) and shown in red is staining for phosphorylated CXCR4 Ser324 and Ser325 (middle left panels). Co-localization between YFP-tagged CXCR4 and phosphorylated CXCR4 appear yellow in the merge (middle right panels). Differential interference contrast (DIC) images are also shown (far right panels). Shown are representative micrographs from three independent experiments. Bars, 20 µm.
Figure 13:
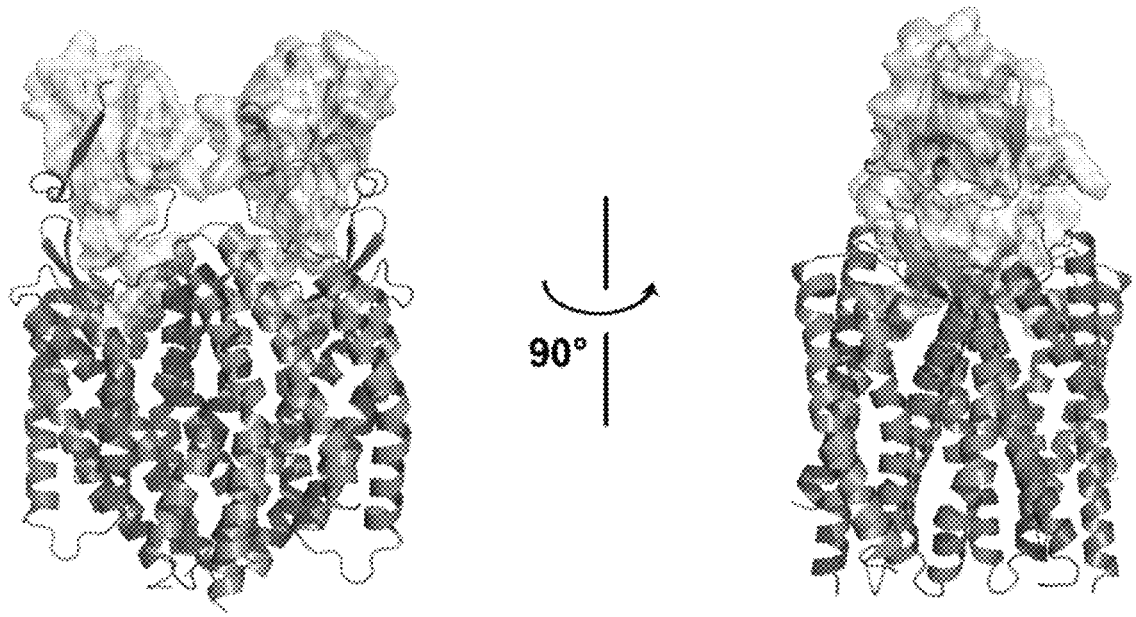
FIG. 13. Model of CXCL12$_1$ complexed to full-length CXCR4 receptor.

$CXCL12_1$ enhances apoptosis in acute myeloid leukemia cells. Lastly, we began to explore the therapeutic potential of $CXCL12_1$. We previously showed that $CXCL12_{WT}$ could mitigate colorectal and melanoma metastasis in vivo, but $CXCL12_2$ was a more potent inhibitor. Kremer et al. recently discovered an unexpected role for CXCL12 as an inducer of apoptosis in acute myeloid leukemia cell lines and clinical isolates. To determine the relevant CXCL12 variant, we exposed KG1a leukemia cells to CXCL12 variants for 16-18 h and then stained for annexin V. Both $CXCL12_{WT}$ and $CXCL12_1$ treatment produced a robust dose-dependent increase in annexin V with $EC_{50}$ values of 1.75±0.6 and 2.38 t 0.6 nM, respectively (FIG. 12H). In contrast, $CXCL12_2$ resulted in a small but significant increase in annexin V. To confirm that the annexin V staining was reporting on apoptosis we also measured the presence of cleaved PARP. As expected, all three variants enhanced the cleavage of PARP but the $CXCL12_{WT}$ and $CXCL12_1$ were significantly greater than $CXCL12_2$ (FIG. 12I). CXCL12-mediated apoptosis is unaffected by the G-type protein inhibitor pertussis toxin. This suggests apoptosis is dependent on β-arrestin-2 signaling, which is consistent with the weak recruitment mediated by $CXCL12_2$.

Radioligand displacement. Commercial membrane preparations of cells stably expressing CXCR4 or CXCR7 were purchased (Millipore). Five micrograms of protein per point was incubated for 90 min on ice in binding buffer with 0.03 nM of $^{21}$I-CXCL12 as a tracer and increasing concentrations of competitor in a final 40 μL volume. Bound radioactivity was separated from free ligand by filtration, and receptor-bound radioactivity was quantified by gamma-radiation counting (Perkin-ECXCL121er Life and Analytical Sciences). Isolated membrane binding experiments were carried out in duplicate.

THP-1 calcium response. THP-1 monocyte cells were washed twice and resuspended in 96-well format at $2\times10^5$ cells/well in assay buffer: Hanks buffered saline solution (HBSS), 20 mM HEPES (pH 7.4), 0.1% (w/v) BSA, and FLIPR Calcium4 dye (Molecular Devices) and then incubated for 1 h at 37° C., 5% $CO_2$. Fluorescence was measured at 37° C. using a FlexStation3 Microplate Reader (Molecular Devices) with excitation and emission wavelengths at 485 nm and 515 nm, respectively. Chemokines were resuspended at the indicated concentrations and added to the cells following a 20 s baseline fluorescence measurement. Percent calcium flux was calculated from the maximum fluorescence minus the minimum fluorescence as a percent of baseline. $EC_{50}$ values were determined by non-linear fitting to a four parameter logistic function.

THP-1 chemotaxis. Chemotaxis experiments were performed using Tranwell (5 mm pore size; Costar) in 24-well format. The indicated concentrations of $CXCL12_1$ were resuspended in RPMI 1640 containing 0.2% (w/v) BSA and added to the lower chamber. THP-1 cells were washed twice and 5×10' cells were added to the upper chamber. Plates were incubated for 3 h at 37° C., 5% $CO_2$. Following incubation, Transwell membranes were removed and cells that migrated into the lower chamber were counted using a TC-10 Automated Cell Counter (BioRad) and hemocytometer. The chemotactic index was calculated as the difference in migrated cell number between those exposed to chemokine and the vehicle control.

NALM6 chemotaxis. NALM6 cells were grown in RPMI-1640 supplemented with 10% FBS, 100 U/mL penicillin-streptomycin, 2 mM glutamine, 50 μM α-mercaptoethanol, non-essential amino acids, 1 mM Na-pyruvate and 25 mM HEPES buffer (pH 7.3). Chemotaxis assays were performed in triplicate in 48-well Boyden chambers (NeuroProbe), using 5 μm pore-sized polyvinylpyrrolidone-free polycarbonate membranes. Chemotaxis medium (RPMI-1640, 25 mM HEPES supplemented with 1% FBS) alone or chemotaxis medium containing increasing concentrations of CXCL12 variants was added to the lower wells. Cells (1×10' per well) resuspended in chemotaxis medium were added to the upper well and incubated for 90 min at 37° C. in 5% $CO_2$ atmosphere. Cells were removed from the upper part of the membrane with a rubber policeman. Cells attached to the lower side of the membrane were fixed and stained as described. Migrated cells were counted in five randomly selected fields of 1000-fold magnification.

MiaPaCa2 chemotaxis. Chemotactic migration of pancreatic cancer MiaPaCa2 cells was performed as previously described using Transwell plates coated with 15 ug/ml collagen. Briefly, MiaPaCa2 cells were serum starved for 2 hours, lifted using enzyme-free dissociation buffer, washed and then counted using a hemocytometer. 100,000 cells in 10 uL of serum free media were plated into the top chamber of each Transwell. The bottom chamber of each Transwell contained each stimulant in 500 uL serum free media. MiaPaCa2 cells were allowed to migrate for 6 hours, after which the cells remaining on the top of the chamber were swabbed out. Plates were then fixed in 4% paraformaldehyde and stained with DAPI. Migrated cells were visualized and counted by fluorescence microscopy, with 5 representative high-powered fields taken per well.

β-arrestin-2 recruitment. β-arrestin-2 recruitment was measured using an intermolecular BRET assay performed as described previously. HEK293E cells were cotransfected with 1 mg of CXCR4-eYFP construct with 0.05 mg of β-arrestin-2-RLuc (a gift from Michel Bouvier, University of Montreal, Montreal, QC, Canada). For [acceptor]/[donor] titrations 0.05 mg of β-arrestin-2-RLuc were cotransfected with increasing amounts of the CXCR4-eYFP construct. All transfections were completed to 2 mg/well with empty vector. Following overnight culture, transiently transfected cells were seeded in 96-well, white, clear-bottom microplates (View-Plate, Perkin-ECXCL121er Life and Analytical Sciences), coated with poly-D-lysine, and left in culture for 24 h. Cells were washed once with PBS, and the RLuc substrate coelenterazine-II (NanoLight Technology) was added at a final concentration of 5 mM to BRET buffer (PBS, 0.5 mM $MgCl_2$, 0.1% w/v glucose). β-arrestin recruitment was measured 30 min after ligand addition. The values were corrected to BRETnet by subtracting the background BRET signal obtained in cells transfected with RLuc construct alone.

Agarose microdroplet assay. The agarose microdroplet assay was performed to determine U-937 cellular migration, as previously described. $0.5\times10^6$ cells/ml U-937 target cells were harvested and washed in HBSS. Cells were spun at 2,000 rpm and were transferred to a graduated 15 ml glass conical tube. The cell concentration was adjusted in agarose medium, prepared from 2% low melting temperature Seaplaque agarose and medium containing 15% FBS, using a 1:4 volume-to-volume dilution. A 1 μl agarose droplet containing $1-10^5$ target cells was placed in the center of each well of a 96-well flat-bottom tissue culture plate, in triplicate, using a gastight 0.05 ml Hamilton syringe (Hamilton Company, Reno, Nev.). Droplets were allowed to harden at 4° C. for 20 min. 200 μl chilled test media was applied to each well. Test medium consisted of serum-free medium, 25% FBS, and the indicated CXCL12 concentrations. The plate was incubated for 18-24 h at 37° C. and 5% $CO_2$. Following incubation, the radius of each droplet was determined and target cell migration was measured at four directional points 900 from one another, using an inverted light microscope equipped with a gridded eyepiece, at 40× total magnification. Percent inhibition of each sample was quantified. The plate was incubated for an additional 24 h to measure recovery, and viability was determined by trypan blue exclusion.

NMR structure determination. All NMR spectra were acquired on a Bruker DRX 600 MHz spectrometer equipped with a $^1$H, $^{15}$N, $^{13}$C TXI cryoprobe at 298 K. Experiments were performed in a solution containing 25 mM deuterated MES (pH 6.8), 10% (v/v) D$_2$O, and 0.02% (w/v) NaN$_3$. NOE distance restraints were obtained from 3D $^{15}$N-edited NOESY-HSQC, aliphatic $^{13}$C-edited NOESY-HSQC, and aromatic $^{13}$C-edited NOESY-HSQC spectra ($\tau_{mix}$=80 ms) collected on both [U-$^{15}$N,$^{13}$C]-CXCL12$_1$ saturated with CXCR4$_{1-38}$ and [U-$^{15}$N,$^{13}$C]-CXCR$_{1-38}$ saturated with CXCL12$_1$. Intermolecular NOEs were obtained from a 3D F1-$^{13}$C/$^{15}$N-filtered/F3-$^{13}$C-edited NOESY-HSQC ($\tau_{mix}$=120 ms) collected on both [U-$^{15}$N,$^{13}$C]-CXCL12$_1$ saturated with CXCR4$_{1-38}$ and [U-$^{15}$N,$^{13}$C]-CXCR$_{1-38}$ saturated with CXCL12$_1$. In addition to NOEs, backbone φ/ψ dihedral angle restraints were derived from $^1$H$^N$, $^1$H$^\alpha$, $^{13}$C$^\alpha$, $^{13}$C$^\beta$, $^{13}$C', and $^{15}$N chemical shift data using TALOS+. Both distance and dihedral restraints were used to generate initial NOE assignments and preliminary structures via the NOE-ASSIGN module of CYANA. Complete structure determination was undertaken as an iterative process of correcting/assigning NOEs and running structure calculations with CYANA. The 20 CYANA conformers with the lowest target function were further refined by a molecular dynamics protocol in explicit solvent using XPLOR-NIH.

2D NMR characterization. All NMR spectra were acquired on a Bruker DRX 600 MHz spectrometer equipped with $^1$H, $^{15}$N, $^{13}$C TXI cryoprobe at 298 K. Experiments were performed in a solution containing 25 mM deuterated MES (pH 6.8), 10% (v/v) D$_2$O, and 0.02% (w/v) NaN$_3$. Heteronuclear NOE experiments were collected on 250 μM [U-$^{15}$N]-CXCR4$_{1-38}$ in the absence and presence of 500 μM CXCL12$_1$. $^{15}$N-HSQC spectra were collected to monitor the interaction of 200 μM [U/$^{15}$N]-CXCR4$_{1-38}$ was titrated with 0, 100, 200, 300, 400, and 500 μM CXCL12$_2$. $^{15}$N-HSQC spectra were collected to monitor the interaction of 250 μM [U-$^{15}$N]-CXCR4$_{1-38}$ was titrated with 0, 62.5, 125, 187.5, 250, 375 and 500 μM CXCL12$_1$.

Calcium response of CXCR4 mutants. Cell culture, transfection and calcium flux assay of Chinese hamster ovary K1 (CHO-K1) cells was performed as previously described.

Cell lines, antibodies and other reagents. HEK (Human embryonic kidney) 293 (Microbix, Toronto, Canada) and HeLa (American Type Culture Collection) cells were maintained in Dulbecco's modified Eagles medium (DMEM; Hyclone) supplemented with 10% fetal bovine serum (FBS; HyClone Laboratories, Logan, Utah). The PE-conjugated CXCR4 (CD184) isotype control antibodies, and rat anti-CXCR4 (2B11) and were from BD Biosciences (San Jose, Calif.). The anti-actin antibody was from MP Biomedicals (Aurora, Ohio). The Alexa-Fluor 568-conjugated goat anti-rabbit antibody was from Molecular Probes (Eugene, Oreg.). The anti-FLAG M2 horseradish peroxidase conjugated monoclonal antibody was from Sigma (St. Louis, Mo.). The anti-HA polyclonal and monoclonal antibodies were from Covance (Berkeley, Calif.). CXCL12 was from PeproTech (Rockyhill, N.J.).

CXCR4 degradation assay. HeLa cells grown on 6-cm dishes were washed once and incubated with DMEM containing 10% FBS and 50 μg/ml cyclohexamide for 15 min at 37° C. Cells were then incubated in the same medium containing vehicle (PBS containing 0.5% bovine serum albumin [BSA]), 80 ng/ml CXCL12$_{WT}$, CXCL12$_1$, or CXCL12$_2$ for 3 h. Cells were washed once and collected in 300 μl 2× sample buffer. Receptor levels were determined by SDS-PAGE followed by immunoblotting using an anti-CXCR4 antibody. Blots were stripped and reprobed for actin to assess loading. Receptor levels normalized to actin levels were determined by densitometric analysis.

CXCR4 internalization assay. HeLa cells grown on 6-cm dishes were washed twice with PBS and detached from the surface of the plate by incubating with 350 μl Cellstripper cell dissociation solution (Mediatech, Va.) for 10 min at 37° C. Cells were collected in 4 ml PBS containing 0.1% BSA (Media Tech, Va.) by centrifugation. Cell pellets were re-suspended in 1.5 ml PBS-0.1% BSA and 5×10$^5$ cells were transferred to a fresh 5 ml polystyrene round bottom tube (BD falcon) and washed once with PBS+0.1% BSA and re-suspended in 250 μl PBS-0.1% BSA. Cells were incubated at 37° C. for 15 min and then treated with vehicle, 80 ng/ml CXCL12$_{WT}$, CXCL12$_1$, or CXCL12$_2$ for 20 min at 37° C. Following treatment, 4 mL cold PBS was added to each tube, cells were collected by centrifugation and then fixed by re-suspending the pellet in 500 μl 4% paraformaldehyde (made in PBS) and incubating for 15 min at 37° C. Cells were collected by centrifugation and washed once with 4 mL PBS and then twice with PBS-0.1% BSA. Cells were stained with PE-conjugated anti-CXCR4 or isotype control antibodies by re-suspending the pellet in 100 μl PBS-0.1% BSA (supplemented with 5% normal goat serum) containing anti-CXCR4 antibody (1:100 dilution) and incubating for 1 hour at room temperature in the dark. Following staining, cells were washed twice with 4 mL PBS-0.1% BSA. Finally, cells were re-suspended in 300 μl PBS-0.1% BSA and kept in the dark until the analysis was performed. CXCR4 surface expression was analyzed by flow cytometry (FACS-CANTO; Becton Dickinson) and analysis was performed using FlowJo v.9.3 software.

CXCR4 ubiquitination assays. HEK293 cells stably expressing HA-CXCR4 grown on 10-cm dishes were transfected with 3 μg FLAG-ubiquitin. The next day, cells were passaged onto 6-cm dishes and allowed to grow for an additional 24 h. The following day, cells were incubated in DMEM containing 20 mM HEPES for 6 h and then treated with vehicle (PBS, 0.1% BSA), 80 ng/ml CXCL12$_{WT}$, CXCL12$_1$, or CXCL12$_2$ for 30 min. Cells were then washed once on ice with cold PBS, and collected in 1 ml lysis buffer [50 mM Tris-Cl, pH 7.4, 150 mM NaCl, 5 mM EDTA, 0.5% (w/v) sodium deoxycholate, 1% (v/v) NP-40, 0.1% (w/v) SDS, 20 mM N-ethyCXCL121aleimide (NEM), and 10 μg/ml each of leupeptin, aprotinin, and pepstatin A]. Samples were transferred into microcentrifuge tubes and placed at 4° C. for 30 min, followed by sonification and centrifugation to pellet cellular debris. Clarified cell lysates were incubated with an anti-HA polyclonal and isotype control antibodies and the immunoprecipitates were analyzed by SDS-PAGE followed by immunoblotting using an anti-FLAG antibody conjugated to HRP.

Connfocal microscopy. HeLa cells transiently transfected with HA-CXCR4-YFP were passaged onto poly-L-lysine coated coverslips and grown for 24 h. The next day, cells were washed once with warm DMEM containing 20 mM HEPES, pH 7.5, and incubated in the same medium for 3-4 h at 37° C. Cells were treated with 80 ng/ml CXCL12$_{WT}$, CXCL12$_1$, or CXCL12$_2$ and vehicle for 30 min. Cells were then fixed with PBS containing 3.7% paraformaldehyde, followed by permeabilization with 0.05% (w/v) saponin for 10 min, similar to a protocol we have described previously. Cells were then incubated with 1% goat serum in 0.05% saponin-PBS for 30 min at 37° C., followed by staining with anti-mouse monoclonal antibody that recognizes dually phosphorylated CXCR4 on serine residues 324 and 325 (clone 5E11) (1:50 dilution) for 1 h at 37° C. Cells were washed five times with 0.05% saponin-PBS, followed by incubating with Alexa-Fluor 568-conjugated anti-rabbit antibody for 30 min at 37° C. (1:200 dilution). Finally, cells were washed five times with 0.05% saponin-PBS and mounted onto glass slides using mounting media containing 4,6-diamidino-2-phenylindole (Vectashield mounting media with DAPI). Samples were analyzed using an LSM 510 laser scanning confocal microscope (Carl Zeiss, Thornwood, N.Y.) equipped with a Plan-Apo 63×/1.4 oil lens objective. Images were acquired using a 1.4-megapixel cooled extended spectra range RGB digital camera set at 512×512 resolution. Acquired images were analyzed using ImageJ, version 1.41o software (National Institutes of Health, Bethesda, Md.) and Adobe Photoshop (CS4).

Apoptosis assays. KG1a (human acute myelogenous leukemia) cells were assayed for CXCL12-dependent apoptosis as previously described. Briefly, CXCR4 expression on KG1a cells was achieved via transient transfection with a plasmid encoding a CXCR4-YFP fluorescent fusion protein. These cells were treated with the indicated concentration of each CXCL12 variant and cultured for 16-18 h prior to measuring apoptosis. Apoptosis was assayed by staining cells with APC-conjugated annexin V to detect cell-surface phosphatidyl serine (BD Biosciences) or Alexaflour-647-conjugated antibody to detect cleaved PARP (BD Biosciences), and the percentage of YFP+ cells undergoing apoptosis was determined by flow cytometry.

Statistical Analysis and final figures. Data were analyzed by one-way analysis of variance (ANOVA) using GraphPad Prism 4.0 (GraphPad Software).

Example 3. Structural Basis for Balanced CXCR4 Signaling by a Constitutively-Monomeric CXCL12 Variant In this example, the inventors show that an engineered CXCL12 locked-monomer functions as a balanced agonist with enhanced G-protein and arrestin signaling. The balanced agonist alone directs the fate of CXCR4 by promoting phosphorylation, ubiquitination, internalization and degradation. These modifications originate at the plasma membrane suggesting that balanced and biased agonists stabilize unique receptor conformations. We then solved the NMR complex structure of monomeric CXCL12 and the CXCR4 N-terminus and observed a monomer-specific interaction that is required for receptor activation. A model of the full-length 1:1 receptor complex from component NMR and crystallographic structures, coupled with experimental validation, reveals a contiguous interface for rational ligand design.

Here we used a constitutively-monomeric CXCL12 variant ($CXCL12_1$) to explore balanced CXCR4 signaling. After confirming that the $CXCL12_1$ activates both G protein and arrestin pathways, the fate of activated cell-surface CXCR4 was tracked following activation with both the balanced or G protein biased agonist. Only the CXCL12 monomer promotes CXCR4 phosphorylation, ubiquitination, and degradation. We then determined the structure of $CXCL12_1$ bound to the N-terminal domain of CXCR4 ($CXCR4_{1-38}$). Apolar residues near the CXCR4 N-terminus dock into a cleft that is inaccessible in the dimer, and this monomer-specific interaction is essential for full receptor activation. Combination of our $CXCL12:CXCR4_{1-38}$ complex NMR structure and the CXCR4-inhibitor crystal structure permitted modeling of an intact 1:1 complex. Our model extends the conceptually useful "two-site" model and suggests that receptor activation involves the formation of an extensive protein-protein interface encompassing nearly half of the CXCL12 surface.

Figure 18A:
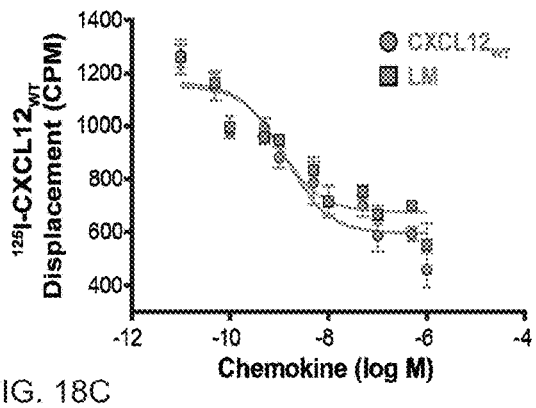
FIG. 18A. CXCL12$_1$ enhances CXCR4-mediated calcium flux, migration, and arrestin recruitment. Binding of CXCL12 proteins was measured by radioligand displacement of $^{12}$I-CXCL12 from CXCR4-containing membrane fragments. K$_d$ values for CXCR4 binding of CXCL12$_{WT}$ and CXCL12$_1$ were calculated as 1.44±1.5 nM and 0.97±1.5 nM, respectively, from their corresponding logEC$_{50}$ values of −8.84±0.17 and −9.01±0.17.
Figure 18C:
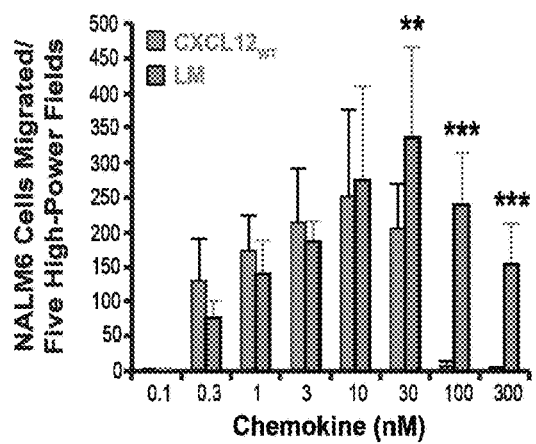
FIG. 18C. NALM6 cell migration was quantified after 90 min stimulation. Chemotaxis was determined from counting the number of migrated cells in five high power magnification fields.
Figure 18E:
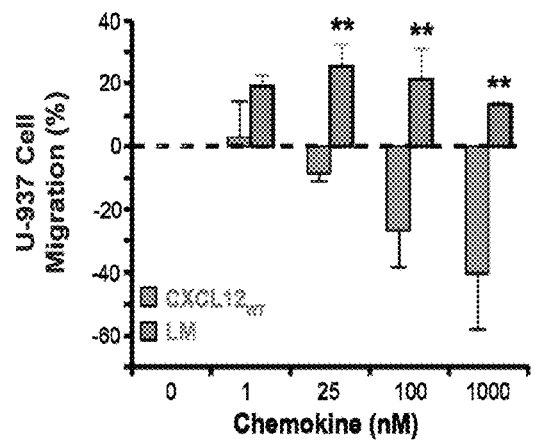
FIG. 18E. U-937 cells were confined to a 1 µl agarose droplet and migration was observed following 18-24 h incubation with test media containing CXCL12$_{WT}$ or CXCL12$_1$. Migration inhibition presented as mean±SD with chemokine-free control normalized to zero.
Figure 18B:
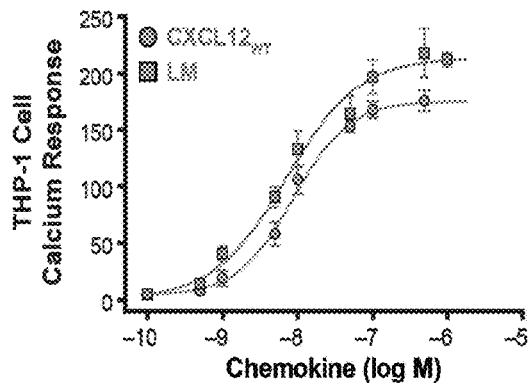
FIG. 18B. Dose-dependent treatment of THP1 cells with either CXCL12$_1$ or CXCL12$_{WT}$ induced CXCR4-mediated intracellular calcium response with EC$_{50}$ values of 7.1±1.3 and 8.7±1.7 nM, respectively.
Figure 18D:
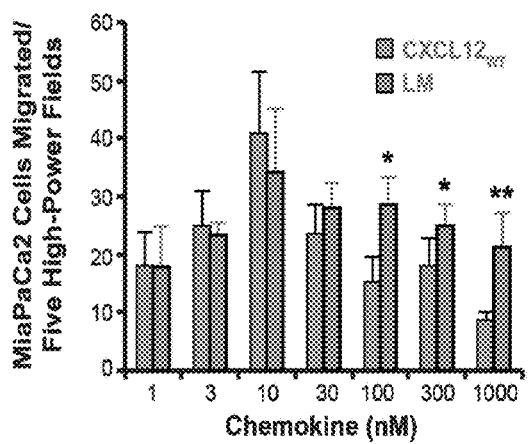
FIG. 18D. Migration of MiaPaCa2 was monitored after 6 h stimulation using Transwell migration chambers. Chemotaxis was determined from counting the number of migrated cells in five high power magnification fields.
Figure 18F:
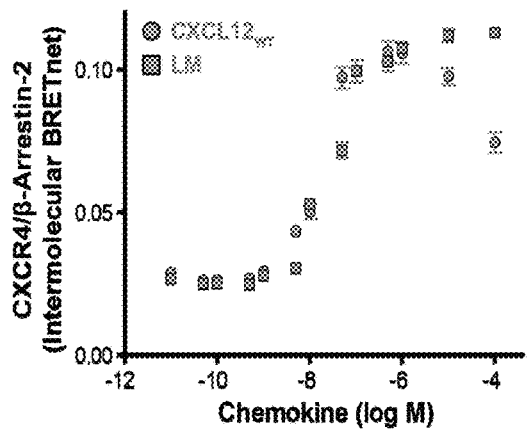
FIG. 18F. HEK293 cells transiently co-expressing β-arrestin-2-RLuc as a BRET donor and CXCR4-YFP as BRET acceptor were stimulated with increasing chemokine concentrations resulting in EC$_{50}$ values of 17.6±1.1 nM for CXCL12$_{WT}$ and 30.6±1.1 nM for CXCL12$_1$. CXCL12$_{WT}$ and CXCL12$_1$ responses were compared at each dose by two-tailed T-test (*, p<0.01; , p<0.01; *, p<0.001).

$CXCL12_1$ is a balanced CXCR4 agonist with enhanced G protein and arrestin signaling. At low concentrations CXCL12 is hypothesized to interact with CXCR4 as a monomer to promote cellular migration; as local chemokine concentrations increase the dimeric form predominates and induces non-migratory cellular idling signaling. Similarly, peptides derived from the CXCR4 N-terminus bind CXCL12 in a 1:1 stoichiometry but also promote formation of a 2:2 complex at higher concentrations. Binding of CXCR4 peptides with specific tyrosine sulfation patterns can even allosterically modulate chemokine dimerization. To simplify this complex equilibrium we engineered a disulfide-constrained CXCL12 variant ($CXCL12_1$) that remains strictly monomeric at millimolar concentrations. To test if $CXCL12_1$ is functionally equivalent to the monomeric form of $CXCL12_{WT}$, we compared their relative ability to recognize and activate CXCR4. Radioligand displacement on CXCR4 cell-membrane preparations demonstrated similar affinities for $CXCL12_{WT}$ and $CXCL12_1$ with $K_d$ values of 1.4±1.5 nM and 0.97±1.5 nM, respectively (FIG. 18A). We next established the activity of $CXCL12_1$ as a CXCR4 agonist by measuring its ability to mobilize intracellular calcium, a sensitive indicator of G protein activation. $CXCL12_1$ produced a robust, dose-dependent calcium flux response equivalent to $CXCL12_{WT}$ (FIG. 18B). Chemokines induce cellular migration over a narrow concentration range when measured using a Boyden chamber or similar apparatus. The monomer-dimer equilibrium might contribute to CXCL12's narrow bell-shaped chemotactic profile, with the loss of migration at higher concentrations attributed to the formation of inhibitory dimeric complexes. Whereas a disulfide-locked, constitutively dimeric CXCL12 variant ($CXCL12_2$) does not promote chemotaxis at any concentration, a preferentially monomeric CXCL12 variant produces a bell-shaped response over an extended concentration range. Because $CXCL12_1$ is strictly monomeric, we hypothesized it may generate a sigmoidal, rather than a biphasic, migratory response. The chemotaxis of $NACXCL12_{16}$ pre-B cells and MiaPaCa2 pancreatic cancer cells was tested using Boyden and Transwell migration chambers, respectively (FIGS. 18C, 18D). In both cases $CXCL12_1$ extended the effective dose at least 10-fold relative to $CXCL12_{WT}$ but, nonetheless, signaled migratory arrest at the highest concentrations. To assess how CXCR4 activation was interpreted in the presence of other migratory signals, U-937 leukemia cells confined to an agarose droplet were incubated in serum-containing media with increasing CXCL12 concentrations. Whereas $CXCL12_{WT}$ inhibited U-937 cell migration at nearly all concentrations with maximal inhibition of 40.1±18%, $CXCL12_1$ significantly enhanced migration, generating a bell-shaped profile, at all tested concentrations (FIG. 18E).

Figure 19I:
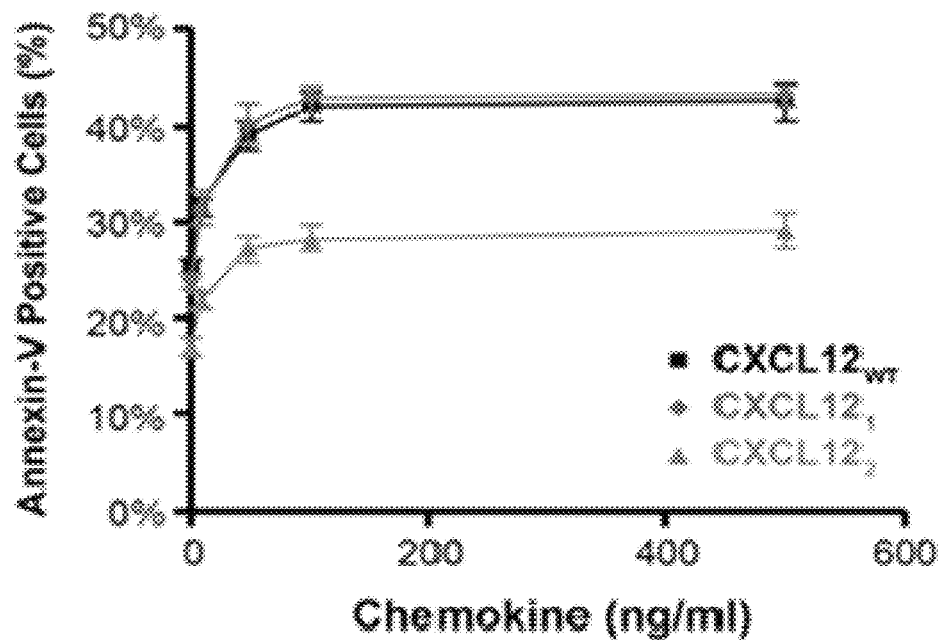
FIG. 19I. KG1a cells transiently expressing CXCR4-YFP were stimulated with increasing concentrations of each CXCL12 variant. Cells were stained with APC-conjugated annexin V and apoptosis was quantified by flow cytometry. Points denote the mean percentage of cells positive for annexin V±S.E.M, n=3. The level of annexin V staining was significantly different between both CXCL12$_{WT}$ and CXCL12$_2$, and CXCL12$_1$, and CXCL12$_2$, at all concentrations except 1 ng/ml (p<0.05).
Figure 19J:
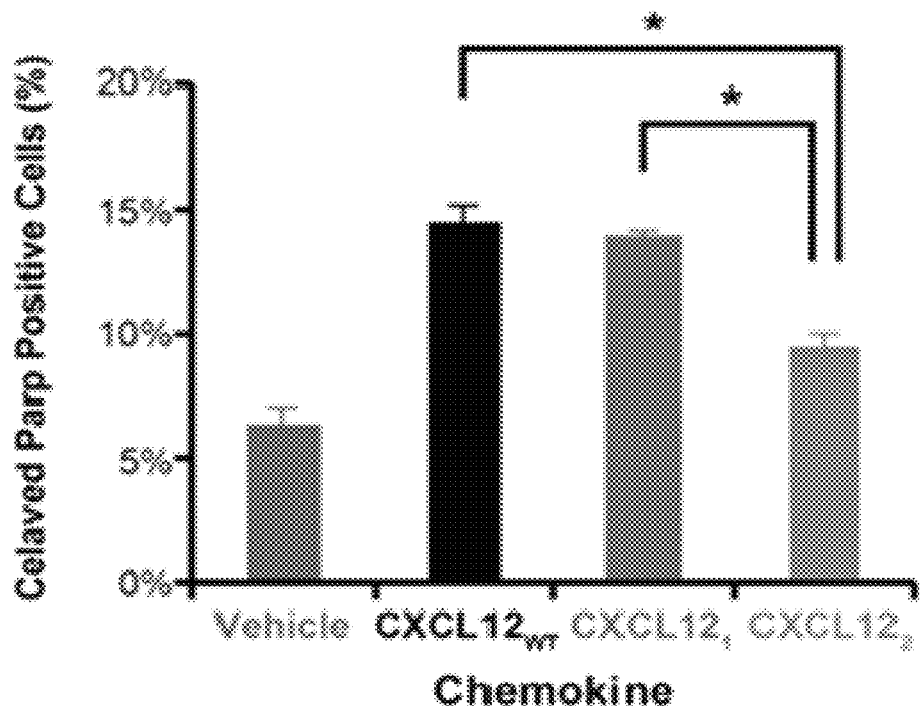
FIG. 19J. To confirm apoptosis, PARP cleavage was monitored in KG1a cells transiently transfected with CXCR4-YFP stimulated with 100 ng/ml CXCL12$_{WT}$, CXCL12$_1$, or CXCL12$_2$. Bars denote the percentage of cells positive for cleaved PARP±S.E.M., n=3. (*, p<0.05; **, p<0.001).

Chemotaxis is dependent upon recruitment of β-arrestin to CXCR4, which then induces lamellipodia formation and filamentous-actin polymerization. We recently demonstrated that monomeric CXCL12 is primarily responsible for β-arrestin-2 mobilization and subsequent internalization. We next performed dose-dependent BRET analysis to test if the $CXCL12_1$'s enhanced chemotactic profile was reflected in β-arrestin signaling. At low concentrations, $CXCL12_{WT}$ and $CXCL12_1$ both recruited β-arrestin to CXCR4 with similar potency and efficacy (FIG. 18G). However, as concentrations were increased to 10 and 100 μM, $CXCL12_{WT}$ induced a bimodal stimulation of β-arrestin reminiscent of its chemotactic dose response. In contrast, $CXCL12_1$ exhibits a sigmoidal response over the tested concentration range. Enhanced arrestin recruitment suggests that $CXCL12_1$ binding directly modifies the receptor's intracellular conformation which may effect other aspects of the receptor's fate. CXCL12 enhances apoptosis in acute myeloid leukemia cells. Lastly, we began to explore the therapeutic potential of $CXCL12_1$. We previously showed that $CXCL12_{WT}$ could mitigate colorectal and melanoma metastasis in vivo, but $CXCL12_2$ was a more potent inhibitor. Kremer et al. recently discovered an unexpected role for CXCL12 as an inducer of apoptosis in acute myeloid leukemia (AML) cell lines and clinical isolates. To identify the relevant CXCL12 variant, we exposed KG1a leukemia cells to CXCL12 variants for 16-18 h and then stained for annexin V. Both $CXCL12_{WT}$ and $CXCL12_1$ treatment produced a robust dose-dependent increase in annexin V with EC50 values of 1.75±0.6 and 2.38±0.6 nM, respectively (FIG. 19G). In contrast, $CXCL12_2$ resulted in a small but significant increase in annexin V. To confirm that the annexin V staining was reporting on apoptosis we also measured the presence of cleaved PARP. As expected, all three variants enhanced the cleavage of PARP but the $CXCL12_{WT}$ and $CXCL12_1$ were significantly greater than $CXCL12_2$ (FIG. 19H). CXCL12-mediated apoptosis is unaffected by the Gi-type protein inhibitor pertussis toxin, suggesting that AML apoptosis is primarily dependent on β-arrestin signaling and therefore unresponsive to $CXCL12_2$. Counterintuitively, AML cells possess high survival rates in the CXCL12-rich bone marrow microenvironment. Our data suggests the survival may result from concentration-dependent CXCL12 dimerization.

Monomeric (CXCL12 mediates CXCR4 degradation, phosphorylation and ubiquitination. In addition to their classic role of promoting internalization and desensitization, arrestins sometimes function as scaffolds for secondary signaling such as ubiquitination. To investigate the effect of ligand oligomeric state on receptor trafficking, we initially examined CXCR4 lysosomal targeting and degradation. HeLa cells were treated for 3 h with 80 ng/ml $CXCL12_{WT}$, $CXCL12_1$, or $CXCL12_2$, and receptor levels were detected by immunoblot analysis. Both $CXCL12_{WT}$ and $CXCL12_1$ promoted approximately 60% CXCR4 degradation in contrast to ~15% degradation by $CXCL12_2$, (FIG. 19A). Internalization is a prerequisite for degradation; therefore, we next examined the ability of these ligands to promote CXCR4 internalization. HeLa cells were treated with $CXCL12_{WT}$, $CXCL12_1$, and $CXCL12_2$ for 20 min followed by FACS measurement of CXCR4 surface expression. As shown in FIG. 19B, $CXCL12_1$ and $CXCL12_{WT}$ promoted similar levels of CXCR4 internalization. However, the nominal internalization promoted by $CXCL12_2$ was consistent with inefficient degradation (FIGS. 19A, 19B) and our previous observations.

Lysosomal targeting and degradation of CXCR4 is dependent upon C-terminal modification by the E3 ubiquitin ligase AIP4. We next examined the effect of $CXCL12_{WT}$, $CXCL12_1$, and $CXCL12_2$, on CXCR4 ubiquitination. HEK293 cells stably expressing HA-CXCR4 and transfected with FLAG-ubiquitin were treated with each CXCL12 variant for 30 min. HA-CXCR4 was immunoprecipitated and the ubiquitinated receptor was detected by immunoblotting for the FLAG epitope. Treatment with $CXCL12_{WT}$ prompted ubiquitin. $CXCL12_1$ also promoted CXCR4 ubiquitination, although not to the same degree as $CXCL12_{WT}$ (FIGS. 19C, 19D). Consistent with its inability to stimulate receptor internalization and degradation, $CXCL12_2$, failed to promote CXCR4 ubiquitination (FIG. 19C, 19D).

We have previously shown that AIP4-dependent ubiquitination of CXCR4 is dependent upon phosphorylation of Ser324 and Ser325. Ser324/Ser325 are phosphorylated at the plasma membrane by protein kinase CS and GRK6. To examine the effect of CXCL12 variants on serine phosphorylation, we performed confocal immunofluorescence microscopy using an anti-mouse CXCR4 antibody that selectively recognizes pSer324/325. HeLa cells transfected with HA-CXCR4-YFP were treated with 80 ng/ml vehicle, $CXCL12_{WT}$, $CXCL12_1$, or $CXCL12_2$ for 15 min. Vehicle treated cells exhibited very little staining consistent with CXCR4 being unphosphorylated under basal conditions (FIG. 19E). Addition of $CXCL12_{WT}$ or $CXCL12_1$ produced strong staining indicating robust CXCR4 C-terminal phosphorylation (FIGS. 19F, 19G). In striking contrast, $CXCL12_2$ treatment resulted in weak staining similar to vehicle (FIG. 19H). Taken together, our results indicate that CXCR4 ligand binding directly modifies the receptor's intracellular conformation, yielding the respective balanced or biased response.

Figure 22A:
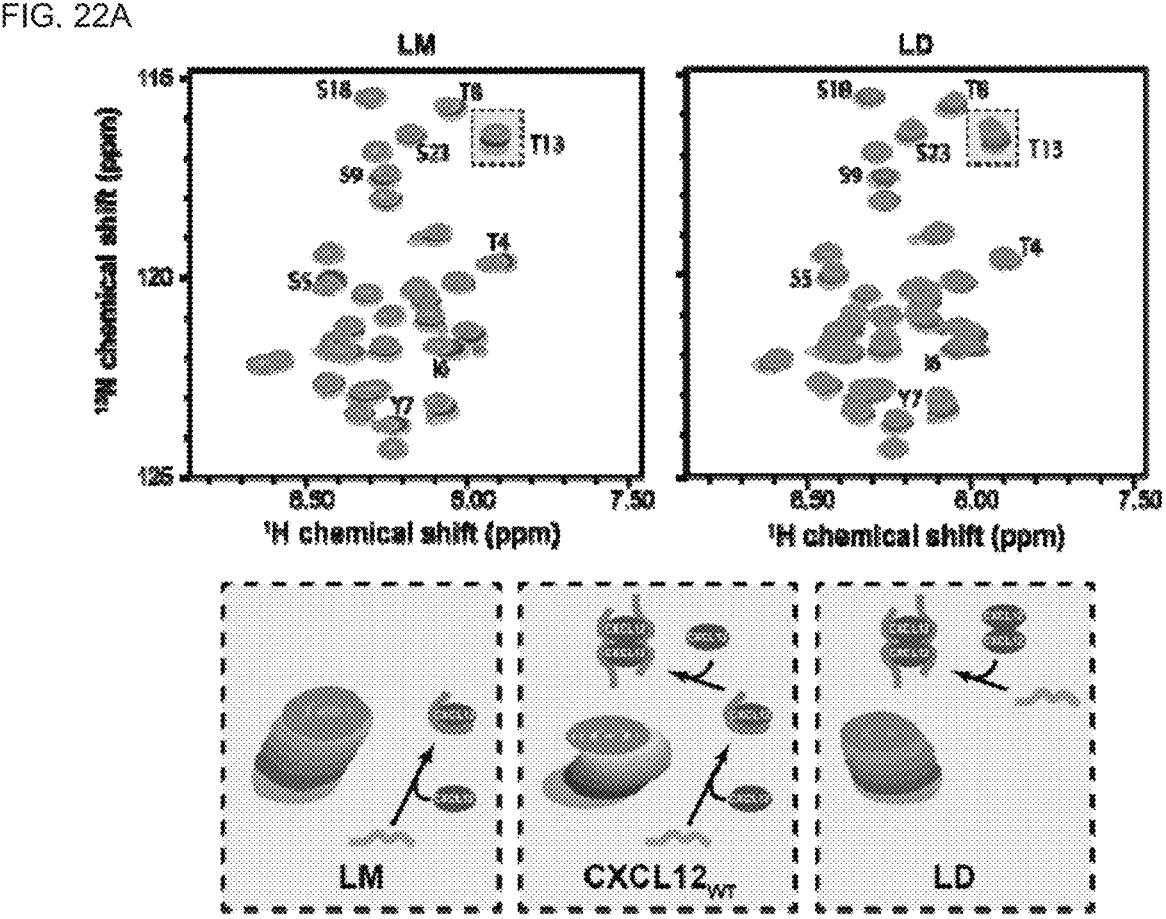
FIG. 22A. CXCL12$_1$ and CXCL12$_2$ interact disparately with the CXCR4 N-terminus. 2D H/$^{15}$N HSQC spectra of [U-$^{15}$N]-CXCR4$_{1-38}$ in 25 mM d-MES (pH 6.8) titrated with increasing concentrations (orange to green) of CXCL12$_1$ (left panel) or CXCL12$_2$ (right panel). CXCL12$_1$ and CXCL12$_2$ perturb CXCR4$_{1-38}$ distinctly. In some instances, as illustrated with T13, the direction of their perturbations can be concatenated to produce CXCL12$_{WT}$ perturbation trajectories.
Figure 22B:
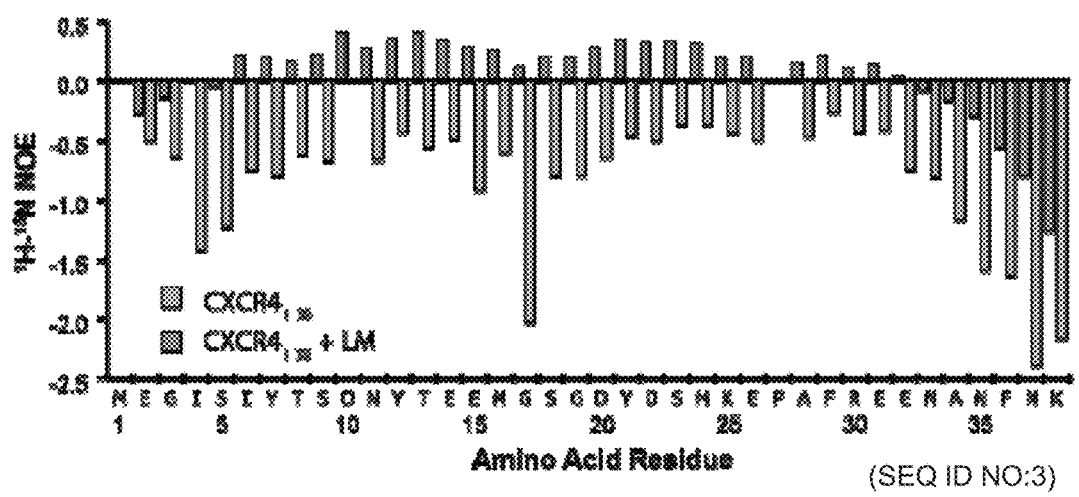
FIG. 22B. $^1$H/$^{15}$N heteronuclear NOE experiment of 250 μM [U-$^{15}$N]-CXCR4$_{1-38}$ in the absence (orange) and presence (green) of 500 μM LM. CXCR4$_{1-38}$ residues 4-7 exhibit a more stable interaction with CXCL12$_1$ than with CXCL12$_2$.

The structure of $CXCL12_1$ in complex with $CXCR4_{1-38}$. We next used nuclear magnetic resonance (NMR) spectroscopy to explore the structural mechanisms that translate $CXCL12_1$ binding into balanced agonism. Chemokine signaling is initiated by formation of an extensive protein-protein interface segregated into two distinct regions. First, the receptor N-terminus wraps around the folded chemokine domain and contributes most of the binding energy (site 1). Subsequent docking of the flexible chemokine N-terminus into a pocket within the transmembrane domain activates receptor signaling (site 2). Using a 38 amino acid CXCR4 N-terminal peptide ($CXCR4_{1-38}$), we previously showed that increasing $CXCL12_{WT}$ concentrations caused [U-$^{15}$N]-$CXCR4_{1-38}$ a resonances to shift in curved trajectories suggesting the simultaneous presence of both a 1:1 and 2:2 complexes. Here we used HSQC titrations to probe the 1:1 and 2:2 interfaces. Titrating $CXCL12_1$ or $CXCL12_2$ into [U-$^{15}$N]-$CXCR4_{1-38}$ produced chemical shift perturbations consistent with unique chemical environments for CXCR4 residues 1-13 (FIG. 22A). In contrast to previously published spectra of $CXCL12_{WT}$, all peaks in the N-terminus were visible throughout the titrations and traversed linear paths. Concatenation of the linear trajectories recreates the complicated chemical shifts induced by $CXCL12_{WT}$ and underscores the physiologic validity of both the $CXCL12_1$ and $CXCL12_2$ variants (FIG. 22A). To assess the rigidity of $CXCR4_{1-38}$ upon chemokine binding we measured $^1$H-$^{15}$N heteronuclear NOE values, which reflect the backbone flexibility for each residue on picosecond to nanosecond timescales. When bound to $CXCL12_2$, $CXCR4_{1-38}$ residues 5-10 remain relatively dynamic and imply a weak, transient interaction. $CXCL12_1$ stabilizes the high frequency motions of $CXCR4_{1-38}$ residues 5-10 (FIG. 22B).

Figure 23A:
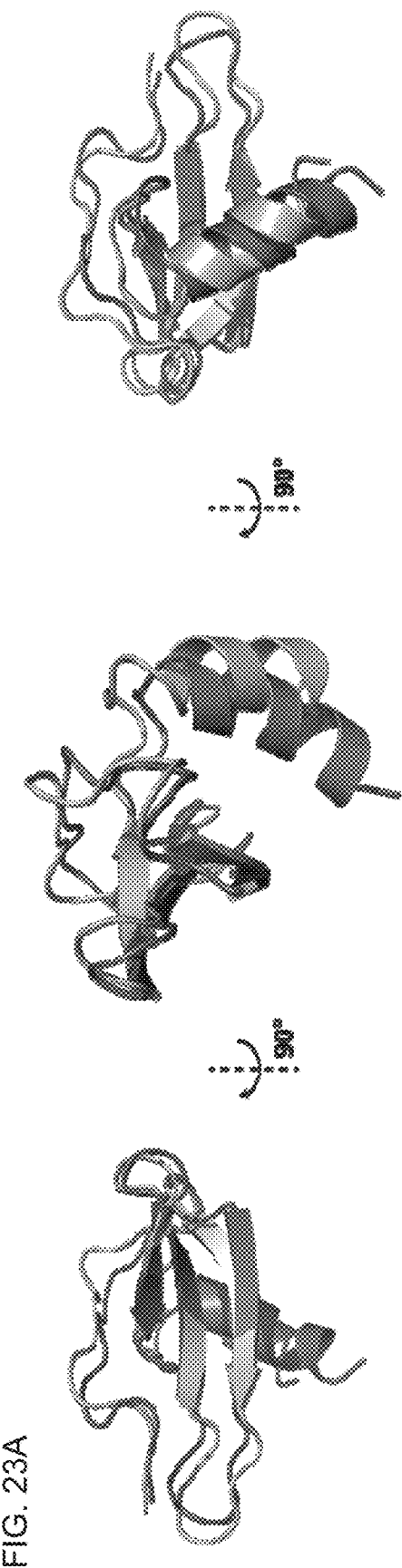
FIG. 23A. CXCL12$_1$ is incapable of CXC-type dimerization. CXCL12$_1$ (blue) residues 9-49 aligned to respective residues of CXCL12WT (gray; PDB ID 1SDF) with a backbone RMSD=1.6 Å.
Figure 23B:
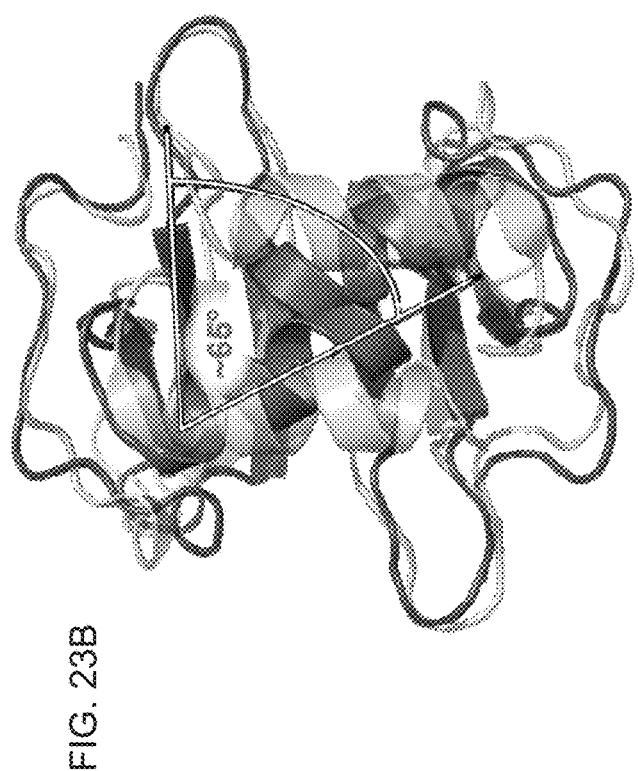
FIG. 23B. Two CXCL12$_1$ molecules (blue) are aligned with each protomer of the CXCL12$_2$ NMR structure (pink; PDB ID 2K05). The alignments possess backbone RMSDs of 1.41 Å and 1.37 Å. The CXCL12$_1$ helices are oriented an average angle of 65° relative to the β-sheet making them sterically inconsistent with dimerization.

To understand how the CXCR4 N-terminus recognizes $CXCL12_1$, we determined the complex structure by NMR. A suite of triple-resonance experiments were acquired on samples of [U-$^{13}$C,$^{15}$N]-$CXCL12_1$ saturated with $CXCR4_{1-38}$ and [U-$^{3}$C,$^{15}$N]-$CXCR4_{1-38}$ saturated with $CXCL12_1$ to assign the carbon, nitrogen, and hydrogen resonances. Next, a series of 3D nuclear Overhauser effect (NOE) spectroscopy (NOESY) experiments were collected to identify the position of neighboring hydrogen atoms within a 5 Å distance. As expected, $CXCL12_1$ adopts the canonical chemokine fold comprising a flexible N-terminus, followed by the N-loop, a three-stranded antiparallel β-sheet, and a C-terminal α-helix (FIGS. 20A-C). CXCL12$_1$ was designed to mimic the conformation of PDB 1SDF, a CXCL12 solution NMR structure determined in sodium acetate buffer at pH 4.9. In this structure the α-helix maintains a 55o relative to the 1-sheet, which would be sterically incompatible with dimerization. The CXCL12$_1$ α-helix is ~65° relative to the β-sheet and aligns to PDB 1SDF with a backbone RMSD of 1.6 Å (FIG. 23).

Determination of the CXCR4$_{1-38}$ contact surface required F1-$^{13}$C-filtered/F3-$^{13}$C-edited NOESY-HSQC experiments to unambiguously identify intermolecular constraints. Intermolecular NOEs, indicative of a stable interaction on the millisecond timescale, were observed from residues 4-27 along the peptide (FIGS. 20A-C). Overall, CXCR4$_{1-38}$ adopts a random coil architecture with a short 1-strand from Tyr7-Ser9. The position of CXCR$_{1-38}$ overlaps well with the previously published chemical shift perturbations (FIGS. 20A-C). The ProCys motif (CXCR4 Pro27 and Cys28) is nearly conserved across all chemokine receptors and delineates the flexible N-terminus from the transmembrane portion. Here we observed intermolecular NOEs from both the CXCL12$_1$ N-loop and helix to CXCR4 Lys25, Glu26, and Ala28. This constrains CXCR4 Pro27 between the helix and N-loop, marking the point where our NMR data intersects with the recent CXCR4 crystal structure. The Pro27 C$^\alpha$ is translated an average 8.6 Å toward the N-loop compared to the 2:2 complex. Subsequently, the pocket formed by the N-loop and β3 strand, known as the chemokine cleft, is slightly distorted. CXCL12$_1$ residues Glu15-His17 shift toward the β3 strand to accommodate the peptide. CXCL12$_1$ Asn46 puckers away from the pocket allowing Arg47, and to a lesser extent Ans45, to interact with the CXCR4 Tyr21 hydroxyl. The C$^\zeta$ and C$^\alpha$ atoms of Tyr21 are translated an average of 7.0 Å and 5.3 Å, respectively, compared to the 2:2 complex (FIG. 20D). In this position the Tyr21 hydrophobic contacts appear to be primarily satisfied by Val49 and the methylene of Glu15. Upon sulfation, it's reasonable to predict that Lys47, Asn45 or His17 maintain sTyr21 electrostatic interactions with negligible pocket rearrangement.

Figure 24A:
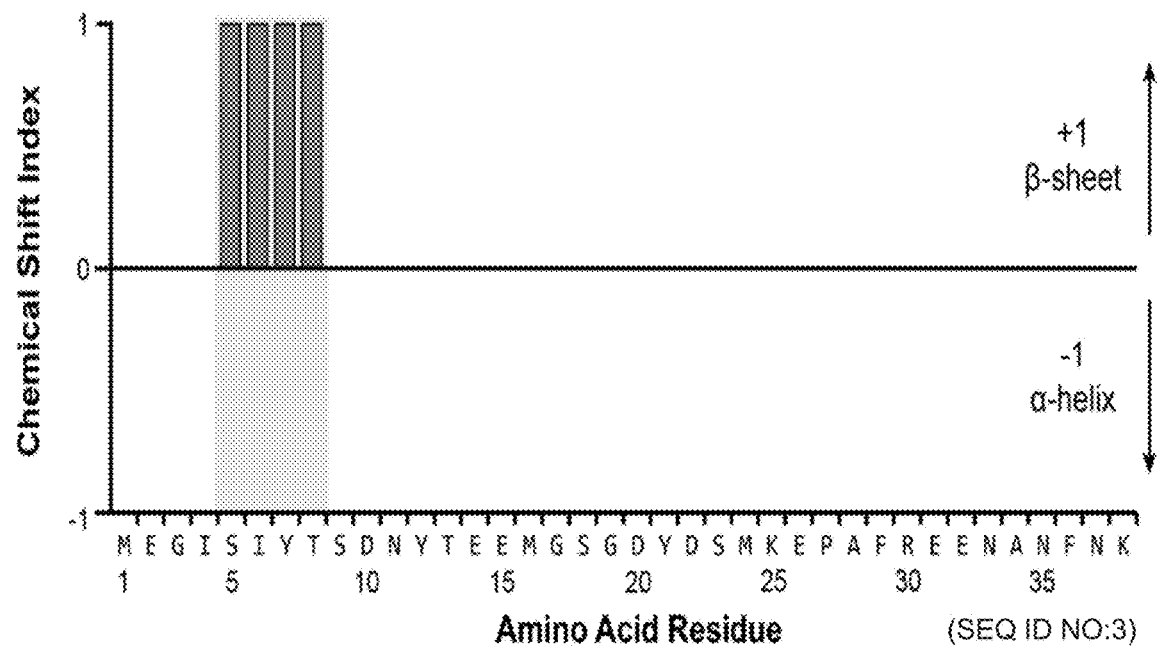
FIG. 24A. CXCR4 residues 7-9 form a fourth β-strand with CXCL12$_1$. Secondary chemical shifts were calculated for CXCR4$_{1-38}$. The consensus of H$^N$, N, C', H$^α$, C$^α$ and C$^β$ secondary chemical shifts indicate a short β-sheet comprising residues 5-8.
Figure 24B:
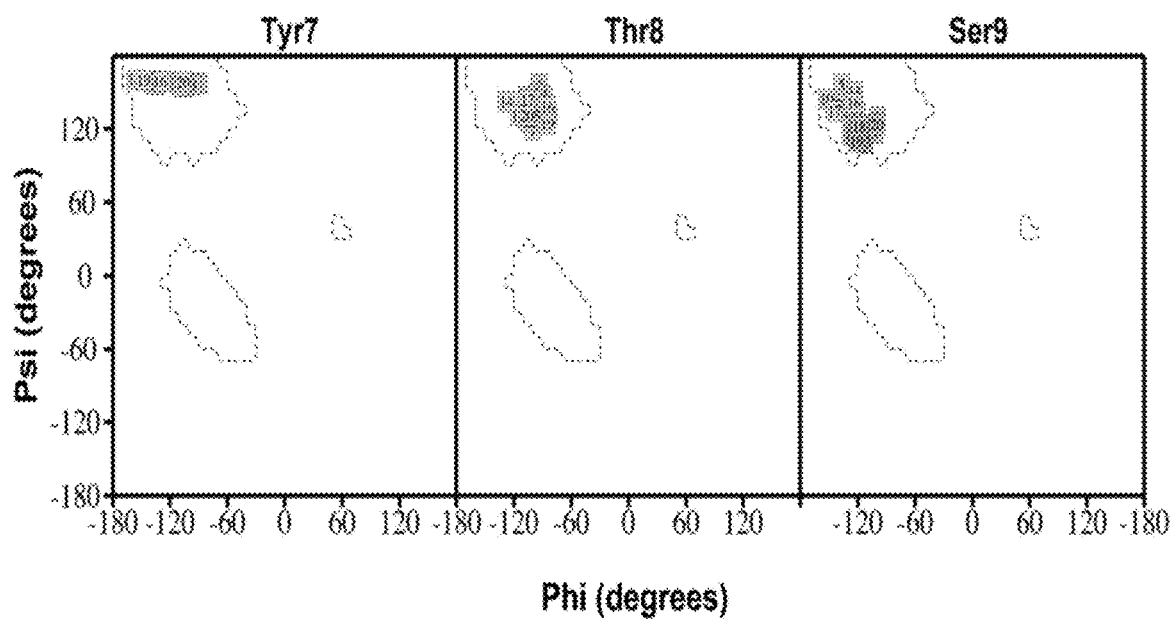
FIG. 24B. The Ramachandran statistics for Tyr7, Thr8, and Ser9 are consistent with a β-sheet.

The 1:1 and 2:2 complex interfaces sharply diverge at residues N-terminal of CXCR4 Tyr12. In the 2:2 complex, CXCR4 Tyr12 makes electrostatic contacts with Lys27 of one CXCL12$_2$ protomer and His25 of the other. Upon sulfation, sTyr12 preferentially forms salt bridges with Lys27 from a single protomer. Tyr7 also makes contacts with the other CXCL12$_2$ subunit by burying into a pocket formed by Val23 and Arg20. In the 1:1 complex Tyr12 buries into a deep cleft formed by Pro10, Lys27, Leu29, and Val 39 that possesses no obvious electrostatic or charge interactions for a sulfated tyrosine. Asp10 and Asn11 of CXCR4$_{1-38}$ then turn to place Tyr7 in close proximity to Tyr12. The Tyr7 hydroxyl is positioned toward His25 and Lys27, but productive contacts are not clear. CXCR4$_{1-38}$ residues Tyr7-Ser9 hydrogen bond with CXCL12$_1$ Ile28-Asn30 to form a four-stranded β-sheet (FIG. 20E; FIG. 24). The position of Tyr7 enables Ile6 to bury into a hydrophobic cleft surrounded by Leu26, Tyr61, and Ala65 (FIG. 20F). Ile4 packs further up the helix against CXCR4 Ile6 and CXCL12$_1$ Leu26, Trp57, and Tyr61. The interaction of hydrophobic CXCR4 residues with the CXCL12 helix is consistent with previous NMR titration studies of CXCR4$_{1-38}$ and cross-saturation NMR experiments with full-length CXCR4. Sulfation of Tyr7 reduces the binding affinity of a CXCR4 Ile4-Asp10 heptapeptide two-fold. The reduced affinity may result from a sulfated Tyr7 straining to interact with Lys27 and displacing the isoleucines from their hydrophobic cleft.

Figure 20I:
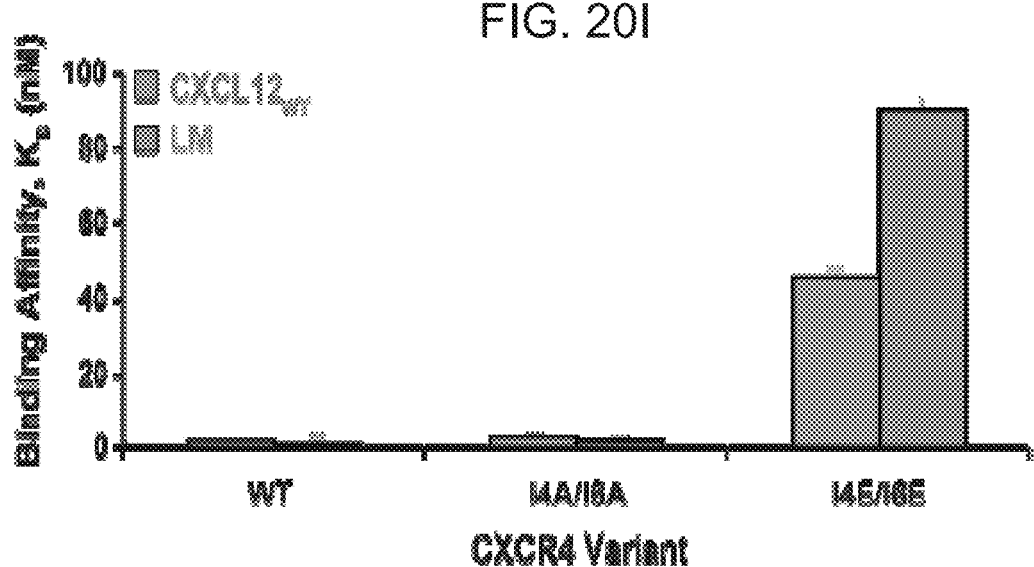
FIG. 20I. Binding affinity EC$_{50}$ of CXCL12$_{WT}$ and CXCL12$_1$ to CHO-K1 cells expressing CXCR4, CXCR4 (14A/16A), or CXCR4 (14E/16E).
Figure 20J:
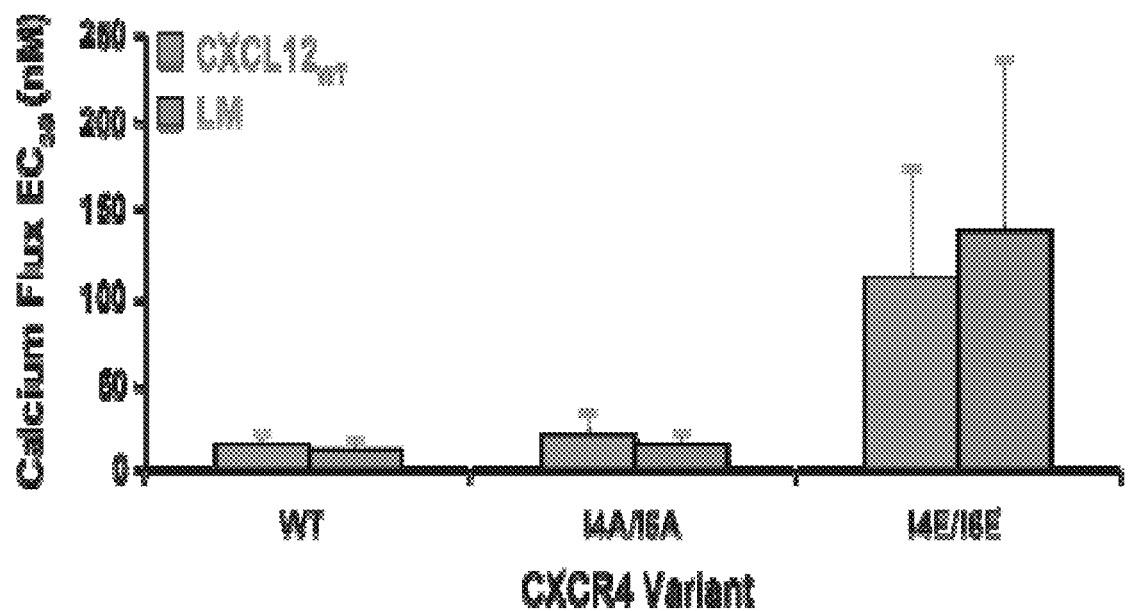
FIG. 20J. Calcium flux EC$_{50}$ of CXCL12WT and CXCL12$_1$ to CHO-K1 cells expressing CXCR4, CXCR4 (14A/16A), or CXCR4 (14E/16E).
Figure 25:
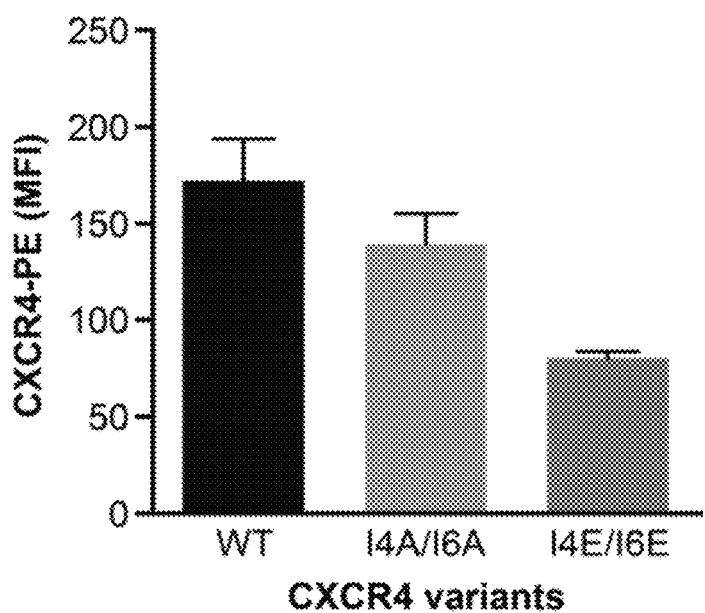
FIG. 25. Expression levels for CXCR4 mutants in HEK293E cells. The expression of CXCR4 variants at the cell surface of the transfected cells was assessed using flow cytometry. 48 h after transfection, 1×10$^6$ cells were collected and washed twice in cold PBS. Cells were then stained with CXCR4-phycoerythrin (clone 12G5) or isotype-phycoerythrin antibody according to the manufacturer's recommendation and the fluorescence was measured using a FACSCalibur flow cytometer.

The CXCR4 N-terminus is critical for chemokine recognition and activation. The CXCL12$_1$:CXCR4$_{1-38}$ complex contains a unique interface for residues 1-12 that is incompatible with CXC-type chemokine dimerization (FIGS. 20G, 20H). To assess the contributions of CXCR4 Ile4 and Ile6, we designed a series of CXCR4 mutants and monitored binding affinity and calcium flux dose responses. Ile4 and Ile6 were simultaneously mutated to either alanine or glutamic acid residues in FLAG-tagged CXCR4 (FIG. 25). Whereas alanine substitution had no effect on binding, the affinity of CXCL12$_{WT}$ and CXCL12$_1$ for glutamate mutants was reduced 30- and 90-fold, respectively (FIG. 20I). Similarly, receptor activation, monitored by the dose-dependent calcium response in CHO-KI cells, was reduced 10-fold upon mutagenesis to glutamatic acid (FIG. 20J).

Figure 21A:
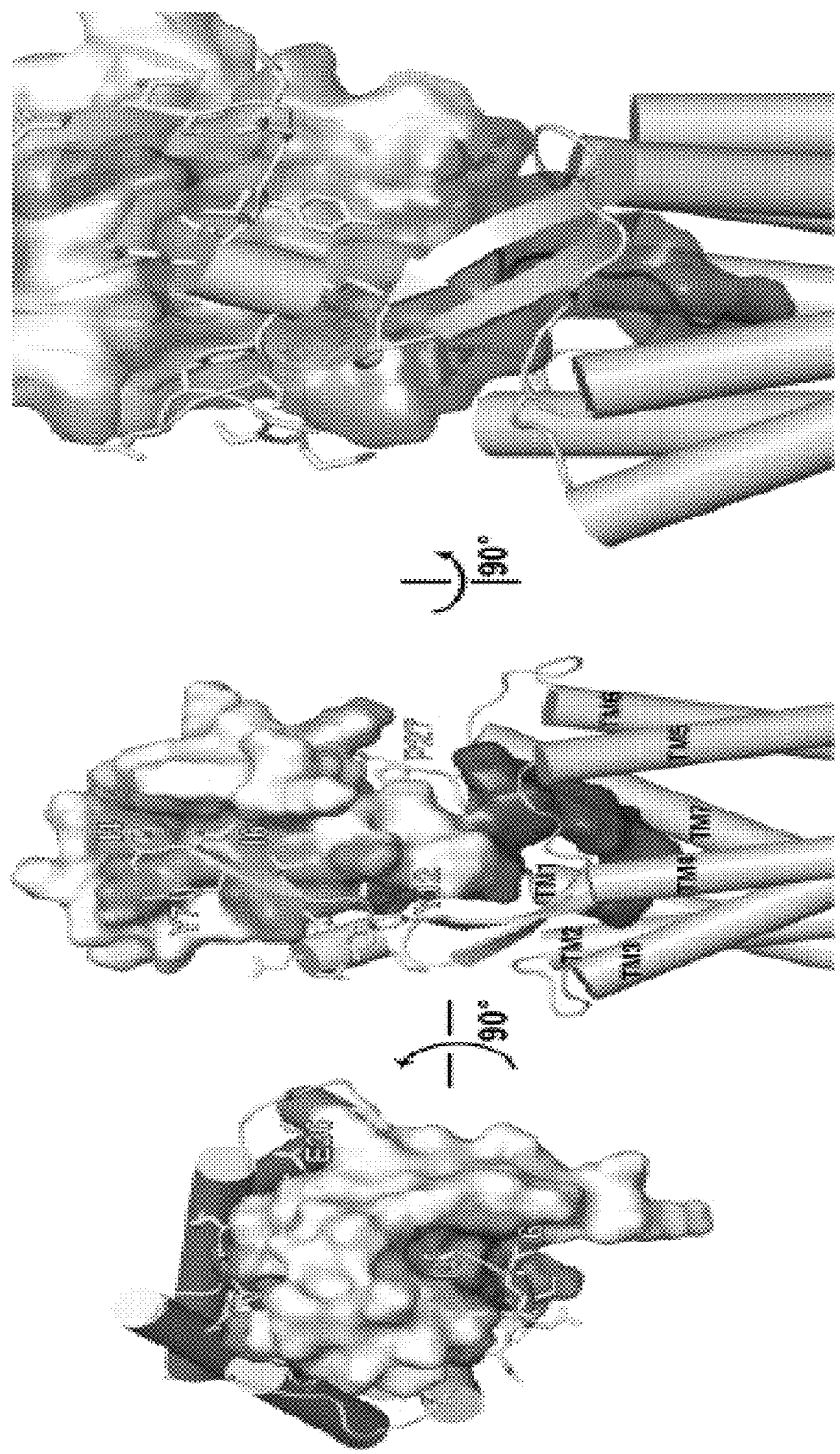
FIG. 21A. Model and experimental validation of full-length CXCL12$_1$:CXCR4 complex. Combination of the NMR structure and CXCR4 crystal structure permitted modeling of the intact, balanced signaling complex. The CXCL12 N-terminus is colored purple with additional site 2 interacts highlighted in pink. TCS data from Kofuku el al. are mapped onto CXCL12 in orange.

Structure-guided modeling of the full-length 1:1 receptor complex. No CXCL12:CXCR4 complex structure exists to date; in part because of the ligand's dimer equilibrium and the receptor's inherent conformational flexibility. Recently, Handel and colleagues proposed that both site 1 and site 2 interactions require only a single protomer of the CXCR4 dimer for full-agonist activation. Combining our CXCL12$_1$: CXCR4$_{1-38}$ NMR structure with the previously-published CXCR4 crystal structures, we were uniquely positioned to model the complete full-agonist complex (FIG. 21A). The docking of CXCL12$_1$ to CXCR4 proceeded in five steps. We first docked the CXCL12 N-terminal peptide (residues 1-8; KPVSLSYR) into the orthosteric site of CXCR4 (PDB 3ODU:A residues 29-301) using the FlexPepDock ab initio protocol. In the second step, the N-terminal peptide model from the first step and CXCR4 Pro27 (anchored by a disulfide between Cys28-Cys274) were used to roughly guide the placement of the CXCL12$_1$-CXCR4$_{1-38}$ NMR structure. In the third step, we optimized the model using the RosettaRelax protocol, and connected the structured domain of CXCR4 to the CXCR4$_{1-38}$ fragment using the Rosetta loop modeling protocol. Finally, CXCL12$_1$ residues 1-8 were re-docked to adjust to the relaxed complex using FlexPepDock ab initio.

Figure 21B:
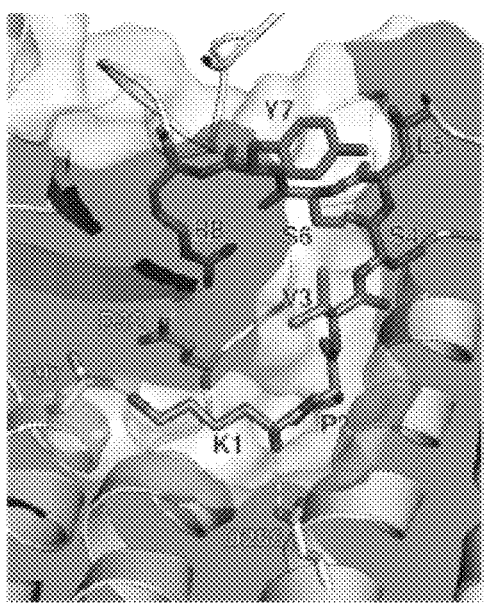
FIG. 21B. The CXCL12 N-terminal residues sit in a pocket and contact residues known to participate in chemokine binding.

Next, we inspected the model for known structure activity relationships. Deletion studies by Crump established a significant role for CXCL12 residues 1-5 in receptor recognition and activation, but showed that Ser6 and Tyr7 were not essential complex formation. In our model the chemokine N-terminus participates in both polar and apolar contacts to CXCR4 residues previously identified as critical in mutagenic calcium flux experiments. CXCL12 Lys1 sits at the base of the pocket and interacts with CXCR4 Asp97$^{2.63}$ and Glu288$^{7.39}$(FIG. 21B), which both contribute to ligand binding and are essential for receptor activation. CXCR4 Hs281$^{7.32}$ forms a polar contact with the carbonyl of CXCL12 Pro2 and CXCR4 Val196$^{5.35}$ packs near CXCL12 Val3. Deletion of residues 1-8 leads to no detectable binding, and in our model the substantial contribution of Arg8 results from a salt bridge to Glu32 near the top of the pocket (FIG. 21B).

Figure 21C:
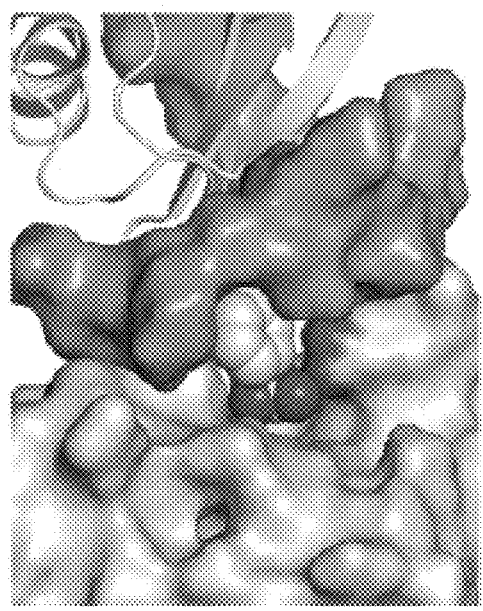
FIG. 21C. R12 of the 'site 1' RFFESH (SEQ ID NO:10) motif actually sits in the interface between sites. N33 may contribute to binding, but wouldn't be predicted by as a component of site 1 or 2.
Figure 21D:
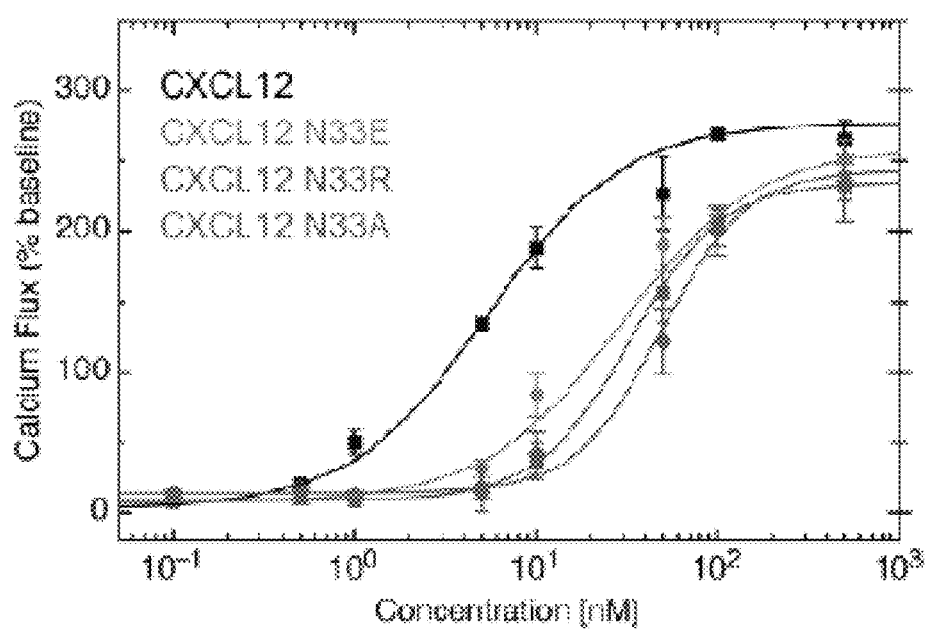
FIG. 21D. Calcium flux confirms N33 contribution.

The site 1 interaction is characterized by the CXCL12 RFFESH (SEQ ID NO:10) motif from residues 12-17 of the N-loop region. Arg12 and His17 of the RFFESH (SEQ ID NO:10) motif are stabilized in our model by Glu32 and Asp181$^{ECL2}$, respectively (FIG. 21C). One surprising feature of our model was the relatively contiguous interaction surface. The model was scanned for CXCL12 residues that haven't been previously assigned to either site 1 or 2, and would not be predictable from the current model. We identified Asn33, which is located in the CXCL12 β1-β2 loop, and is predicted to form a potential hydrogen bond with CXCR4 Asn176$^{ECL2}$. Mutation of Asn33 to alanine, glutamine or arginine reduced both calcium flux EC$_{50}$ six-fold and similarly effected chemotaxis (FIG. 21D). CXCL12:CXCR4 forms a large continuous protein-protein interface (PPI) that involves both the canonical site 1 and site 2 elements but these interfaces are actually part of one continuous PPI, suggesting that, despite its utility, the original two-site model is an oversimplification.

In addition to results from mutagenesis-based functional studies, we also validated our model using experimental distance measurements. We mapped previously published transferred cross-saturation (TCS) NMR measurements onto our model. The TCS experiments, performed using full-length CXCL12$_{WT}$, identified CXCL12 methyl-proton resonances within 5 Å of CXCR4 residues. Several methyl group resonances, including Val18$^{γ1}$, Leu26$^{δ2}$, Ile51 and Ile58, were excluded in the authors' original analyses because they were completely buried within the CXCL12 molecule and unexplainable by the prevailing model. Not only does our model support the TCS results, but it is also fully consistent with all resonances possessing intensity reductions>0.1 (FIG. 21E). Finally, the pairwise distance between residues was highly consistent with those previously identified in cysteine trapping experiments, and suggest a better overall model of the active receptor complex than previous attempts (Table 3).

TABLE 3

Pair-wise distance comparison of 1:1 CXCR4:CXCL12$_1$ model to cysteine trapping experiment. The efficacy of cysteine trapping from Kufareva et al. was qualitatively inspected and compared to the measured distance in the full-length 1:1 CXCR4:CXCL12$_1$ model.

| CXCR4 | CXCL12$_1$ | Cβ-Cβ (Å) | Intensity |
|---|---|---|---|
| Lys25 | Glu15 | 8.6 | *** |
| Lys25 | Ser16 | 8.9 | *** |
| Lys25 | His17 | 11.5 | * |
| Phe29 | Ph13 | 7.4 | ** |
| Glu31 | Arg8 | 12.7 | * |
| Glu32 | Arg8 | 10.6 | * |

Comparison of CXCL12:CXCR4 model with previous structures. CXCR4 was recently crystallized in complex with vMIP-II, an antagonistic broad-spectrum viral chemokine, by introducing a disulfide cross-link between ECL2 of the receptor and the vMIP-II N-terminus. The overall complex geometry resembles our model with site 2 orienting the axis of the chemokine β-sheet roughly parallel to the transmembrane region. Whereas the CXCL12:CXCR4 site 1 interaction contributes ~66% of the total binding energy, the vMIP-II:CXCR4 complex is primarily driven by the site 2 interaction. A comprehensive comparison of the vMIP-II:CXCR4 site 1 interaction with our CXCL12:CXCR4 model is not possible because the electron density for CXCR4 residues 1-22 is absent from the crystal structure, presumably due to disorder. The less extensive vMIP-II site 1 interface, and comparatively small contact surface (~1330 Å$^2$ buried), is further consistent with previous mutagenic studies, and may also reflect its promiscuous nature.

From our model and mutagenic analyses, the CXCL12:CXCR4 site 1.5 interface corresponds to CXCL12 residues 4-SLSYR-8 and should include two additional chemokine residues that bury ~170 Å$^2$ of surface which is neither site 1 or 2: Arg12 (immediately after the CXC motif; first residue of the RFFESH (SEQ ID NO:10) motif) and Asn33 (in the middle of the β1-β2 loop) (FIGS. 21A-C). The vMIP-II N-loop forms an intermolecular β-sheet with CXCR4 residues Pro27-Cys28, supporting CXCR4 Arg30-Ala34 to form an additional helical turn, and drawing the vMIP-II globular domain toward transmembrane helices I and II. The N-loop bulge typical of CXC-type chemokines prevent similar contacts in our model, and subsequently CXCL12 is translated toward helices V and VI. The distinct position of the CXCL12 globular domain modifies the site 2 interaction. Although the CXCL12 N-terminus is two residues shorter, Lys1 nevertheless reaches a similar depth as the vMIP-II N-terminus, and also makes critical contacts with Asp97$^{2.63}$ and Glu288$^{7.39}$, but does not form a helical structure. The expansive site 1, 1.5, and 2 interfaces in our model results in a much larger contact surface (~3300 Å$^2$) that buries nearly 40% of the entire CXCL12 surface.

Figure 26:
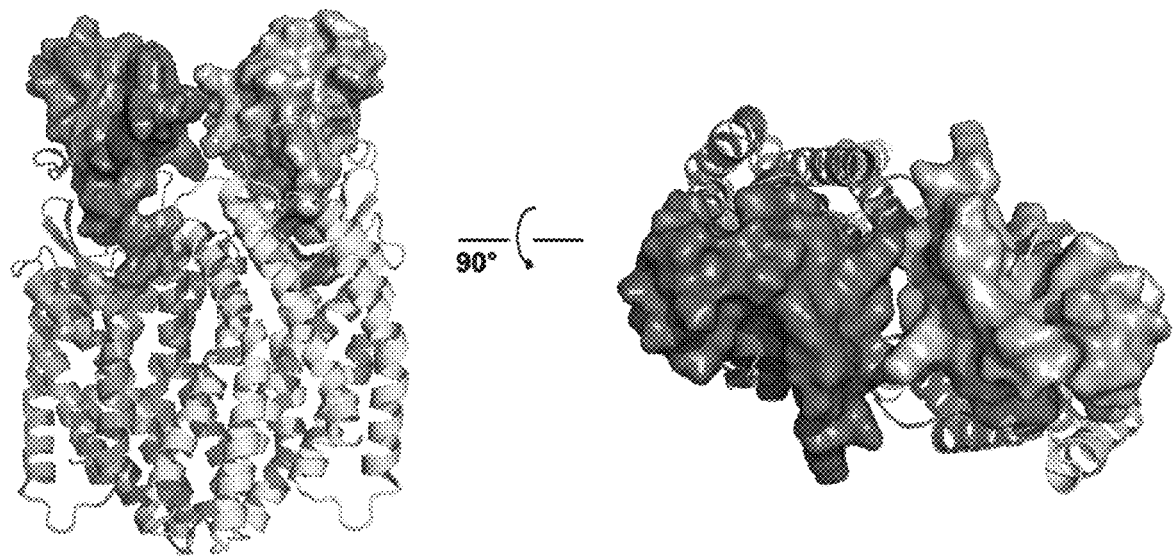
FIG. 26. CXCL12$_1$:CXCR4 model consistent with 2:2 binding stoichiometry. Two CXCL12$_1$ molecules can simultaneously maintain site 1 and site 2 interactions without steric clash.

Model-based insight into biased agonism. A tempting hypothesis for the bell-shaped chemotaxis response is CXCL12 dimerization. As CXCL12$_1$ is incapable of self-association, but still signals migratory arrest, our data would suggest that ligand-receptor stoichiometry, independent of the chemokine quaternary structure, might regulate CXCR4 function. Symmetrization of our model is compatible with two monomers simultaneously binding a CXCR4 dimer (FIG. 26), and it is reasonable to hypothesize that binding of chemokines in adjacent sites would alter intracellular receptor conformation and modify signaling. In some respects the covalent CXCL12$_2$ replicates the CXCR4 response to high CXCL12$_{WT}$ or CXCL12$_1$ concentrations such as reduced β-arrestin recruitment and a cellular idling phenotype. In comparison to CXCL12$_{WT}$, the CXCL12$_2$ binds CXCR4$_{1-38}$ four-fold tighter but recognizes the full-length receptor six-times weaker. Nonetheless, CXCL12$_2$ is a potent inhibitor of CXCL12-mediated chemotaxis. In our model, unmodified substitution of CXCL12$_1$ with CXCL12$_2$ would not be compatible with the site 1 interaction in the previously determined CXCL12$_2$:CXCR4$_{1-38}$ NMR structure, and would additionally result in steric clash between the CXCL12$_2$ helices.

Model-based insight into CXCR4 inhibitors. The pathological relevance of CXCL12:CXCR4 signaling has motivated the pursuit of small-molecule and peptide-based CXCR4 inhibitors and, more recently, direct antagonists of CXCL12. High-throughput drug discovery has produced many inhibitors of site 2, including small-molecule IT1t and the CVX15 peptide inhibitor, which were recently crystallized with CXCR4. Our model illustrates how the IT1t small-molecule inhibitor could block CXCL12-mediated receptor activation through contacts in the minor pocket with Asp97$^{2.63}$, Cys186$^{ECL2}$, and Glu288$^{7.39}$ (FIGS. 21A-C). The CVX15 peptide, which is not illustrated because our model was generated using the IT1t model, likely blocks CXCL12 binding through substantially contact overlaps to ECL2 residues Asp187-Tyr190 and helices IV, V, and VI. A sulfotyrosine binding pocket, hypothesized to be conserved structurally across the chemokine family, has recently been targeted using structure-based drug design. A crystal structure of compound 1:CXCL12 suggests that the small-molecule would compete with CXCR4 for both hydrophobic (Val18, Leu42, and Val49) and polar contacts (Glu15, Asn22 and Arg47) on CXCL12 (FIGS. 21A-C).

In addition to molecular inhibitors, our model provides structural hypotheses for the effects resulting from receptor and chemokine modifications. Sulfotyrosine modification has been demonstrated to enhance ligand affinity for CCR2b, CCR5, CCR8, CXCR3, CX$_3$CR1, and CXCR4. One notable exception is sulfation of CXCR4 Tyr7, which is slowly sulfated in vitro and has reduced affinity for CXCL12. As illustrated in our model Tyr7 recognizes an apolar pocket formed the CXCL12 β-sheet and helix (FIGS. 21A-C). Reactive nitrogen species produced in tumor microenvironments were recently shown to be immunosuppressive by modifying chemokine tyrosine residues and, subsequently, reducing their ability to recognize and activate receptors. Nitration of CXCL12 Tyr7 and Tyr61 would be hypothesized to inhibit receptor interactions and could be explained by reducing the affinity of both site 1 and 1.5 (FIGS. 21A-C).

Protein expression and purification. $CXCR4_{1-38}$, $CXCL12_{WT}$, $CXCL12_2$, and $CXCL12_1$ were produced as previously described.

Radioligand binding competition assay. HEK293E cells were seeded in Dulbecco's modified Eagle's medium supplemented with 10% fetal bovine serum, 100 units/mL penicillin/streptomycin (Life Technologies) in six well plates and transiently transfected with poly-(ethylenimine) (PEI) (Polysciences Inc.) using 2 μg/well of WT, Ile4Ala/Ile6Ala, or Ile4Glu/Ile6Glu FLAG-hCXCR4 cDNA vector. Radioligand binding was conducted 48 h post transfection. Cells were washed twice in PBS (Wisent) and incubated 5 minutes with 100 μM phenylarsine oxide (Sigma-Aldrich) in PBS at 37° C. Cells were washed twice and resuspended in binding buffer [50 mM HEPES, 5 mM $MgCl_2$, 1 mM $CaCl_2$), 0.2% (w/v) BSA, pH 7.4], seeded in 96 well flat bottom plate at 20,000 cells per well and incubated with 50 μM $^{125}$I-CXCL12 (Perkin-ECXCL121er) as a tracer and increasing concentrations of competing unlabelled chemokine, for 30 minutes at 37° C. Bound radioactivity was separated from free ligands by filtration on borosilicate filter paper (Molecular Devices) treated with a 0.33% PEI solution. Receptor-bound radioactivity was quantified by gamma-radiation counting (Perkin-ECXCL121er Life and Analytical Sciences). Binding experiments were carried out in duplicate.

THP-1 calcium response. THP-1 monocyte cells were washed twice and resuspended in 96-well format at $2\times10^5$ cells/well in assay buffer: Hanks buffered saline solution (HBSS), 20 mM HEPES (pH 7.4), 0.1% (w/v) BSA, and FLIPR Calcium4 dye (Molecular Devices) and then incubated for 1 h at 37° C., 5% $CO_2$. Fluorescence was measured at 37° C. using a FlexStation3 Microplate Reader (Molecular Devices) with excitation and emission wavelengths of 485 nm and 515 nm, respectively. Chemokines were resuspended at the indicated concentrations and added to the cells following a 20 s baseline fluorescence measurement. Percent calcium flux was calculated from the maximum fluorescence minus the minimum fluorescence as a percent of baseline. $EC_{50}$ values were determined by non-linear fitting to a four parameter logistic function.

NALM6 chemotaxis. NALM6 cells were grown in RPMI-1640 supplemented with 10% FBS, 100 U/mL penicillin-streptomycin, 2 mM glutamine, 50 μM 2-mercaptoethanol, non-essential amino acids, 1 mM Na-pyruvate and 25 mM HEPES buffer (pH 7.3). Chemotaxis assays were performed in triplicate in 48-well Boyden chambers (NeuroProbe), using 5 μm pore-sized polyvinylpyrrolidone-free polycarbonate membranes. Chemotaxis medium (RPMI-1640, 25 mM HEPES supplemented with 1% FBS) alone or chemotaxis medium containing increasing concentrations of CXCL12 variants was added to the lower wells. Cells ($1\times10^5$ per well) resuspended in chemotaxis medium were added to the upper well and incubated for 90 min at 37° C. in 5% $CO_2$ atmosphere. Cells were removed from the upper part of the membrane with a rubber policeman. Cells attached to the lower side of the membrane were fixed and stained as described. Migrated cells were counted in five randomly selected fields of 1000-fold magnification.

MiaPaCa2 chemotaxis. Chemotactic migration of pancreatic cancer MiaPaCa2 cells was performed as previously described using Transwell plates coated with 15 ug/ml collagen. Briefly, MiaPaCa2 cells were serum starved for 2 hours, lifted using enzyme-free dissociation buffer, washed and then counted using a hemocytometer. 100,000 cells in 10 uL of serum free media were plated into the top chamber of each Transwell. The bottom chamber of each Transwell contained each stimulant in 500 uL serum free media. MiaPaCa2 cells were allowed to migrate for 6 hours, after which the cells remaining on the top of the chamber were swabbed out. Plates were then fixed in 4% paraformaldehyde and stained with DAPI. Migrated cells were visualized and counted by fluorescence microscopy, with 5 representative high-powered fields taken per well.

β-arrestin-2 recruitment. β-arrestin-2 recruitment was measured using an intermolecular BRET assay performed as described previously. Briefly, HEK293e cells were cotransfected with 1 μg of $GFP_{10}$-β-arrestin-2 construct and 0.05 μg of CXCR4-RLuc3. All transfections were completed to 2 μg of DNA per well with empty vector. Following overnight culture, transiently transfected cells were seeded in poly-D-lysine-coated 96-well white clear-bottom microplates (View-Plate, Perkin-ECXCL121er Life and Analytical Sciences) and left in culture for 24 h. The medium of the cells was then changed to BRET buffer (PBS, 0.5 mM $MgC_2$, 0.1% (w/v) BSA). β-arrestin-2 recruitment was measured 15 min after ligand addition, and 10 min after the addition of the RLuc3 substrate coelenterazine400a (NanoLight Technology) at a final concentration of 5 mM. The values were corrected to BRETnet by subtracting the background BRET signal obtained in cells transfected with the luciferase construct alone.

Agarose microdroplet assay. The agarose microdroplet assay was performed to determine U-937 cellular migration, as previously described {$AdeCXCL12_1an$, 1980 #1609}. $0.5\times10^6$ cells/ml U-937 target cells were harvested and washed in HBSS. Cells were spun at 2,000 rpm and were transferred to a graduated 15 ml glass conical tube. The cell concentration was adjusted in agarose medium, prepared from 2% low melting temperature Seaplaque agarose and medium containing 15% FBS, using a 1:4 volume-to-volume dilution. A 1 si agarose droplet containing $1\times10^5$ target cells was placed in the center of each well of a 96-well flat-bottom tissue culture plate, in triplicate, using a gastight 0.05 ml Hamilton syringe (Hamilton Company, Reno, Nev.). Droplets were allowed to harden at 4° C. for 20 min. 200 μl chilled test media was applied to each well. Test medium consisted of serum-free medium, 25% FBS, and the indicated CXCL12 concentrations. The plate was incubated for 18-24 h at 37° C. and 5% $CO_2$. Following incubation, the radius of each droplet was determined and target cell migration was measured at four directional points 900 from one another, using an inverted light microscope equipped with a gridded eyepiece, at 40× total magnification. Percent inhibition of each sample was quantified. The plate was incubated for an additional 24 h to measure recovery, and viability was determined by trypan blue exclusion.

NMR structure determination. All NMR spectra were acquired on a Bruker DRX 600 MHz spectrometer equipped with a $^1$H, $^{15}$N, $^{13}$C TXI cryoprobe at 298 K. Experiments were performed in a solution containing 25 mM deuterated MES (pH 6.8), 10% (v/v) $D_2O$, and 0.02% (w/v) $NaN_3$. NOE distance restraints were obtained from 3D $^{15}$N-edited NOESY-HSQC, aliphatic $^{13}$C-edited NOESY-HSQC, and aromatic $^{13}$C-edited NOESY-HSQC spectra ($\tau_{mix}$=80 ms) collected on both [U-$^{15}$N,$^{13}$C]-CXCL12$_1$ saturated with CXCR4$_{1-38}$ and [U-$^{15}$N,$^{13}$C]-CXCR$_{1-38}$ saturated with CXCL12$_1$. Intermolecular NOEs were obtained from a 3D F1-$^{13}$C/$^{15}$N-filtered/F3-$^{13}$C-edited NOESY-HSQC ($\tau_{mix}$=120 ms) collected on both [U-$^{15}$N,$^{13}$C]-CXCL$_{1-38}$ saturated with CXCR4$_{1-38}$ and [U-$^{15}$N,$^{13}$C]-CXCR$_{1-38}$ saturated with CXCL12$_1$. In addition to NOEs, backbone φ/ψ dihedral angle restraints were derived from $^1$H$^N$, $^1$H$^\alpha$, $^{13}$C$^\alpha$, $^{13}$C$^\beta$, $^{13}$C', and $^{15}$N chemical shift data using TALOS+. Both distance and dihedral restraints were used to generate initial NOE assignments and preliminary structures via the NOE-ASSIGN module of CYANA. Complete structure determination was undertaken as an iterative process of correcting/assigning NOEs and running structure calculations with CYANA. The 20 CYANA conformers with the lowest target function were further refined by a molecular dynamics protocol in explicit solvent using XPLOR-NIH.

2D NMR characterization. All NMR spectra were acquired on a Bruker DRX 600 MHz spectrometer equipped with $^1$H, $^{15}$N, $^{13}$C TXI cryoprobe at 298 K. Experiments were performed in a solution containing 25 mM deuterated MES (pH 6.8), 10% (v/v) D$_2$O, and 0.02% (w/v) NaN$_3$. Heteronuclear NOE experiments were collected on 250 μM [U-$^{15}$N]-CXCR4$_{1-38}$ in the absence and presence of 500 μM CXCL121. $^{15}$N-HSQC spectra were collected to monitor the interaction of 200 μM [U-$^{15}$N]-CXCR4$_{1-38}$ was titrated with 0, 100, 200, 300, 400, and 500 μM CXCL12$_2$. $^{15}$N-HSQC spectra were collected to monitor the interaction of 250 μM [U-$^{15}$N]-CXCR4$_{1-38}$ was titrated with 0, 62.5, 125, 187.5, 250, 375 and 500 μM CXCL121.

Calcium response of (XCR4 mutants. Cell culture, transfection and calcium flux assay of Chinese hamster ovary K1 (CHO-K 1) cells was performed as previously described Cell lines, antibodies and other reagents. HEK (Human embryonic kidney) 293 (Microbix, Toronto, Canada) and HeLa (American Type Culture Collection) cells were maintained in Dulbecco's modified Eagles medium (DMEM; Hyclone) supplemented with 10% fetal bovine serum (FBS; HyClone Laboratories, Logan, Utah). The PE-conjugated CXCR4 (CD184) isotype control antibodies, and rat anti-CXCR4 (2B111) and were from BD Biosciences (San Jose, Calif.). The anti-actin antibody was from MP Biomedicals (Aurora, Ohio). The Alexa-Fluor 568-conjugated goat anti-rabbit antibody was from Molecular Probes (Eugene, Oreg.). The anti-FLAG M2 horseradish peroxidase conjugated monoclonal antibody was from Sigma (St. Louis, Mo.). The anti-HA polyclonal and monoclonal antibodies were from Covance (Berkeley, Calif.). CXCL12 was from PeproTech (Rockyhill, N.J.).

CXCR4 surface expression. In parallel to radioligand binding, the expression of CXCR4 variants at the cell surface of the transfected cells was assessed using flow cytometry. 48 h after transfection, 1×10$^6$ cells were collected and washed twice in cold PBS. Cells were then stained with CXCR4-phycoerythrin (clone 12G5; eBioscience) or isotype-phycoerythrin antibody according to the manufacturer's recommendation. The fluorescence was measured using a FACSCalibur flow cytometer (BD Bioscience).

CXCR4 degradation assay. HeLa cells grown on 6-cm dishes were washed once and incubated with DMEM containing 10% FBS and 50 μg/ml cycloheximide for 15 min at 37° C. Cells were then incubated in the same medium containing vehicle (PBS containing 0.5% bovine serum albumin [BSA]), 80 ng/ml CXCL12$_{WT}$, CXCL12$_1$, or LD for 3 h. Cells were washed once and collected in 300 μl 2×sample buffer. Receptor levels were determined by SDS-PAGE followed by immunoblotting using an anti-CXCR4 antibody. Blots were stripped and reprobed for actin to assess loading. Receptor levels normalized to actin levels were determined by densitometric analysis.

CXCR4 internalization assay. HeLa cells grown on 6-cm dishes were washed twice with PBS and detached from the surface of the plate by incubating with 350 μl Cellstripper cell dissociation solution (Mediatech, VA) for 10 min at 37° C. Cells were collected in 4 ml PBS containing 0.1% BSA (Media Tech, VA) by centrifugation. Cell pellets were re-suspended in 1.5 ml PBS-0.1% BSA and 5×10' cells were transferred to a fresh 5 ml polystyrene round bottom tube (BD falcon) and washed once with PBS+0.1% BSA and re-suspended in 250 μl PBS-0.1% BSA. Cells were incubated at 37° C. for 15 min and then treated with vehicle, 80 ng/ml CXCL12$_{WT}$, CXCL12$_1$, or LD for 20 min at 37° C. Following treatment, 4 mL cold PBS was added to each tube, cells were collected by centrifugation and then fixed by re-suspending the pellet in 500 μl 4% paraformaldehyde (made in PBS) and incubating for 15 min at 37° C. Cells were collected by centrifugation and washed once with 4 mL PBS and then twice with PBS-0.1% BSA. Cells were stained with PE-conjugated anti-CXCR4 or isotype control antibodies by re-suspending the pellet in 100 μl PBS-0.1% BSA (supplemented with 5% normal goat serum) containing anti-CXCR4 antibody (1:100 dilution) and incubating for 1 hour at room temperature in the dark. Following staining, cells were washed twice with 4 mL PBS-0.1% BSA. Finally, cells were re-suspended in 300 μl PBS-0.1% BSA and kept in the dark until the analysis was performed. CXCR4 surface expression was analyzed by flow cytometry (FACS-CANTO; Becton Dickinson) and analysis was performed using FlowJo v.9.3 software.

CXCR4 ubiquitination assays. HEK293 cells stably expressing HA-CXCR4 grown on 10-cm dishes were transfected with 3 μg FLAG-ubiquitin. The next day, cells were passaged onto 6-cm dishes and allowed to grow for an additional 24 h. The following day, cells were incubated in DMEM containing 20 mM HEPES for 6 h and then treated with vehicle (PBS, 0.1% BSA), 80 ng/ml CXCL12$_{WT}$, CXCL121, or LD for 30 min. Cells were then washed once on ice with cold PBS, and collected in 1 ml lysis buffer [50 mM Tris-Cl, pH 7.4, 150 mM NaCl, 5 mM EDTA, 0.5% (w/v) sodium deoxycholate, 1% (v/v) NP-40, 0.1% (w/v) SDS, 20 mM N-ethyCXCL121aleimide (NEM), and 10 μg/ml each of leupeptin, aprotinin, and pepstatin A]. Samples were transferred into microcentrifuge tubes and placed at 4° C. for 30 min, followed by sonification and centrifugation to pellet cellular debris. Clarified cell lysates were incubated with an anti-HA polyclonal and isotype control antibodies and the immunoprecipitates were analyzed by SDS-PAGE followed by immunoblotting using an anti-FLAG antibody conjugated to HRP.

Confocal microscopy. HeLa cells transiently transfected with HA-CXCR4-YFP were passaged onto poly-L-lysine coated coverslips and grown for 24 h. The next day, cells were washed once with warm DMEM containing 20 mM HEPES, pH 7.5, and incubated in the same medium for 3-4 h at 37° C. Cells were treated with 80 ng/ml CXCL12$_{WT}$, CXCL121, or LD and vehicle for 30 min. Cells were then fixed with PBS containing 3.7% paraformaldehyde, followed by permeabilization with 0.05% (w/v) saponin for 10 min, similar to a protocol we have described previously. Cells were then incubated with 1% goat serum in 0.05% saponin-PBS for 30 min at 37° C., followed by staining with anti-mouse monoclonal antibody that recognizes dually phosphorylated CXCR4 on serine residues 324 and 325

(clone 5E11) (1:50 dilution) for 1 h at 37° C. Cells were washed five times with 0.05% saponin-PBS, followed by incubating with Alexa-Fluor 568-conjugated anti-rabbit antibody for 30 min at 37° C. (1:200 dilution). Finally, cells were washed five times with 0.05% saponin-PBS and mounted onto glass slides using mounting media containing 4,6-diamidino-2-phenylindole (Vectashield mounting media with DAPI). Samples were analyzed using an LSM 510 laser scanning confocal microscope (Carl Zeiss, Thornwood, N.Y.) equipped with a Plan-Apo 63×/1.4 oil lens objective. Images were acquired using a 1.4-megapixel cooled extended spectra range RGB digital camera set at 512×512 resolution. Acquired images were analyzed using ImageJ, version 1.410 software (National Institutes of Health, Bethesda, Md.) and Adobe Photoshop (CS4).

Apoptosis assays. KG1a (human acute myelogenous leukemia) cells were assayed for CXCL12-dependent apoptosis as previously described. Briefly, CXCR4 expression on KG1a cells was achieved via transient transfection with a plasmid encoding a CXCR4-YFP fluorescent fusion protein. These cells were treated with the indicated concentration of each CXCL12 variant and cultured for 16-18 h prior to measuring apoptosis. Apoptosis was assayed by staining cells with APC-conjugated annexin V to detect cell-surface phosphatidyl serine (BD Biosciences) or Alexaflour-647-conjugated antibody to detect cleaved PARP (BD Biosciences), and the percentage of YFP+ cells undergoing apoptosis was determined by flow cytometry.

Modeling CXCR4:CXCL12$_1$ complex—Docking of CXCL12$_1$ N-terminal peptide to CXCR4. The CXCL12$_1$ N' peptide (residues 1-8; KPVSLSYR) was docked into the orthosteric site of CXCR4 (PDB 3ODU:A residues 29-301). The peptide was manually placed away from the receptor, at a canonical extended conformation ($\phi,\psi$+−135). 90,000 models were generated using FlexPepDock Ab-Initio, out of which the top 500 by reweighted sc were clustered (at a threshold of 2 Å peptide RMSD). Next, four representative cluster centers in which the peptide was occupying the presumed binding site were selected to seed the generation of additional 100,000 models, again using FlexPepDock Ab-Initio, and the top 500 were clustered as before. A top scoring cluster representative was selected based on electrostatic interactions with experimentally important CXCR4 residues (D97/E288).

Initial placement of SDF (-terminal domain. A truncated version of the CXCL12$_1$/CXCR4$_{1-38}$ NMR complex (CXCL12$_1$ residues 9-78, CXCR4$_{1-38}$ residues 4-26; both taken from the first model of the NMR ensemble) was manually placed onto CXCR4, such that CXCL21 Cys9 was in the vicinity of Arg8 of the docked N' peptide from step 1, and Pro27 of CXCR4 will be in the vicinity of Glu26 (from the CXCL12$_1$/CXCR4$_{1-38}$ NMR complex). We considered Pro27 to be relatively rigid as it is followed by Cys28, which forms a disulfide bridge to Cys274. To validate this initial manual placement, a local RosettaDock run was initiated from this starting pose and indeed resulted in a noticeable energy funnel leading towards the starting pose.

Computational relaxation of the complex between CXCL1.21 and CXCR4. The manually placed CXCL12$_1$/CXCR4 complex from step 2 was subjected to a Rosetta Relax run, generating 5,000 models in which the backbone and sidechain conformations of the protein partners and the rigid body orientation were optimized. The top model according to Rosetta Score12 was progressed to loop modeling.

Loop modeling between CXCR4$_{1-38}$ and CXCR4. Rosetta loop modeling protocol was used to model CXCR4 residues Tyr21 to Pro27 and close the loop between the CXCR4$_{1-38}$ fragment from the NMR model (residues 4-26) and CXCR4 X-ray structure (residues 29-301). 1000 loop models were generated in the presence of CXCL12$_1$ using the perturb/refine kinematic loop closure protocol. The top scoring model was used for the subsequent modeling step.

Redocking of CXCL12$_1$ N-terminal peptide and CXCL12$_1$ loop closure. Using FlexPepDock Ab-Initio as in step 1, we produced 30,000 models of CXCL12$_1$ N' peptide (residues 1-8) starting from its previous pose (see above), but this time using constraints that would later force connectivity to residue Cys9 of CXCL12$_1$ coordinates from step 3 (Bound Rosetta restraints with standard deviation of 0.1 Å), and contact with key binding site residue Asp97 and Glu288 (distance 1.25-1.35 Å for C atom of residue 8 and N atom of residue 9; distance 2.35-2.45 Å for C atom of residue 8 and CA atom of residue 9; distance 2.35-2.45 Å for CA atom of residue 8 and N atom of residue 9; Binding site constraints on Asp97 and Glu288, in both centroid mode (range 1.0-5.5 Å for Asp97 CB atom and 1.0-6.5 Å for Glu288 CB atom), and in full atom mode (range 1.0-5.0 Å for both Asp97 CB atom and Glu288 CG atom).

The top 500 models were clustered as previously and cluster #27 was selected from the top scoring clusters as a representative favorable contacts to previously defined binding site residues. A second round of peptide docking was performed starting from this model now in the presence of the CXCL12$_1$/CXCR4$_{1-38}$ complex (except for Cys9 that was omitted to avoid clashes). The same constraints were used, to keep the peptide close to Asp97/Glu288 and to force connectivity to Cys9 in next step. The top scoring model was used for loop closure of residues 6-9 (as above) to connect CXCL12$_1$ N' peptide to rest of CXCL12$_1$. Finally another relaxation of the complete complex generated 100 models in which correct disulfide topology was enforced. The top scoring model of this relax run is presented.

Statistical Analysis and final figures. Data were analyzed by one-way analysis of variance(ANOVA) using GraphPad Prism 4.0 (GraphPad Software).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All technical publications, patents and published patent applications cited herein are hereby incorporated by reference in their entirety for all purposes.

REFERENCES CITED

1. Ma et al. (1998) *Proc. Natl. Acad. Sci. U.S.A* 95, 9448-9453.
2. Zou et al. (1998) *Nature* 393, 595-599.
3. Sierro et al. (2007) *Proc. Natl. Acad. Sci. U.S.A* 104, 14759-14764.
4. Burns et al. (2006) *J. Exp. Med* 203, 2201-2213.
5. Hu et al. (2007) *Circulation* 116, 654-663.
6. Saxena et al. (2008) *Circulation* 117, 2224-2231.
7. Proulx et al. (2007) *Pfluegers Arch.* 455, 241-250.

8. Endres et al. (1996) *Cell* 87, 745-756.
9. Balkwill, F. (2004) *Nat. Rev. Cancer* 4, 540-550.
10. Crump et al. (1997) *EMBO J.* 16, 6996-7007.
11. Kofuku et al. (2009) *J. Biol. Chem.* 284, 35240-35250.
12. Farzan et al. (2002) *J. Biol. Chem.* 277, 29484-29489.
13. Seibert et al. (2008) *Biochemistry* 47, 11251-11262.
14. Farzan et al. (1999) *Cell* 96, 667-676.
15. Preobrazhensky et al. (2000) *J. Immunol.* 165, 5295-5303.
16. Bannert et al. (2001) *J. Exp. Med* 194, 1661-1673.
17. Colvin et al. (2006) *Mol. Cell. Biol.* 26, 5838-5849.
18. Gutierrez et al. (2004) *J. Biol. Chem.* 279, 14726-14733.
19. Fong et al. (2002) *J. Biol. Chem.* 277, 19418-19423.
20. Rajarathnam et al. (1994) *Science* 264, 90-92.
21. Paavola et al. (1998) *J. Biol. (hem.* 273, 33157-33165.
22. Laurence et al. (2000) *Biochemistry* 39, 3401-3409.
23. Proudfoot et al. (2003) *Proc. Natl. Acad. Sci. U.S.A* 100, 1885-1890.
24. Tan et al. (2012). *Biol. Chem.* 287, 14692-14702.
25. Veldkamp et al. (2008) *Sci. Signaling* 1, ra4.
26. Drury et al. (2011) *Proc. Natl. Acad. Sci. U.S.A*
27. Takekoshi et al. (2012)*Mol. Cancer Ther.* 11, 2516-2525.
28. Veldkamp et al. (2006) *J. Mol. Biol.* 359, 1400-1409.
29. Veldkamp et al. (2010) *J. Am. Chem. Soc.* 132, 7242-7243.
30. Ziarek et al. (2013) *Curr. Top. Med Chem.* 12, 2727-2740.
31. Ziarek et al. (2011)*Int. J. Mol. Sci.* 12, 3740-3756.
32. Veldkamp et al. (2005) *Protein Sci.* 14, 1071-1081.
33. Veldkamp et al. (2009) *Protein Sci.* 18, 1359-1369.
34. Dombkowski, A. A. (2003) *Bioinformatics* 19, 1852-1853.
35. Gozansky et al. (2005) *J. Mol. Biol.* 345, 651-658.
36. Simpson et al. (2009) *Chem. Biol.* 16, 153-161.
37. Zhu et al. (2011) *Biochemistry* 50, 1524-1534.
38. Tan et al. (2013) *J. Biol. Chem.* 288. 10024-10034.
39. Wells, J. A., and McClendon, C. L. (2007) *Nature* 450, 1001-1009.
40. Nielsen et al. (2012) *Haemophilia* 18, e397-398.
41. Duma et al. (2007) *J. Mol. Biol.* 365, 1063-1075.
42. Pawson, T., and Nash, P. (2003) *Science* 300, 445-452.
43. Edwards et al. (2007) *PLoS ONE* 2, e967.
44. Machida, K., and Mayer, B. J. (2005) *Biochim. Biophys. Acta* 1747, 1-25.
45. Vidler et al. (2012) *J. Med. Chem.* 55, 7346-7359.
46. Herold et al. (2011) *Curr. Chem. Genomics* 5, 51-61.
47. Stone et al. (2009) *New Biotechnol.* 25, 299-317.
48. Peterson, F. C., and Volkman, B. F. (2009) *Front. Biosci.* 14, 833-846.
49. Monigatti et al. (2002) *Bioinformatics* 18, 769-770.
50. Liu et al. (2008) *Am. J. Respir. Cell Mol. Biol.* 38, 738-743.
51. Keller, R. (2004) *The Computer Aided Resonance Assignment/Tutorial*, CANTINA, Zurich.
52. Ziarek, et al. (2011) *Methods Enzymol.* 493, 241-275.

The invention claimed is:

1. A method of reducing inflammation in a subject suffering from inflammation, the method comprising administering to the subject a therapeutically effective amount of a composition comprising a constitutively monomeric CXCL12 peptide comprising the amino acid sequence of SEQ ID NO:1 wherein the amino acids at positions 55 and 58 are substituted with cysteine.

2. The method of claim 1, wherein CXCL12 peptide is $CXCL12_1$ having the amino acid sequence of SEQ ID NO:2.

3. The method of claim 1, wherein the inflammation is associated with a disease selected from the group consisting of Multiple Sclerosis (MS), Guillain-Barre Syndrome, Amyotrophic Lateral Sclerosis, Parkinson's disease, Alzheimer's disease, Type I diabetes, lupus, ankylosing spondylitis, rheumatoid arthritis, psoriatic arthritis, juvenile arthritis, early arthritis, reactive arthritis, osteoarthritis, ankylosing spondylitis, autoimmune uveitis, and inflammatory bowel diseases.

4. The method of claim 1, wherein the subject has inflammation associated with Type I diabetes.

5. The method of claim 4, wherein the subject is a human.

6. The method of claim 1, wherein the subject is a mammal.

7. The method of claim 1, wherein the composition further comprises a pharmaceutically acceptable carrier or diluent.

* * * * *

UNITED STATES PATENT AND TRADEMARK OFFICE
CERTIFICATE OF CORRECTION

PATENT NO. : 11,369,662 B2
APPLICATION NO. : 16/745809
DATED : June 28, 2022
INVENTOR(S) : Brian Volkman et al.

It is certified that error appears in the above-identified patent and that said Letters Patent is hereby corrected as shown below:

In the Specification

Column 1, Line 31, "3,394 t in" should be --3,394 bytes in--.

Column 5, Line 35, "ml$^{-1}$" should be --mol$^{-1}$--.

Column 5, Line 37, "ml$^{-1}$" should be --mol$^{-1}$--.

Column 5, Line 38, "ml$^{-1}$" should be --mol$^{-1}$--.

Column 5, Line 39, "ml$^{-1}$" should be --mol$^{-1}$--.

Column 6, Line 4, "CSCL12$_1$" should be --CXCL12$_1$--.

Column 6, Line 13, "$^{12}$I-" should be --$^{125}$I- --.

Column 10, Line 44, "(14A/16A)" should be --(I4A/I6A)--.

Column 10, Line 44, "(14E/16E)" should be --(I4E/I6E)--.

Column 10, Line 47, "(14A/16A)" should be --(I4A/I6A)--.

Column 10, Line 47, "(14E/16E)" should be --(I4E/I6E)--.

Column 13, Line 4, "158C" should be --I58C--.

Column 19, Line 62, "200/%" should be --20%--.

Column 22, Line 49, "158C"" should be --I58C--.

Signed and Sealed this
Thirteenth Day of September, 2022

Katherine Kelly Vidal
*Director of the United States Patent and Trademark Office*

CERTIFICATE OF CORRECTION (continued)
U.S. Pat. No. 11,369,662 B2

Column 22, Line 57, "158C" should be --I58C--.

Column 22, Line 59, "138C" should be --I38C--.

Column 23, Line 56, "$CXCR4_{1.38}$" should be --$CXCR4_{1-38}$--.

Column 25, Line 49, "Tyr2l" should be --Tyr21--.

Column 25, Line 60, "$CXCL12\%^r r$" should be --$CXCL12_{WT}$--.

Column 34, Line 12, "$-sheet" should be --β-sheet--.

Column 34, Line 37, "Tyr2l" should be --Tyr21--.

Column 34, Line 40, "Tyr2l" should be --Tyr21--.

Column 37, Line 23, "of$^{21}$I-CXCL12" should be --of $^{125}$I-CXCL12--.

Column 38, Line 1, "$1\times10$'" should be --$1\times10^5$--.

Column 38, Line 65, "900" should be --90°--.

Column 40, Line 55, "Connfocal" should be --Confocal--.

Column 42, Line 42, "of$NACXCL12_{16}$" should be --of $NACXCL12_{16}$--.

Column 43, Line 2, "$CXCL12_1$" should be --CXCL121--.

Column 43, Line 4, "$CXCL12_1$" should be --CXCL121--.

Column 44, Line 7, "CS" should be --Cδ--.

Column 44, Line 37, "$CXCR4_{1-38}$ a resonances" should be --$CXCR4_{1-38}$ resonances--.

Column 45, Line 5, "550" should be --55°--.

Column 45, Line 16, "1-strand" should be --β-strand--.

Column 45, Line 29, "03" should be --β3--.

Column 45, Line 38, "Glul5" should be --Glu15--.

Column 46, Line 29, "30DU:A" should be --3ODU:A--.

Column 46, Line 37, "$CXCL12_1$" should be --$CXCL1_21$--.

CERTIFICATE OF CORRECTION (continued)
U.S. Pat. No. 11,369,662 B2

Column 46, Line 51, "Hs281$^{7.32}$" should be --His$^{7,32}$--.

Column 50, Line 28, "MgC$_2$" should be --MgCl$_2$--.

Column 50, Line 55, "900" should be --90°--.

Column 51, Line 6, "CXCL$_{1-38}$" should be --CXCL12$_1$--.

Column 51, Line 32, "(XCR4" should be --CXCR4--.

Column 51, Line 65, "CXCL12$_1$" should be --CXCL121--.

Column 52, Line 16, "CXCL12$_1$" should be --CXCL121--.

Column 53, Line 32, "30DU:A" should be --3ODU:A--.

Column 53, Line 45, "SDF (-terminal" should be --SDFI C-terminal--.

Column 53, Line 49, "CXCL21" should be --CXCL12$_1$--.

Column 53, Line 59, "CXCL1.21" should be --CXC:12$_1$--.